(12) United States Patent
Wong et al.

(10) Patent No.: US 8,234,079 B2
(45) Date of Patent: Jul. 31, 2012

(54) METHOD AND/OR APPARATUS OF OLIGONUCLEOTIDE DESIGN AND/OR NUCLEIC ACID DETECTION

(75) Inventors: Christopher Wing Cheong Wong, Singapore (SG); Wing-Kin Sung, Singapore (SG); Charlie Lee, Singapore (SG); Lance David Miller, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1169 days.

(21) Appl. No.: 11/990,290

(22) PCT Filed: Aug. 8, 2006

(86) PCT No.: PCT/SG2006/000224
§ 371 (c)(1),
(2), (4) Date: Feb. 11, 2008

(87) PCT Pub. No.: WO2007/021250
PCT Pub. Date: Feb. 22, 2007

(65) Prior Publication Data
US 2009/0053708 A1    Feb. 26, 2009

Related U.S. Application Data

(63) Continuation-in-part of application No. 11/202,023, filed on Aug. 12, 2005, now abandoned.

(51) Int. Cl.
*G06F 19/00* (2006.01)
*G06F 15/00* (2006.01)
*G11C 17/00* (2006.01)
*C12N 15/11* (2006.01)

(52) U.S. Cl. ............... 702/20; 700/1; 365/94; 536/24.3

(58) Field of Classification Search .................. None
See application file for complete search history.

(56) References Cited

U.S. PATENT DOCUMENTS
2003/0236633 A1   12/2003  Mei et al.
2004/0259124 A1   12/2004  Bekiranov et al.

FOREIGN PATENT DOCUMENTS
GB    2 377 017 A    12/2002

OTHER PUBLICATIONS

Fielden et al. GP#: GenePix post-processing program for automated analysis of raw microarray data. Bioinformatics vol. 18, pp. 771-773 (2002).*
Lockhart et al. Expression monitoring by hybridization to high-density oligonucleotide arrays. Nature Biotechnology vol. 14, pp. 1675-1680 (1996).*
Wang et al. Microarray-based detection and genotyping of viral pathogens. Proceedings of the National Academy of Sciences USA vol. 99, pp. 15687-15692 (2002).*
Altschul S.F. et al., "Gapped BLAST and PSI-BLAST: a new generation of protein database search programs", 1997, 25: 3389-3402, Nucleic Acids Res.
Anderson T.W. and Darling D.A., "Asymptotic theory of certain goodness of fit criteria based on stochastic processes", 1952, 23:192-212, Annals of Mathematical Statistics.
Bodrossy L. and Sessitsch A., Oligonucleotide microarrays in microbial diagnostics, 2004, 7: 245-254, Curr Opin Microbiol.
Bohlander S.K. et al., "A method for the rapid sequence-independent amplification of microdissected chromosomal material", 1992, 13: 1322-1324, Genomics.
Bustin, S.A. and Nolan, T., "Pitfalls of quantitative real-time reverse-transcription polymerase chain reaction", 2004, 15:155-166, J Biomol Tech.
Deffernez C. et al., "Amplicon Sequencing and Improved Detection of Human Rhinovirus in Respiratory Samples", 2004, 42(7):3212-3218, J Clin Microbiol.
Fu J. et al., "Full-length cDNA sequence of dengue type 1 virus (Singapore strain S275/90)", 1992, 188:953-958, Virology.
Hamming R.W., "Error Detecting and Error Correcting Codes", 1950, 29: 147-160, Bell System Technical Journal.
International Human Genome Sequencing Consortium, "Initial sequencing and analysis of the human genome", 2001, 409:860-921, Nature.
Kane M.D. et al., "Assessment of the sensitivity and specificity of oligonucleotide (50mer) microarrays", 2000, 28: 4552-4557, Nucleic Acids Res.
Ksiazek T.G. et al., "A novel coronavirus associated with severe acute respiratory syndrome", 2003, 348:1953-1966, N Engl J Med.
Kullback S. and Leibler R.A., "On information and sufficiency", 1951, 22:79-86, Annals of Mathematical Statistics.
Li X. et al., "Selection of optimal oligonucleotide probes for microarrays using multiple criteria, global alignment and parameter estimation", 2005, 33:6114-6123, Nucl Acids Res.
Liu J. et al., "SARS transmission pattern in Singapore reassessed by viral sequence variation analysis", 2005, 2(2):162-168, PLoS Med.
Marra M.A. et al., "The Genome sequence of the SARS-associated coronavirus", 2003, 300:1399-1404, Science.
Maskos U. and Southern E.M. "A study of oligonucleotide reassociation using large arrays of oligonucleotides synthesised on a glass support", 1993, 21:4663-4669, Nucleic Acids Res.

(Continued)

*Primary Examiner* — John S Brusca
(74) *Attorney, Agent, or Firm* — Dickstein Shapiro LLP

(57) ABSTRACT

It is provided a method of designing at least one oligonucleotide for nucleic acid detection comprising the following steps in any order: (I) identifying and/or selecting region(s) of at least one target nucleic acid to be amplified, the region(s) having an efficiency of amplification (AE) higher than the average AE; and (II) designing at least one oligonucleotide capable of hybridizing to the selected region(s). It is also provided a method of detecting at least one target nucleic acid comprising the steps of: (i) providing at least one biological sample; (ii) amplifying nucleic acid(s) comprised in the biological sample; (iii) providing at least one oligonucleotide capable of hybridizing to at least one target nucleic acid, if present in the biological sample; and (iv) contacting the oligonucleotide(s) with the amplified nucleic acids and detecting the oligonucleotide(s) hybridized to the target nucleic acid(s). In particular, the method is for detecting the presence of at least one pathogen, for example a virus, in at least one human biological sample. The probes may be placed on a support, for example a microarray.

32 Claims, 20 Drawing Sheets

OTHER PUBLICATIONS

Moes E. et al., (2005) "A novel pancoronavirus RT-PCR assay: frequent detection of human coronavirus NL63 in children hospitalized with respiratory tract infections in Belgium", 2005. 5:6, BMC Infect Dis.

Nguyen H.K. and Southern E.M., "Minimising the secondary structure of DNA targets by incorporation of a modified deoxynucleoside: implications for nucleic acid analysis by hybridisation", 2000, 28: 3904-3909, Nucleic Acids Res.

Nuwaysir E.F. et al., "Gene expression analysis using oligonucleotide arrays produced by maskless photolithography", 2002, 12:1749-1755, Genome Res.

Pang X.L. et al., "Multiplex real time RT-PCR for the detection and quantitation of norovirus genogroups I and II in patients with acute gastroenteritis", 2005, 33:168-171, J Clin Virol.

Ratushna V.G. et al., "Secondary structure in the target as a confounding factor in synthetic oligomer microarray design", 2005, 6:31, BMC Genomics.

Ruan Y.J. et al., "Comparative full-length genome sequence analysis of 14 SARS coronavirus isolates and common mutations associated with putative origins of infection", 2003, 361:1779-1785, Lancet.

Santalucia, J., Jr. et al., "Improved nearest-neighbor parameters for predicting DNA duplex stability", 1996, 35:3555-3562, Biochemistry.

Smalling T.W. et al., "Molecular approaches to detecting herpes simplex virus and enteroviruses in the central nervous system", 2002, 40:2317-2322, J Clin Microbiol.

Stephens, M.A. "EDF Statistics for Goodness of Fit and Some Comparisons", 1974, 69:730-737, Journal of the American Statistical Association.

Striebel H.M. et al., "Virus diagnostics on microarrays", 2003, 4:401-415, Curr Pharm Biotechnol.

Urisman A. et al., "E-Predict: a computational strategy for species identification based on observed DNA microarray hybridization patterns", 2005, 6:R78, Genome Biol.

Vega V.B. et al., "Mutational dynamics of the SARS coronavirus in cell culture and human populations isolated in 2003", 2004, 4:32, BMC Infect Dis.

Vora G.J. et al., "Nucleic acid amplification strategies for DNA microarray-based pathogen detection", 2004, 70:3047-3054, Appl Environ Microbiol.

Wang D. et al., "Microarray-based detection and genotyping of viral pathogens", 2002, 99:15687-15692, Proc Natl Acad Sci U S A.

Wang D. et al., :Viral discovery and sequence recovery using DNA microarrays, 2003, 1:E2, PLoS Biol.

Wong C.W. et al., "Tracking the Evolution of the SARS Coronavirus Using High-Throughput, High-Density Resequencing Arrays", 2004, 14:398-405, Genome Res.

Wu, D.Y. et al., "The effect of temperature and oligonucleotide primer length on the specificity and efficiency of amplification by the polymerase chain reaction", 1991, 10:233-238, DNA Cell Biol.

Sung, W-K. et al., "Fast and Accurate Probe Selection Algorithm for Large Genomes," Proceedings IEEE Computer Society Bioinformatics Conference, 2003, 2: 65-74.

* cited by examiner

FIGURE 5

> Given PDC data $D$ with virus set $V$ and probe set $P$,
>
> Let $V' = \Phi$
>
> For every $v_a \in V$,
> - Compute one-tailed t-test with significance level 0.05 of probes in $v_a$
>
> If($p$-value of $t_a < 0.05$)
> - Accept if $KL(P_a \parallel P) \geq 0.1$; $V' = V' \cup \{ v_a \}$
> - Reject otherwise;
>
> Reject otherwise;
>
> Return $V'$

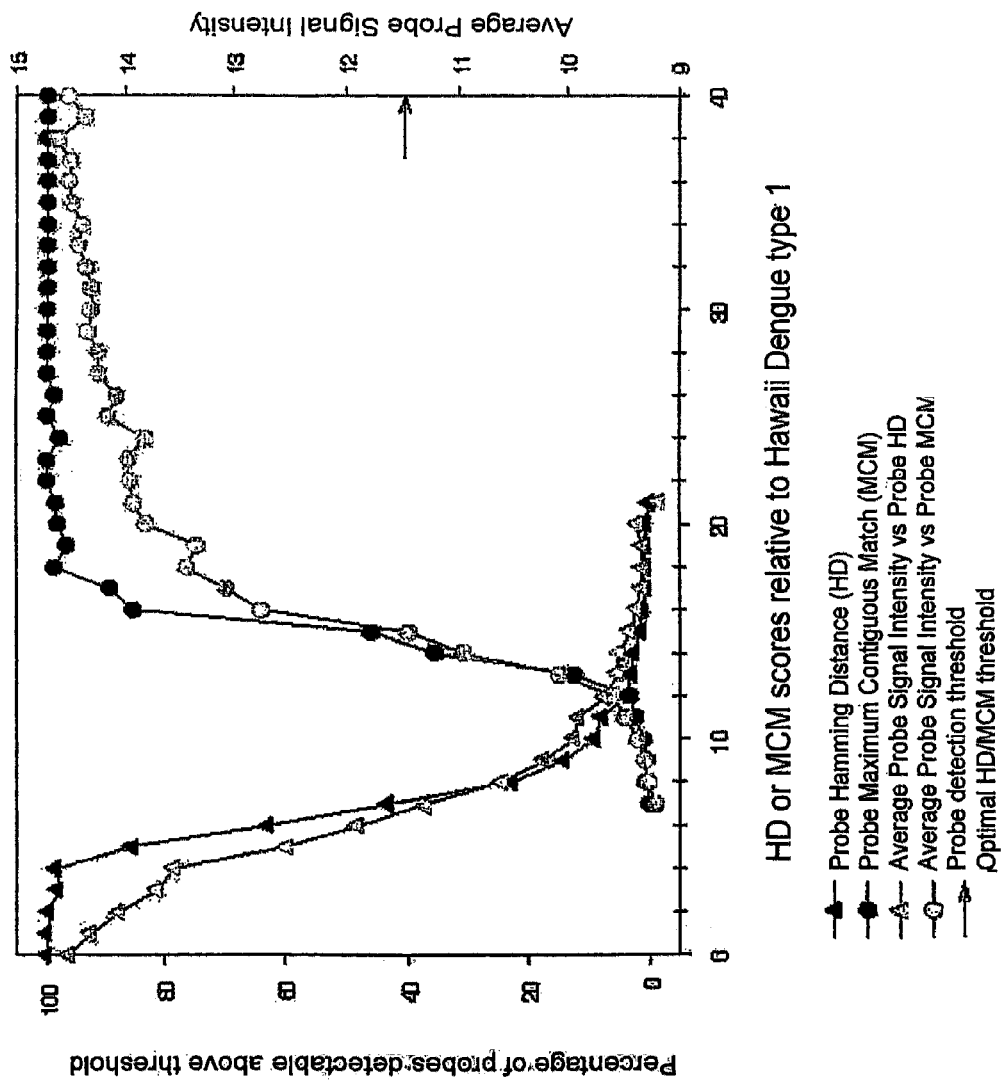

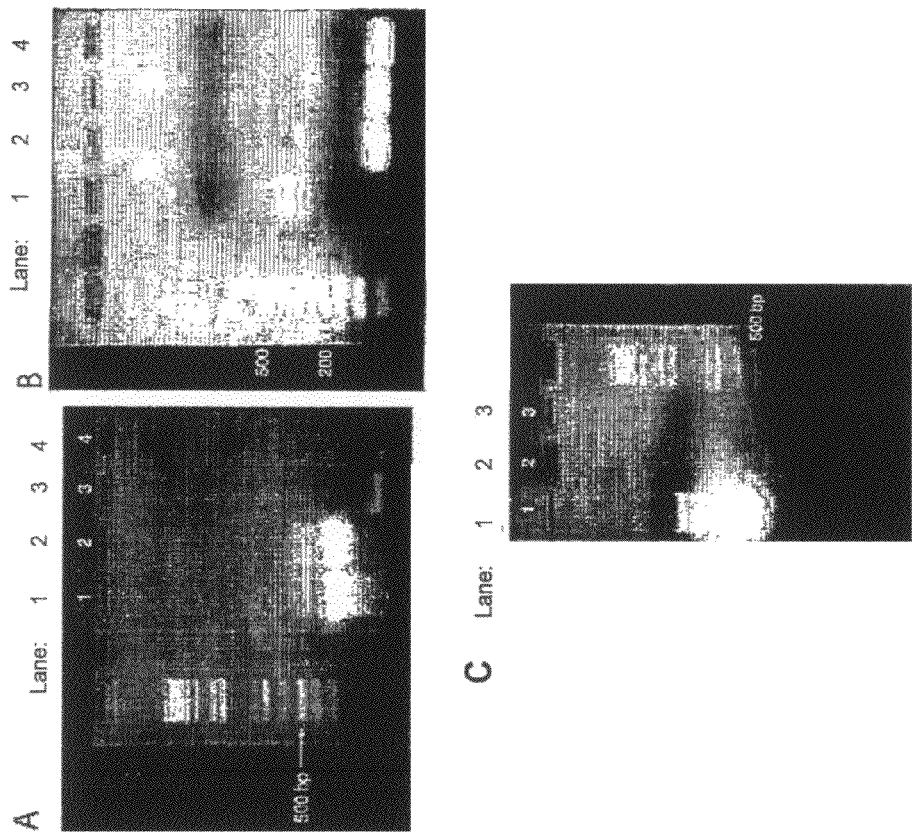
FIGURE 15(A,B,C)

SEQUENCE LISTING

```
<160> NUMBER OF SEQ ID NOS: 13

<210> SEQ ID NO 1
<211> LENGTH: 26
<212> TYPE: DNA
<213> ORGANISM: Artificial
<220> FEATURE:
<223> OTHER INFORMATION: Forward and/or reverse random primer
      (Figure 1A)
<220> FEATURE:
```

```
<221> NAME/KEY: misc_feature
<222> LOCATION: (18)..(26)
<223> OTHER INFORMATION: n is a, c, g, or t

<400> SEQUENCE: 1
gtttcccagt cacgatannn nnnnnn                                               26

<210> SEQ ID NO 2
<211> LENGTH: 26
<212> TYPE: DNA
<213> ORGANISM: Artificial
<220> FEATURE:
<223> OTHER INFORMATION: Random forward primer (Figure 1B)

<400> SEQUENCE: 2
gtttcccagt cacgatagca tgaggg                                               26

<210> SEQ ID NO 3
<211> LENGTH: 26
<212> TYPE: DNA
<213> ORGANISM: Artificial
<220> FEATURE:
<223> OTHER INFORMATION: Random reverse primer (Figure 1B)

<400> SEQUENCE: 3
gtttcccagt cacgatacga atagct                                               26

<210> SEQ ID NO 4
<211> LENGTH: 22
<212> TYPE: DNA
<213> ORGANISM: Artificial
<220> FEATURE:
<223> OTHER INFORMATION: Fragment of virus sequence (upper leftmost
      strand of virus sequence in Figure 1B)

<400> SEQUENCE: 4
acgatatccg cgaatagcta ga                                                   22

<210> SEQ ID NO 5
<211> LENGTH: 23
<212> TYPE: DNA
<213> ORGANISM: Artificial
<220> FEATURE:
<223> OTHER INFORMATION: Fragment of virus sequence (upper rightmost
      strand of virus sequence in Figure 1B)

<400> SEQUENCE: 5
catccctcat gcatggggca att                                                  23

<210> SEQ ID NO 6
<211> LENGTH: 22
<212> TYPE: DNA
<213> ORGANISM: Artificial
<220> FEATURE:
<223> OTHER INFORMATION: Fragment of virus sequence (lower leftmost
      strand of virus sequence in Figure 1B)

<400> SEQUENCE: 6
tgctataggc gcttatcgat ct                                                   22

<210> SEQ ID NO 7
<211> LENGTH: 23
<212> TYPE: DNA
<213> ORGANISM: Artificial
<220> FEATURE:
<223> OTHER INFORMATION: Fragment of virus sequence (lower rightmost
      strand of virus sequence in Figure 1B)
```

-continued

```
<400> SEQUENCE: 7
gtagggagta cgtaccccgt taa                                          23

<210> SEQ ID NO 8
<211> LENGTH: 17
<212> TYPE: DNA
<213> ORGANISM: Artificial
<220> FEATURE:
<223> OTHER INFORMATION: Random Primer Tag (top strand Figure 1C and 1D)

<400> SEQUENCE: 8
gtttcccagt cacgata                                                 17

<210> SEQ ID NO 9
<211> LENGTH: 17
<212> TYPE: DNA
<213> ORGANISM: Artificial
<220> FEATURE:
<223> OTHER INFORMATION: Random Primer Tag (bottom strand Figure 1C
      and 1D)

<400> SEQUENCE: 9
caaagggtca gtgctat                                                 17

<210> SEQ ID NO 10
<211> LENGTH: 17
<212> TYPE: DNA
<213> ORGANISM: Artificial
<220> FEATURE:
<223> OTHER INFORMATION: Primer A1 (Figure 13)

<400> SEQUENCE: 10
gtttcccagt cacgata                                                 17

<210> SEQ ID NO 11
<211> LENGTH: 17
<212> TYPE: DNA
<213> ORGANISM: Artificial
<220> FEATURE:
<223> OTHER INFORMATION: Primer A2 (Figure 13)

<400> SEQUENCE: 11
gatgagggaa gatgggg                                                 17

<210> SEQ ID NO 12
<211> LENGTH: 17
<212> TYPE: DNA
<213> ORGANISM: Artificial
<220> FEATURE:
<223> OTHER INFORMATION: Primer A3 (Figure 13)

<400> SEQUENCE: 12
ctcatgcacg acccaaa                                                 17

<210> SEQ ID NO 13
<211> LENGTH: 17
<212> TYPE: DNA
<213> ORGANISM: Artificial
<220> FEATURE:
<223> OTHER INFORMATION: Primer A4 (Figure 13)

<400> SEQUENCE: 13
agatccattc cacccca                                                 17
```

METHOD AND/OR APPARATUS OF OLIGONUCLEOTIDE DESIGN AND/OR NUCLEIC ACID DETECTION

This is a 371 of International Application No. PCT/SG2006/000224, filed on Aug. 8, 2006, and a continuation-in-part of prior Application Ser. No. 11/202,023, filed on Aug. 12, 2005, now abandoned.

FIELD OF THE INVENTION

The present invention relates to the field of oligonucleotide design and/or nucleic acid detection. The method, apparatus and/or product according to the invention may be used for the detection of pathogens, for example for the detection of viruses.

BACKGROUND OF THE INVENTION

The accurate and rapid detection of viral and bacterial pathogens in human patients and populations is of critical medical and epidemiologic importance. Historically, diagnostic techniques have relied on cell culture passaging and various immunological assays or staining procedures. Accurate and sensitive detection of infectious disease agents is still difficult today, despite a long history of progress in this area. Traditional methods of culture and antibody-based detection still play a central role in microbiological laboratories despite the problems of the delay between disease presentation and diagnosis, and the limited number of organisms that can be detected by these approaches. Faster diagnosis of infections would reduce morbidity and mortality, for example, through the earlier implementation of appropriate antimicrobial treatment. During the past few-decades, various methods have been proposed to achieve this; with those based on nucleic acid detection, including PCR and microarray-based techniques, seeming the most promising. In particular, PCR-based assays have been implemented, allowing for more rapid diagnosis of suspected pathogens with higher degree of sensitivity of detection. In clinical practice, however, the etiologic agent often remains unidentified, eluding detection in myriad ways. For example, some viruses are not amenable to culturing. At other times, a patient's sample may be of too poor quality or of insufficient titre for pathogen detection by conventional techniques. Moreover, both PCR- and antibody-based approaches may fail to recognize suspected pathogens simply due to natural genetic diversification resulting in alterations of PCR primer binding sites and antigenic drift.

DNA and oligonucleotide microarrays with the potential to detect multiple pathogens in parallel have been described (Wang et al. 2002; Urisman et al. 2005). However, unresolved technical questions prevent their routine use in the clinical setting. For example, how does one select the most informative probes for comprising a pathogen signature in light of amplification and cross-hybridization artifacts? What levels of fluorescent signal and signature probe involvement constitute a detected pathogen? What is the accuracy and sensitivity of an optimized detection algorithm? (Striebel et al. 2003; Bodrossy and Sessitsch, 2004; Vora et al. 2004).

Accordingly, there is a need in this field of technology for alternative and improved methods of detection of nucleic acids. In particular, there is a need for alternative and/or improved diagnostic methods for the detection of pathogens.

SUMMARY OF THE INVENTION

The present invention addresses the problems above, and in particular provides a method, apparatus and/or product of oligonucleotide design. In particular, there is provided a method, apparatus and/or product of oligonucleotide probe and/or primer design. There is also provided a method, apparatus and/or product of nucleic acid detection.

According to a first aspect, the present invention provides a method of designing at least one oligonucleotide for nucleic acid detection comprising the following steps in any order:
(I) identifying and/or selecting at least one region of at least one target nucleic acid to be amplified, the region(s) having an efficiency of amplification (AE) higher than the average AE; and
(II) designing at least one oligonucleotide capable of hybridizing to the selected region(s).

The at least one oligonucleotide may be at least one probe and/or primer.

In particular, in step (I) a score of AE is determined for every position i on the length of the target nucleic acid(s) or of at least one region thereof and subsequently, an average AE score is obtained. Those regions showing an AE score higher than the average may be selected as the region(s) of the target nucleic acid to be amplified. In particular, the AE of the selected region(s) may be calculated as the Amplification Efficiency Score (AES), which is the probability that a forward primer $r_i$ can bind to a position i and a reverse primer $r_j$ can bind at a position j of the target nucleic acid, and $|i-j|$ is the region of the target nucleic acid desired to be amplified. In particular, the region $|i-j|$ may be $\leq 10000$ bp, more in particular $\leq 5000$ bp, or $\leq 1000$ bp, for example $\leq 500$ bp. In particular, the forward and reverse primers may be random primers.

According to another aspect, the step (I) comprises determining the effect of geometrical amplification bias for every position of a target nucleic acid, and selecting at least one region(s) to be amplified as the region(s) having an efficiency of amplification (AE) higher than the average AE. For example, the geometrical amplification bias is the PCR bias.

The step (II) of designing at least one oligonucleotide capable of hybridizing to the region(s) selected in step (I) may be carried out according to any oligonucleotide designing technique known in the art. In particular, the oligonucleotide(s) capable of hybridizing to the selected region(s) may be selected and designed according to at least one of the following criteria:
(a) the selected oligonucleotide(s) has a CG-content from 40% to 60%;
(b) the oligonucleotide(s) is selected by having the highest free energy computed based on Nearest-Neighbor model;
(c) given oligonucleotide $s_a$ and oligonucleotide $s_b$ substrings of target nucleic acids $v_a$ and $v_b$, $s_a$ is selected based on the hamming distance between $s_a$ and any length-m substring $s_b$ and/or on the longest common substring of $s_a$ and oligonucleotide $s_b$;
(d) for any oligonucleotide $s_a$ of length-m specific for the target nucleic acid $v_a$, the oligonucleotide $s_a$ is selected if it does not have any hits with any region of a nucleic acid different from the target nucleic acid, and if the oligonucleotide $s_a$ length-m has hits with the nucleic acid different from the target nucleic acid, the oligonucleotide $s_a$ length-m with the smallest maximum alignment length and/or with the least number of hits is selected; and
(e) a oligonucleotide $p_i$ at position i of a target nucleic acid is selected if $p_i$ is predicted to hybridize to the position i of the amplified target nucleic acid.

In particular, the oligonucleotide may be a probe and/or primer.

Accordingly, two or more of the criteria indicated above may be used for designing the oligonucleotides(s). For example, the oligonucleotide(s) may be designed by applying all criteria (a) to (e). Other criteria not explicitly mentioned herein but which are within the knowledge of a skilled person in the art may also be used.

In particular, under the criterion (e), a oligonucleotide $p_i$ at position i of a target nucleic acid $v_a$ is selected if $P(p_i|v_a) \geqslant \lambda$, wherein $\lambda$ is 0.5 and $P(p_i|v_a)$ is the probability that $p_i$ hybridizes to the position i of the target nucleic acid $v_a$. More in particular, $\lambda$ is 0.8.

In particular, $$P(p_i | v_a) \approx P(X \leq x_i) = \frac{c_i}{k},$$

wherein X is the random variable representing the amplification efficiency score (AES) values of all oligonucleotides of $v_a$, k is the number of oligonucleotides in $v_a$, and $c_i$ is the number of oligonucleotides whose AES values are $\leq x_i$.

According to another aspect of the invention, the method of designing the oligonucleotide(s) as described above further comprises a step of preparing the selected and designed oligonucleotide(s). The oligonucleotide, which may be at least one probe and/or primer, may be prepared according to any standard method known in the art. For example, by chemical synthesis or photolithography.

According to another aspect, the present invention provides a method of detecting at least one target nucleic acid comprising the steps of:
(i) providing at least one biological sample;
(ii) amplifying nucleic acid(s) comprised in the biological sample;
(iii) providing at least one oligonucleotide capable of hybridising to at least one target nucleic acid, if present in the biological sample, wherein the oligonucleotide(s) is designed and/or prepared by using a method according to any aspect of the invention described herein; and
(iv) contacting the oligonucleotide(s) with the amplified nucleic acids and/or detecting the oligonucleotide(s) hybridised to the target nucleic acid(s).

In particular, the oligonucleotide is a probe.

The amplification step (ii) may be carried out in the presence of random primers. For example, the amplification step (ii) may be carried out in the presence of at least one random forward primer, at least one random reverse primer and/or more than two random primers. Any amplification method known in the art may be used. For example, the amplification method is a RT-PCR.

In particular, a forward random primer binding to position i and a reverse random primer binding to position j of a target nucleic acid $v_a$ are selected among primers having an amplification efficiency score ($AES_i$) for every position i of a target nucleic acid $v_a$ of:

$$AES_i = \sum_{j=i-Z}^{i} \left\{ P^f(j) \times \sum_{k=\max(i+1, j+500)}^{j+Z} P^r(k) \right\},$$

wherein $$\sum_{k=\max(i+1, j+500)}^{j+Z} P^r(k) = P^r(i+1) + P^r(i+2) + \ldots P^r(j+Z),$$

$P^f(i)$ and $P^r(i)$ are the probability that a random primer $r_i$ can bind to position i of $v_a$ as forward primer and reverse primer, respectively, and $Z \leq 10000$ bp is the region of $v_a$ desired to be amplified. More in particular, Z may be $\leq 5000$ bp, $\leq 1000$ bp, or $\leq 500$ bp.

The amplification step may comprise forward and reverse primers, and each of the forward and reverse primers may comprise, in a 5'-3' orientation, a fixed primer header and a variable primer tail, and wherein at least the variable tail hybridizes to a portion of the target nucleic acid $v_a$. In particular, the amplification step may comprise forward and/or reverse random primers having the nucleotide sequence of SEQ ID NO:1 or a variant or derivative thereof.

The biological sample may be any sample taken from a mammal, for example from a human being. The biological sample may be tissue, sera, nasal pharyngeal washes, saliva, any other body fluid, blood, urine, stool, and the like. The biological sample may be treated to free the nucleic acid comprised in the biological sample before carrying out the amplification step. The target nucleic acid may be any nucleic acid which is intended to be detected. The target nucleic acid to be detected may be at least a nucleic acid exogenous to the nucleic acid of the biological sample. Accordingly, if the biological sample is from a human, the exogenous target nucleic acid to be detected (if present in the biological sample) is a nucleic acid which is not from human origin.

According to an aspect of the invention, the target nucleic acid to be detected is at least a pathogen genome or fragment thereof. The pathogen nucleic acid may be at least a nucleic acid from a virus, a parasite, or bacterium, or a fragment thereof.

Accordingly, the invention provides a method of detection of at least a target nucleic acid, if present, in a biological sample. The method may be a diagnostic method for the detection of the presence of a pathogen in the biological sample. For example, if the biological sample is obtained from a human being, the target nucleic acid, if present in the biological sample, is not from human.

The oligonucleotide(s) designed and/or prepared according to any method of the present invention may be used in solution or may be placed on an insoluble support. For example, the oligonucleotide probe(s) may be applied, spotted or printed on an insoluble support according to any technique known in the art. The support may be a microarray, a biochip, a membrane/synthetic surface, solid support or a gel.

The probes are then contacted with the nucleic acid(s) of the biological sample, and, if present, the target nucleic acid(s) and the probe(s) hybridize, and the presence of the target nucleic acid is detected. In particular, in the detection step (iv), the mean of the signal intensities of the probes which hybridize to $v_a$ is statistically higher than the mean of the probes $\notin v_a$, thereby indicating the presence of $v_a$ in the biological sample.

More in particular, in the detection step (iv), the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$ in the biological sample.

For example, in the detection step (iv), at least one target nucleic acid in a biological sample is detected if the density distribution of its probe signal intensities is not normal, i.e. more positively skewed, given by Anderson-Darling test value≦0.05 and/or a value of t-test≦0.1 and/or a value of Weighted Kullback-Leibler divergence of ≧1.0, preferably ≧5.0., In particular, the t-test value is ≦0.05.

More in particular, the method of the detection step (iv), further comprises evaluating the probe signal intensity of probe(s) in each pathogen specific signature probe set (SPS) for the target nucleic acid(s) $v_a$ by calculating the distribution of Weighted Kullback-Leibler (WKL) divergences scores:

$$WKL(P_a | \overline{P_a}) = \sum_{j=0}^{k-1} \frac{Q_a(j)\log\left(\frac{Q_a(j)}{Q_{\overline{a}}(j)}\right)}{\sqrt{Q_{\overline{a}}(j)[1 - Q_{\overline{a}}(j)]}}$$

where $Q_a(j)$ is the cumulative distribution function of the signal intensities of the probes in $P_a$ found in bin $b_j$; $Q_{\overline{a}}(j)$ is the cumulative distribution function of the signal intensities of the probes in $\overline{P_a}$ found in bin $b_j$. $Q_{\overline{a}}(j)$ is the cumulative distribution function of the signal intensities of the probes in $\overline{P_a}$ found in bin $b_j$. $P_a$ is the set of probes of a virus $v_a$ and $\overline{P_a} = P - P_a$.

For example, each signature probe set (SPS) which represents the absence of target nucleic acid(s) $v_a$ has a normally distributed signal intensity (assessed by Anderson-Darling test value≦0.05) and/or a Weighted Kullback-Leibler (WKL) divergence score of WKL<5. Each signature probe set (SPS) which represents the presence of at least one target nucleic acid $v_a$ has a positively skewed signal intensity distribution and/or a Weighted Kullback-Leibler (WKL) divergence score of WKL>5.

The method may further comprise performing Anderson-Darling test on the distribution of WKL score(s), wherein a result of P>0.05 thereby indicates the absence of target nucleic acid(s) $v_a$, or wherein a result of P<0.05 thereby indicates the presence of target nucleic acid(s) $v_a$. Additionally, a further Anderson-Darling test may be performed thereby indicating the presence of further co-infecting target nucleic acid(s). According to another aspect, the present invention provides a method of determining the presence of a target nucleic acid $v_a$ comprising detecting the hybridization of at least one oligonucleotide probe (the probe being selected and designed according to any known method in the art and not necessary limited to the methods according to the present invention) to at least one target nucleic acid $v_a$ is statistically higher than the mean of the probes $\notin v_a$, thereby indicating the presence of $v_a$. In particular, the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$. More in particular, the presence of a target nucleic acid in a biological sample is given by a value of t-test≦0.1 and/or Anderson-Darling test value≦0.05 and/or a value of Weighted Kullback-Leibler divergence of ≧1.0, preferably ≧5.0. For example, the t-test value may be ≦0.05.

According to another aspect, the present invention provides a method of detecting at least one target nucleic acid, comprising the steps of:
   (i) providing at least one biological sample;
   (ii) amplifying at least one nucleic acid(s) comprised in the biological sample;
   (iii) providing at least one oligonucleotide capable of hybridizing to at least one target nucleic acid, if present in the biological sample; and
   (iv) contacting the oligonucleotide(s) with the amplified nucleic acids and detecting the oligonucleotide(s) hybridized to the target nucleic acid(s), wherein the mean of the signal intensities of the oligonucleotide(s) which hybridize to $v_a$ is statistically higher than the mean of the oligonucleotide(s) $\notin v_a$, thereby indicating the presence of $v_a$ in the biological sample.

In particular, the oligonucleotide is an oligonucleotide probe.

In step (iv) the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$ in the biological sample. In particular, in step (iv) the presence of at least one target nucleic acid in a biological sample is given by a value of t-test≦0.1 and/or Anderson-Darling test value≦0.05 and/or a value of Weighted Kullback-Leibler divergence of ≧1.0, preferably ≧5.0. The t-test value may be ≦0.05. The nucleic acid to be detected is nucleic acid exogenous to the nucleic acid of the biological sample. The target nucleic acid to be detected may be at least one pathogen genome or fragment thereof. The pathogen nucleic acid may be at least one nucleic acid from a virus, a parasite, or bacterium, or a fragment thereof. In particular, when the sample is obtained from a human being, the target nucleic acid, if present in the biological sample, is not from the human genome. The probes may be placed on an insoluble support. The support may be a microarray, a biochip, or a membrane/synthetic surface.

The present invention provides an apparatus of the invention, comprising an apparatus for performing the methods according to the invention. In particular, the apparatus may be for designing oligonucleotide(s) for nucleic acid detection and/or amplification, the apparatus being configured to identify and/or select at least one region(s) of at least one target nucleic acid to be amplified, the region(s) having an efficiency of amplification (AE) higher than the average AE; and design at least one oligonucleotide(s) capable of hybridizing to the identified and/or selected region(s). More in particular, the apparatus may be configured to detect at least one target nucleic acid comprising any one of the steps of: providing at least one biological sample; amplifying nucleic acid(s) comprised in the biological sample, providing at least one oligonucleotide capable of hybridizing to at least one target nucleic acid, if present in the biological sample, wherein the oligonucleotide(s) is designed and/or prepared according to the apparatus being configured according to the invention; and contacting the oligonucleotide(s) with the amplified nucleic acids and/or detecting the oligonucleotide(s) hybridized to the target nucleic acid(s).

The present invention also provides at least one computer program product configured for performing the method according to the invention. There is also provided at least one electronic storage medium storing the configuration of the apparatus according to the invention. According to one aspect, the invention provides a removable electronic storage medium comprising a software configured to perform the method(s) according to the invention. In particular, the removable electronic storage medium may comprise a software configured to determine the WKL divergence score and/or Anderson-Darling test for designing at least one oligonucleotide probe and/or primer, and/or detecting at least one target nucleic acid. More in particular, the removable electronic storage comprising a software configuration may comprise the WKL, Anderson-Darling test, the designing of probe(s) and/or the detecting of target nucleic acid(s) as defined according to the invention. Accordingly, there is also provided a software configured as described above.

A: Reverse transcription (RT). Primer binds to template.

B: Tagged RT products are generated (in detail with hypothetical viral sequence template and hypothetical specific random primer).

C: Second strand synthesis is completed incorporating tags.

D: Amplification of tagged RT product using PCR Primer GTTTCCCAGTCACGATA (SEQ ID NO:8).

Figure 2:
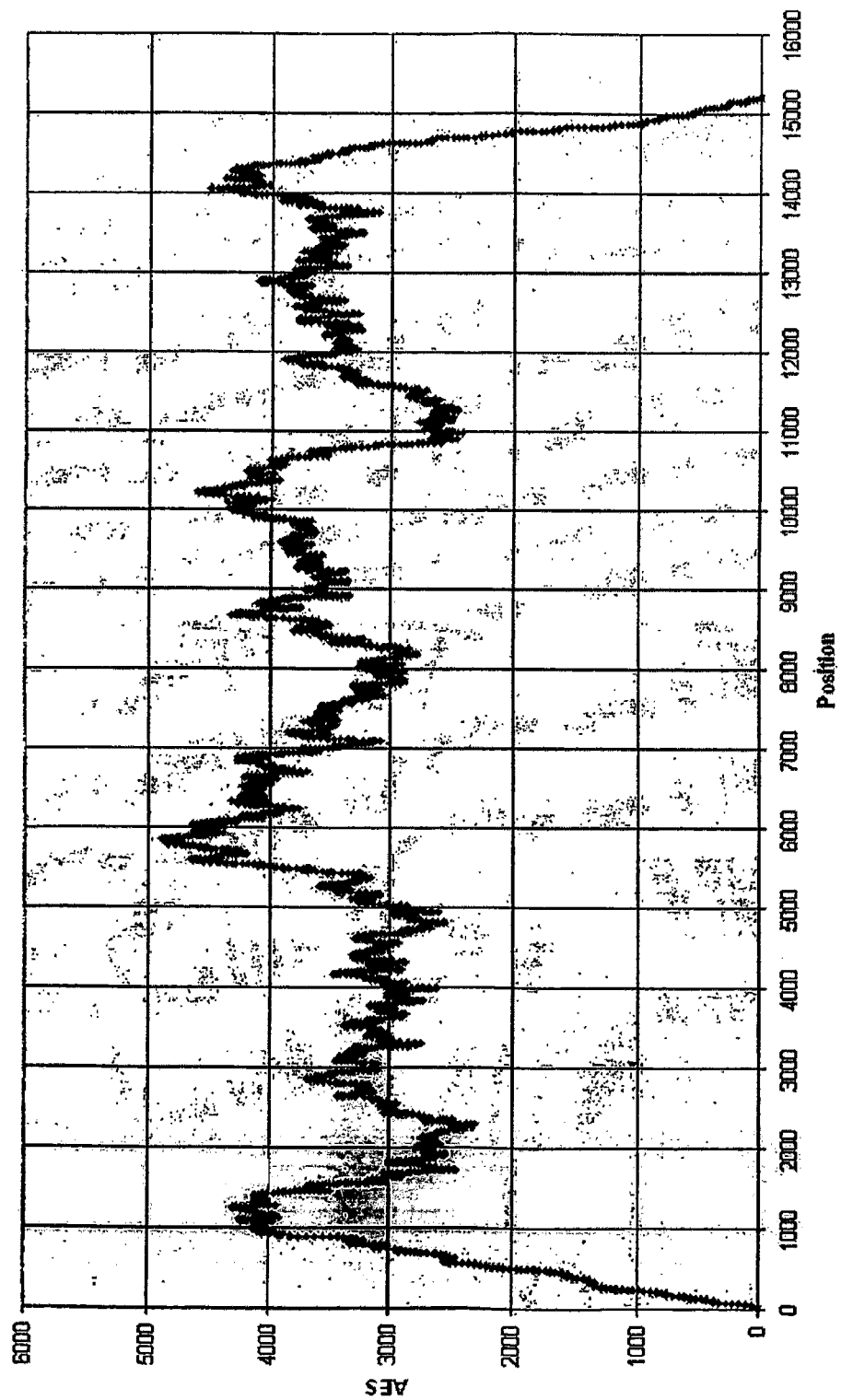

FIG. 2 shows an Amplification Efficiency Scoring (AES) Map for the RSV B genome.

Figure 3:
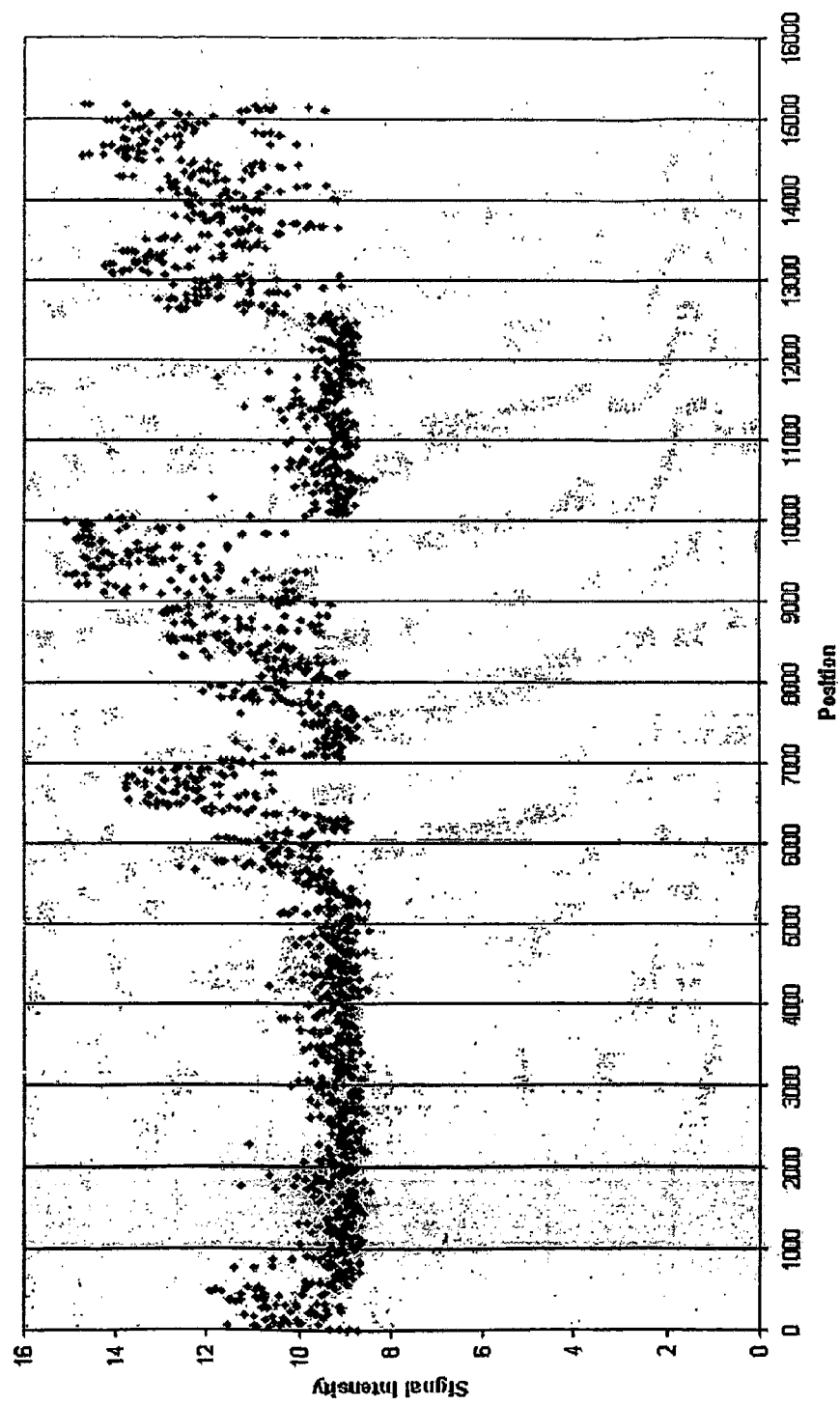

FIG. 3 shows oligonucleotide probe signal intensities for 1 experiment for RSV B.

Figure 4A:
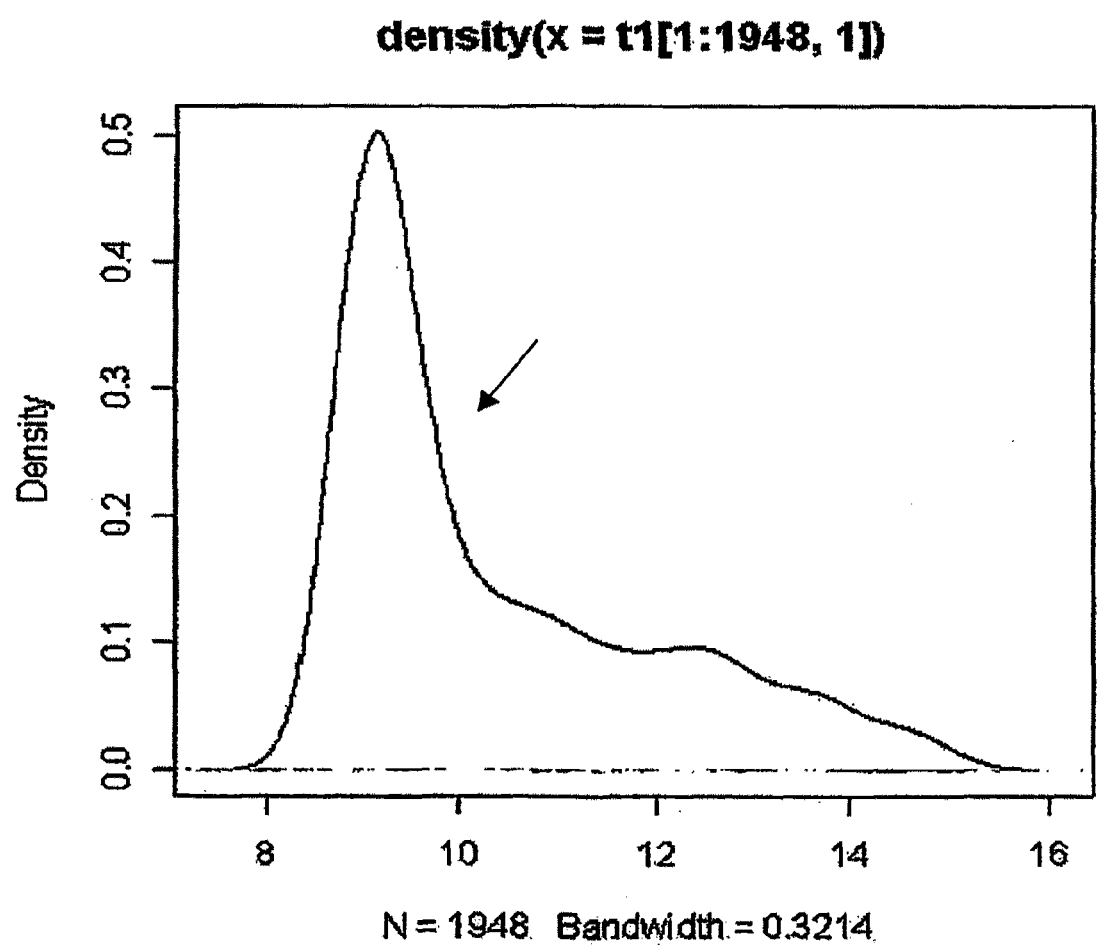
Figure 4B:
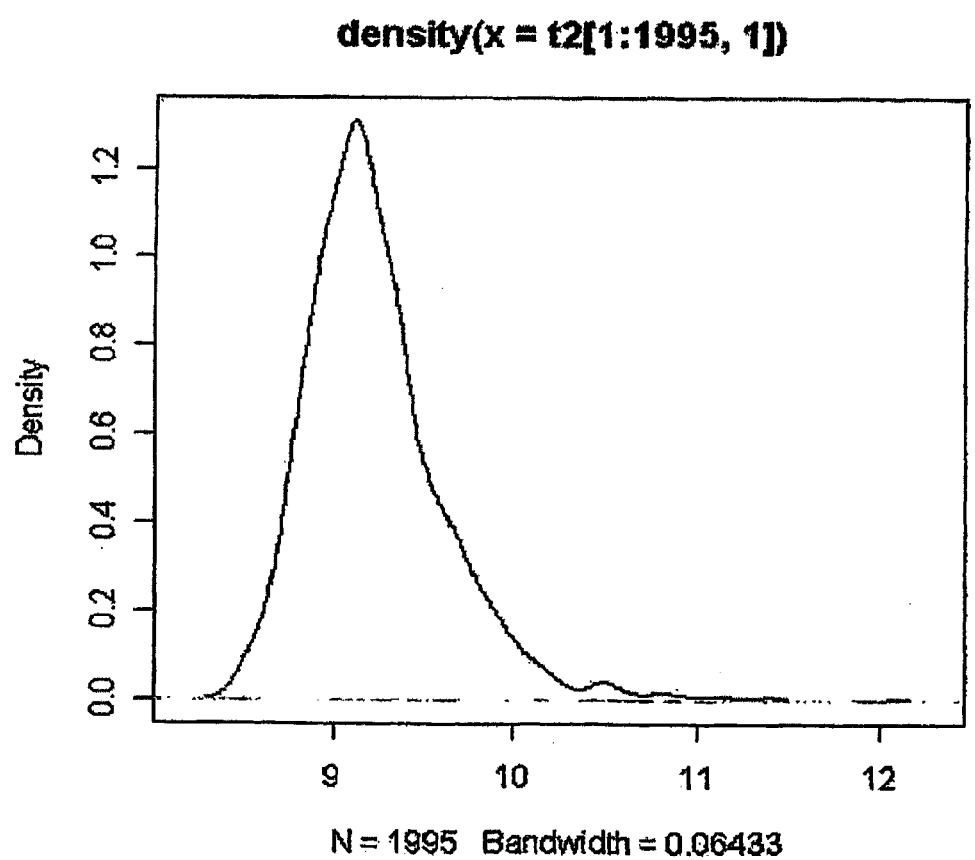

FIGS. 4(A, B). FIG. 4A shows the density distribution of signal intensities of a virus that is the sample tested. An arrow indicates the positive skewness of the distribution. This indicates that although there is noise, there is significant amount of real signals as well. FIG. 4B shows the density distribution of signal intensities of a virus not in the sample. It is noise dominant.

FIG. 5 shows an analysis framework of pathogen detection chip data.

Figure 6:
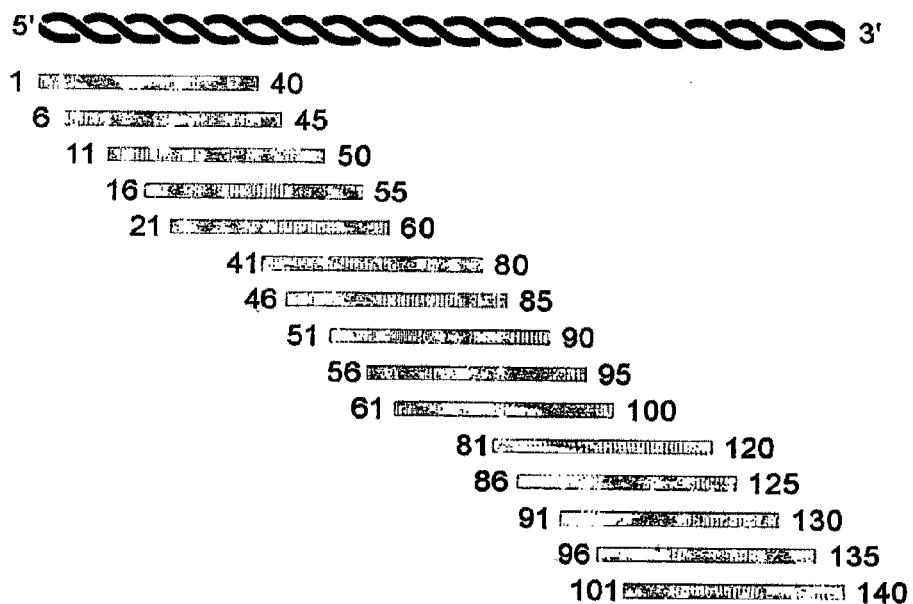

FIG. 6. Oligonucleotide probe design schema. This illustrates the tiling probes created across the genome of NC_001781 Human respiratory syncytial virus (RSV). The numbers represent the start and end positions of each probe. 1948 probes were synthesized to cover the entire 15225 bp RSV genome. This process was repeated for the remaining 34 viral genomes.

FIG. 7(A,B,C) Key to labels of microarray bars:

| Virus family | Virus genus/species |
|---|---|
| Orthomyxoviridae | Sars Sin2500 |
| | OC41 |
| | 229E |
| Coronaviridae | Flu A |
| | Flu B |
| Picornaviridae | Entero D |
| | Entero C |
| | Echo 1 |
| | Entero B |
| | Entero A |
| | Rhino 89 |
| | Rhino B |
| | Hep A |
| | Foot & mouth C |
| Bunyaviridae | Hantaan |
| | Sin Nombre |
| Flaviviridae | West Nile |
| | Jap enceph |
| | Dengue 3 |
| | Dengue 1 |
| | Dengue 2 |
| | Dengue 4 |
| | Yellow fever |
| Paramyxoviridae | Paraflu 1 |
| | Paraflu 3 |
| | Nipah |
| | Paraflu 2 |
| | Newcastle |
| | RSV (B1) |
| | Metapneumovirus |
| Others | HPV type 10 |
| | HIV 1 |
| | Hep B |
| | Rubella |
| | LCMV-S |
| | LCMV-L |
| | PMMV |
| | Human controls |

RNA isolated from SARS Sin850-infected cell line (A) or Dengue I-infected cell line (B) was hybridized onto the pathogen microarray following SARS-specific or Dengue I-specific RT-PCR, respectively. SARS cross-hybridized (shown in black colour) to other coronaviridae genomes, particularly to the highly conserved middle portion of the genome (Ruan et al. 2003). Dengue I cross-hybridized to probes derived from flaviviridae and other genomes based on their sequence similarity. By examining the Hamming Distance (HD) and Maximum Contiguous Match (MCM) scores, we established thresholds to predict whether cross-hybridization would occur and utilized this information to generate in silico hybridization signatures. (C) RNA isolated from a clinical patient diagnosed with RSV was amplified using random RT-PCR and hybridized onto the pathogen microarray.

FIG. 8 Relationship between probe Hamming Distance (HD), probe Maximum Contiguous Match (MCM) and probe Signal Intensity. Average probe signal intensity decreases as HD increases and MCM decreases. This correlates with a reduction in the percentage of detectable probes (signal intensity>mean+2 SD). At the optimal cross-hybridization thresholds HD$\leq$4 or MCM$\geq$18 (shaded), >98% of probes can be detected. At HD=5 or MCM=17, the detection rate falls to 85%.

FIG. 9(A, B) RNA isolated from a RSV-infected patient was hybridized onto a pathogen detection array. (A) Distribution of probe signal intensities all 53,555 probes show a normal distribution (grey solid line). Non-RSV probes, when examined on a genome-specific level, e.g. parainfluenza-1 (grey dotted line), also show a normal distribution. Signal intensity of RSV-specific probes have a positive skew, with higher signal intensities in the tail of the distribution (black solid line). (B) Distribution frequency of WKL scores for the 35 SPS with majority ranging between −5 and 3. However the WKL score for the RSV genome is 17, so the distribution is not normal (P<0.05 by Anderson Darling test). Excluding the outlier genome results in a normal distribution. From this computation, we conclude that RSV is present in the hybridized sample.

Figure 10:
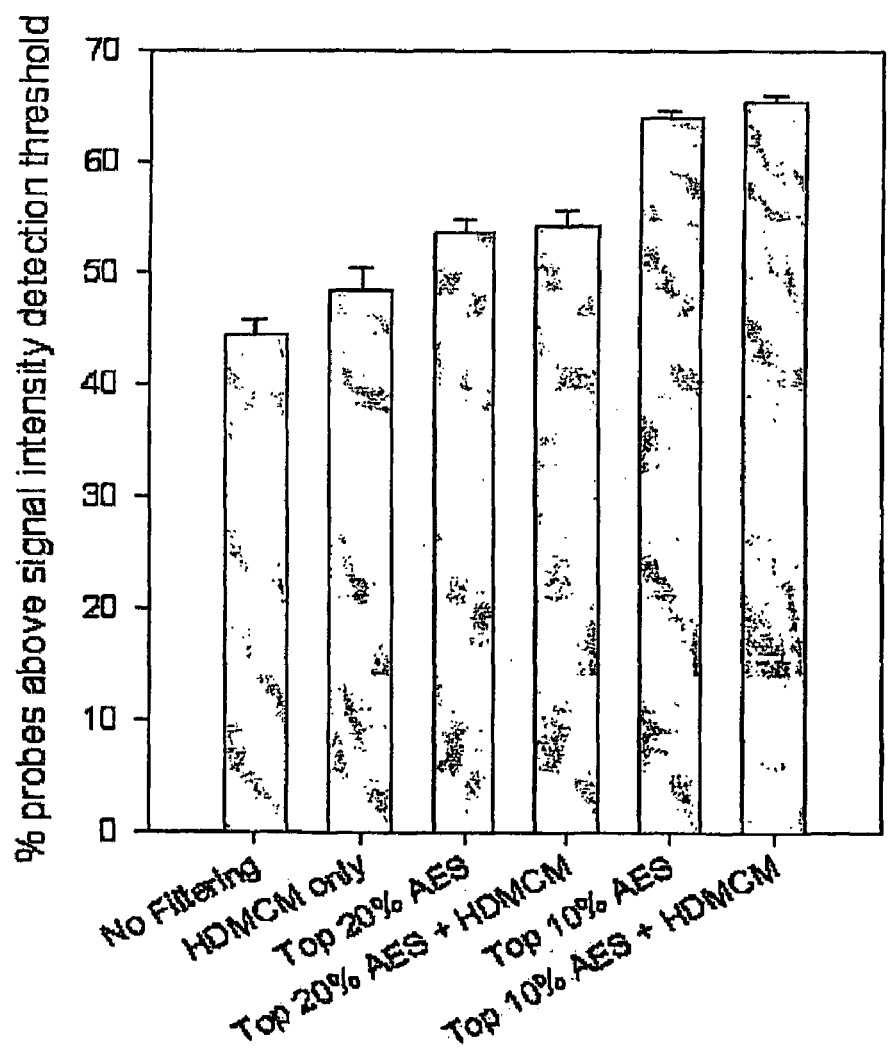

FIG. 10 AES is indicative of probe amplification efficiency. Higher proportion of probes with high AES are detectable above signal intensity thresholds over 5 experiments.

Figure 11:
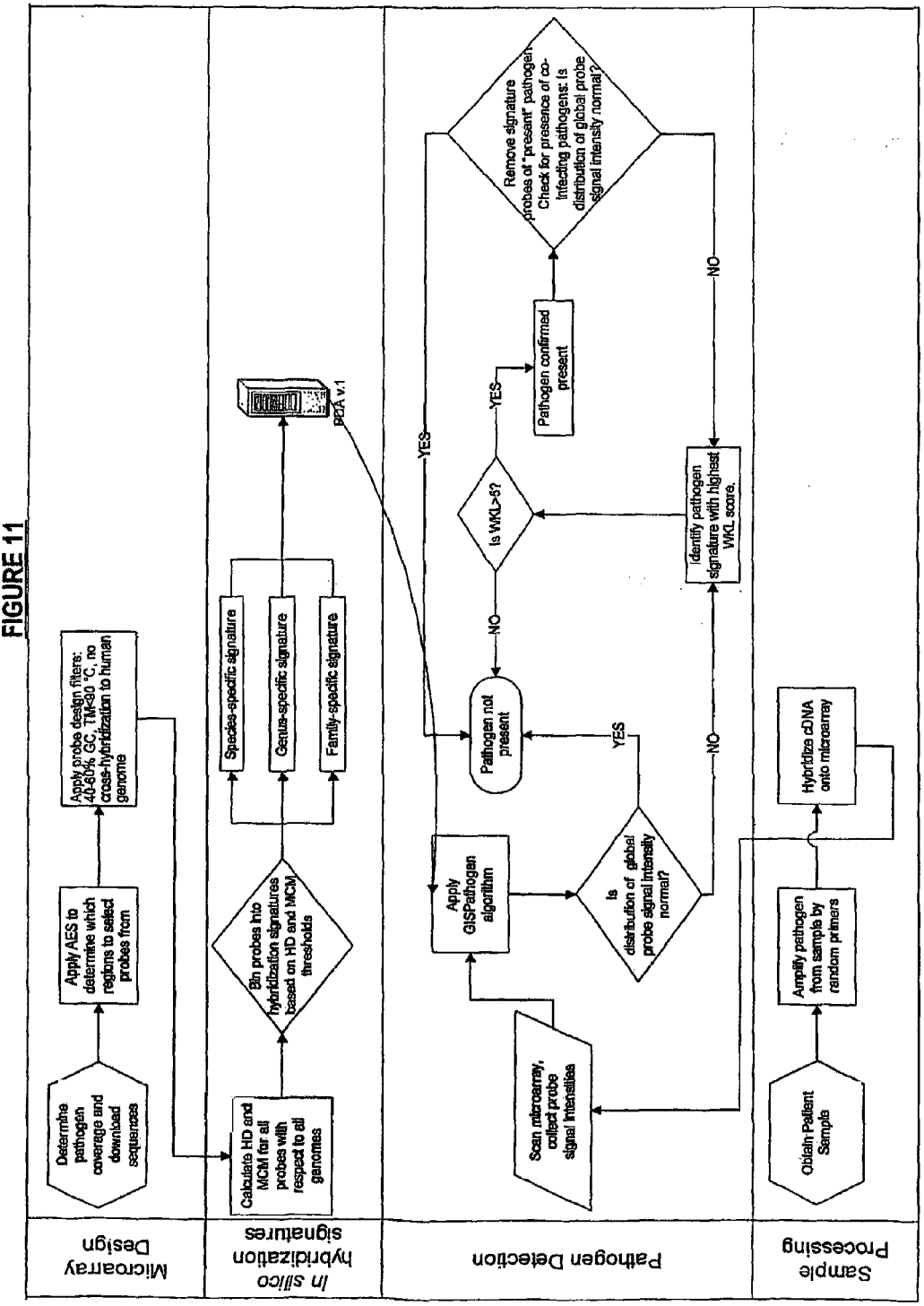

FIG. 11 Schema showing the processes necessary for pathogen detection using microarray.

Figure 12:
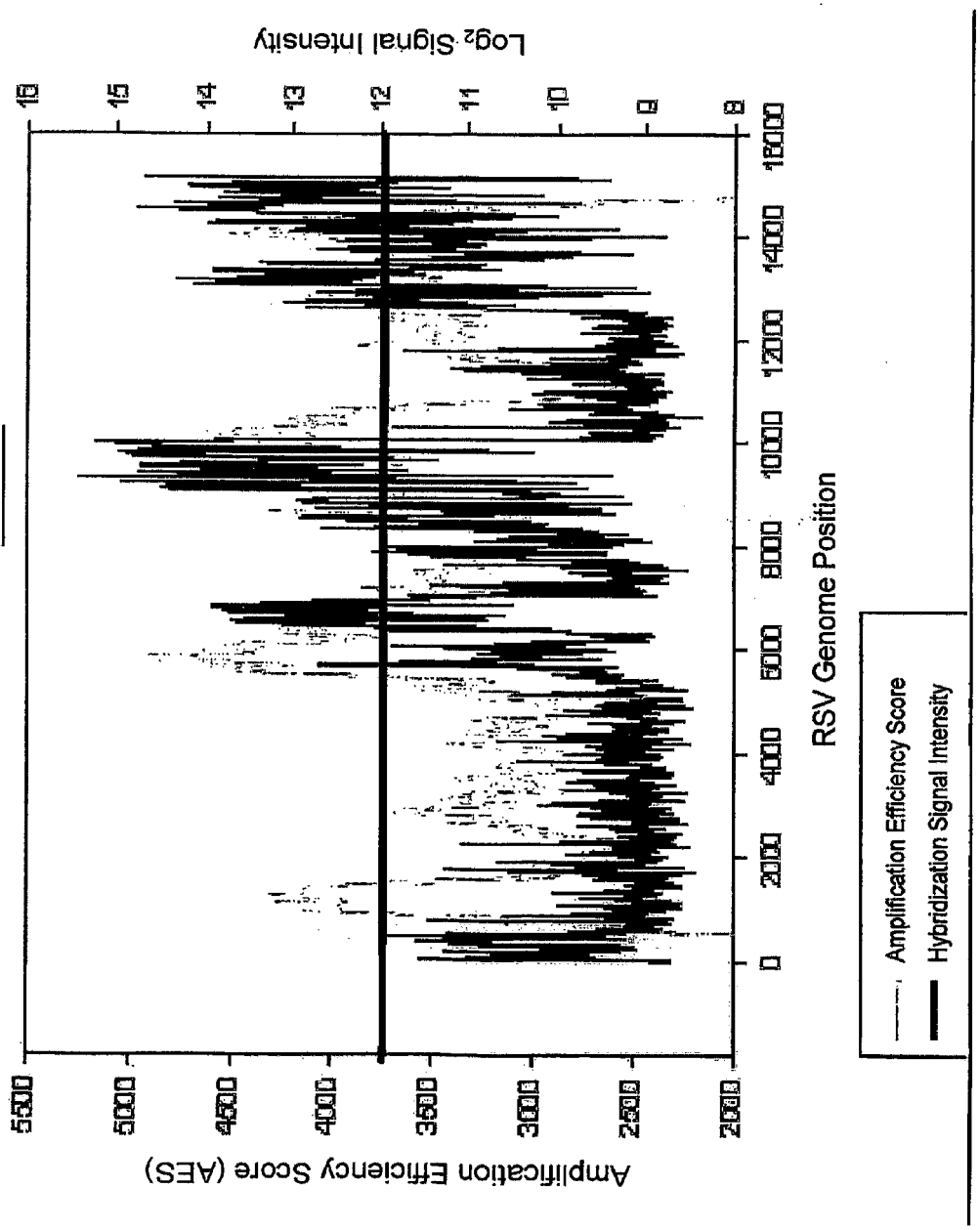

FIG. 12 Hybridization signal intensity correlates to Amplification Efficiency Score (AES), $P=2.2\times10^{-16}$. A RSV patient sample was hybridized onto a microarray, and signal intensities of each probe were plotted together with the computed AES. The signal threshold for high-confidence detection on a typical array is indicated by the green line.

Figure 13:
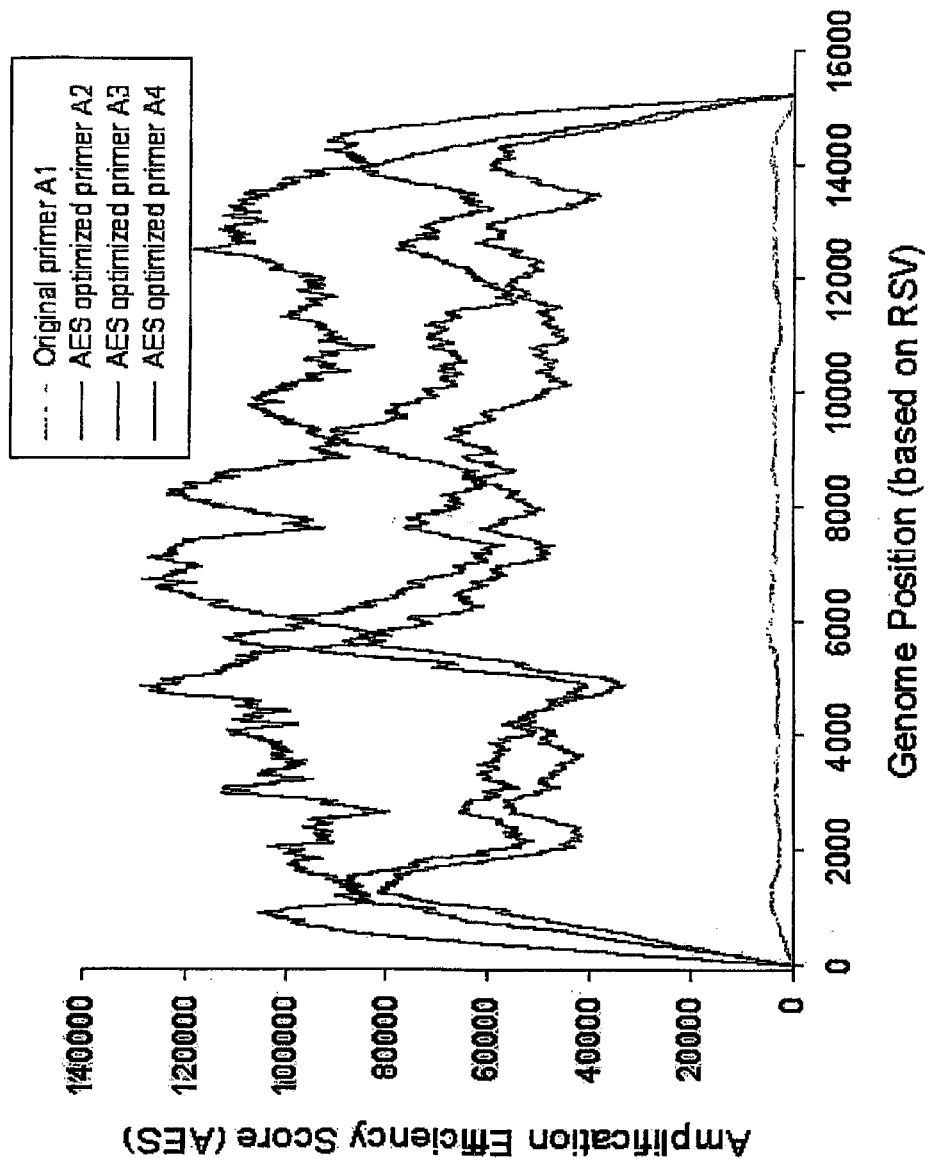

FIG. 13 Using AES-optimized primer tags for random RT-PCR increases the AES by 10-30-fold. The optimized primers were predicted to have the same performance across all 35 genomes represented on the microarray. Most patient samples were amplified using the AES-optimized primer A2.

| SEQ ID NO: | Primer | Nucleotide sequence |
|---|---|---|
| 10 | A1 | GTTTCCCAGTCACGATA |
| 11 | A2 | GATGAGGGAAGATGGGG |
| 12 | A3 | CTCATGCACGACCCAAA |
| 13 | A4 | AGATCCATTCCACCCCA |

Figure 14A:
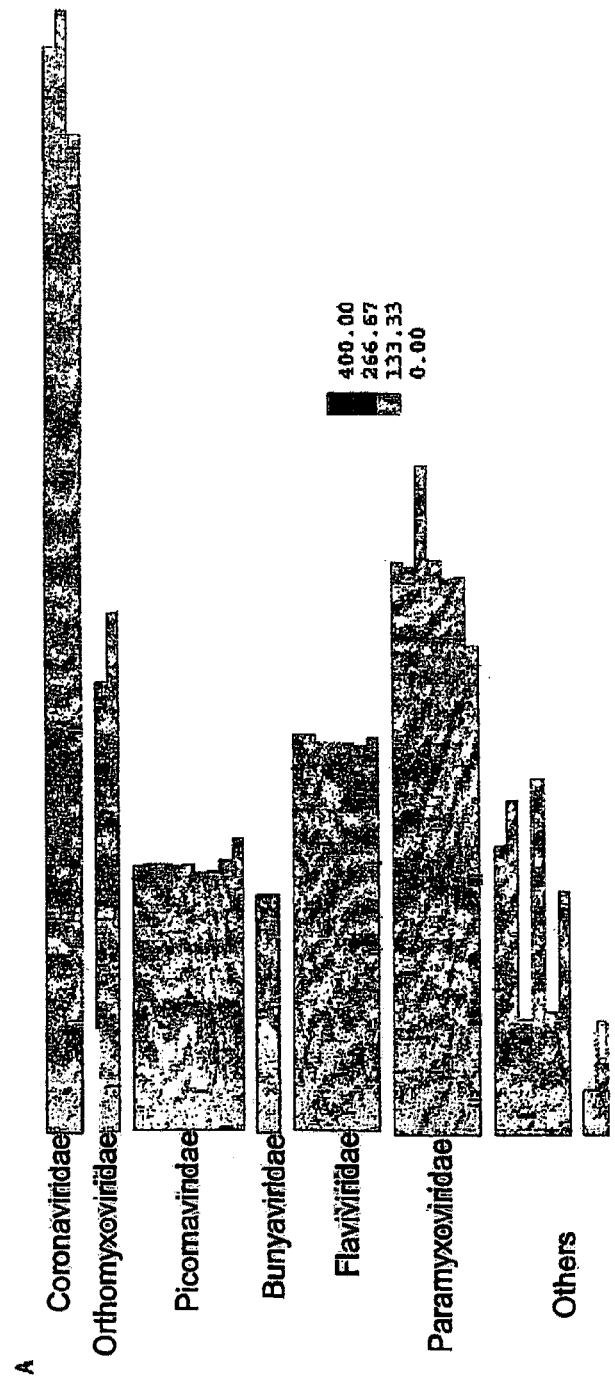
Figure 14B:
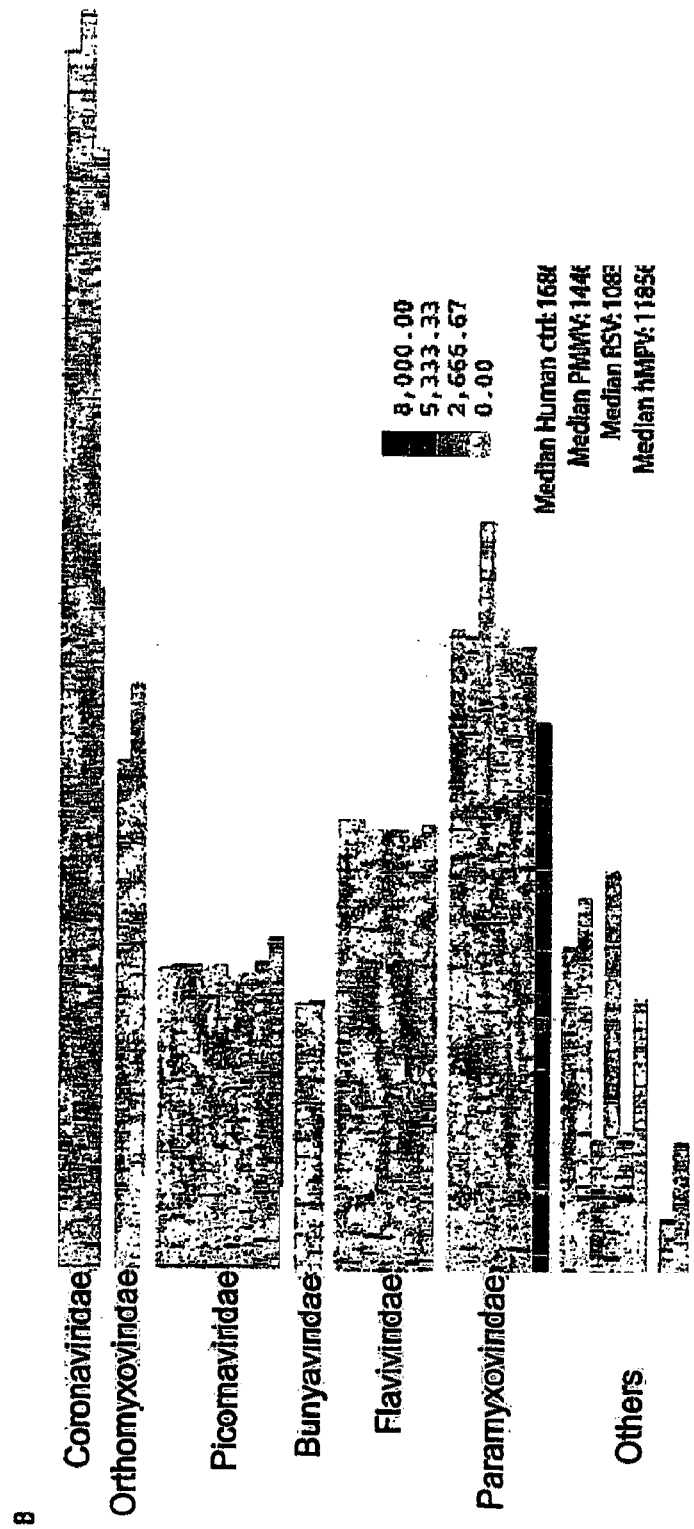

FIG. 14(A,B) Key to labels of microarray bars:

| Virus family | Virus genus/species |
|---|---|
| Orthomyxoviridae | Sars Sin2500 |
| | OC41 |
| | 229E |
| Coronaviridae | Flu A |
| | Flu B |
| Picornaviridae | Entero D |
| | Entero C |
| | Echo 1 |
| | Entero B |
| | Entero A |
| | Rhino 89 |
| | Rhino B |
| | Hep A |
| | Foot & mouth C |
| Bunyaviridae | Hantaan |
| | Sin Nombre |
| Flaviviridae | West Nile |
| | Jap enceph |
| | Dengue 3 |
| | Dengue 1 |
| | Dengue 2 |
| | Dengue 4 |
| | Yellow fever |
| Paramyxoviridae | Paraflu 1 |
| | Paraflu 3 |
| | Nipah |
| | Paraflu 2 |
| | Newcastle |
| | RSV (B1) |
| | Metapneumovirus |
| Others | HPV type 10 |
| | HIV 1 |
| | Hep B |
| | Rubella |
| | LCMV-S |
| | LCMV-L |
| | PMMV |
| | Human controls |

Choice of primer tag in random RT-PCR has significant effect on PCR efficiency. Heatmap showing probes hybridizing to a clinical hMPV sample following RT-PCR using (A) original primer described by Bohlander, et al. 1992, or (B) primer designed following PCR modeling to ensure that it will efficiently amplify all genomes (high AES) represented on the microarray.

FIG. 15 Diagnostic PCR results for RSV Patient #412 confirm that patient does not have a coronavirus infection. (A) PCR using Pancoronavirus primers. Lane 1: OC43 coronavirus positive control, Lane 2: 229E coronavirus positive control, Lane 3: RSV patient #412, Lane 4: PCR primers and reagents only negative control. 1 kb ladder. (B) PCR using OC43 specific primers. Lane 1: OC43 coronavirus positive control, Lane 2: RSV patient #412, Lane 3: purified RSV from ATCC, Lane 4: PCR negative control. 50 bp ladder. (C) PCR using 229E specific primers. Lane 1: 229E coronavirus positive control, Lane 2: RSV patient #412, Lane 3: PCR negative control. 1 kb ladder.

DETAILED DESCRIPTION OF THE INVENTION

Bibliographic references mentioned in the present specification are, for convenience, listed in the form of a list of references and added to the end of the examples. The whole content of such bibliographic references is herein incorporated by reference.

The present invention addresses the problems of the prior art, and in particular provides at least one method, apparatus and/or product of oligonucleotide design. In particular, there is provided a method, apparatus and/or product of probe and/or primer design. There is also provided a method, apparatus and/or product of nucleic acid(s) detection.

While the concept of using oligonucleotide hybridization microarrays as a tool for determining the presence of pathogens has been proposed, significant hurdles remain, thus preventing the use of these microarrays routinely (Striebel, H. M., 2003). These hurdles include probe design and data analysis (Striebel, H. M., 2003; Bodrossy, L. & Sessitsch, A., 2004; Vora, G. J., et al., 2004). The present inventors observed in a pilot microarray that despite meticulous probe selection, the best in silico designed probes do not necessarily hybridize well to patient samples. The inventors realized that to generate probes which would hybridize consistently well to patient material, it was necessary to develop a new and/or improved method of probe design so as to determine the optimal design predictors. In particular, as described in the Example section, the present inventors created a microarray comprising overlapping 40-mer probes, tiled across 35 viral genomes. However, the invention is not limited to this particular application, probe length and type of target nucleic acid.

According to a particular aspect of the invention, the present inventors describe how a support, in particular a microarray platform, is optimized so as to become a viable tool in target nucleic acid detection, in particular, in pathogen detection. The inventors also identified probe design predictors, including melting temperature, GC-content of the probe, secondary structure, hamming distance, similarity to human genome, effect of PCR primer tag in random PCR amplification efficiency, and/or the effect of sequence polymorphism. These results were considered and/or incorporated into the development of a method and criteria for probe and/or primer design. According to a more particular aspect, the inventors developed a data analysis algorithm which may accurately predict the presence of a target nucleic acid, which may or may not be a pathogen. For example the pathogen may be, but not limited to, a virus, bacteria and/or parasite(s). The algorithm may be used even if probes are not ideally designed. This detection algorithm, coupled with a probe design methodology, significantly improves the confidence level of the prediction (see Tables 6 and 7).

According to a particular aspect, the method of the invention may not require a prediction of the likely pathogen, but may be capable of detecting most known human viruses, bacteria and/or parasite(s), as well as some novel species, in an unbiased manner. Genome or a fragment thereof is defined as all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism. The rationale behind this detection platform according to the invention is that each species of virus, bacteria and/or parasite(s) contains unique molecular signatures within the primary sequence of their genomes. Identification of these distinguishing regions allows for rational oligonucleotide probe design for the specific detection of individual species, and in some cases, individual strains. The concomitant design and/or preparation of oligonucleotide (oligo) probes that represent the most highly conserved regions among family and genus members, will enable the detection and partial characterization of some novel pathogens. Furthermore, the inclusion of all such probes in a single support may allow the detection of multiple viruses, bacteria and/or parasite(s) that simultaneously co-infect a clinical sample. The support may be an insoluble support, in particular a solid support. For example, a microarray or a biochip assay.

According to a particular aspect, the invention may be used as a diagnostic tool, depending on the way in which oligonucleotide probes are designed, and/or how the data generated by the microarray is interpreted and analyzed.

Determination of Efficiency of Amplification

According to a first aspect, the present invention provides a method of designing oligonucleotide probe(s) for nucleic acid detection comprising the following steps in any order:
 (i) identifying and/or selecting at least one region of at least one target nucleic acid to be amplified, the region(s) having an efficiency of amplification (AE) higher than the average AE; and
 (ii) designing at least one oligonucleotide probe capable of hybridizing to the identified and/or selected region(s).

In particular, in step (i) a score of AE is determined for every position i on the length of the target nucleic acid or of a region thereof and an average AE is obtained. Those regions showing an AE higher than the average are selected as the region(s) of the target nucleic acid to be amplified. In particular, the AE of the selected region(s) may be calculated as the Amplification Efficiency Score (AES), which is the probability that a forward primer $r_i$ can bind to a position i and a reverse primer $r_j$ can bind at a position j of the target nucleic acid, and $|i-j|$ is the region of the target nucleic acid desired to be amplified. In particular, the region $|i-j|$ may be $\leq 10000$ bp, more in particular $\leq 5000$ bp, or $\leq 1000$ bp, for example $\leq 500$ bp. In particular, the forward and/or reverse primers may be random primers.

According to another aspect, the step (i) of identifying and/or selecting region(s) of a target nucleic acid to be amplified comprises determining the effect of geometrical amplification bias for every position of a target nucleic acid, and selecting the region(s) to be amplified as the region(s) having an efficiency of amplification (AE) higher than the average AE. The geometrical amplification bias may be defined as the capability of some regions of a nucleic acid to be amplified more efficiently than other regions. For example, the geometrical amplification bias is the PCR bias.

Modeling of Amplification Efficiency

Since it is not known what target nucleic acid (for example a pathogen) exists within the patient sample, random primers may be used during the amplification step and/or the reverse-transcription (RT) process to ensure unbiased reverse-transcription of all RNA present into DNA. Any random amplification method known in the art may be used for the purposes of the present invention. In the present description, the random amplification method may be RT-PCR. However, it will be clear to a skilled person that the method of the present invention is not limited to RT-PCR. In particular, the RT-PCR approach may be susceptible to signal inaccuracies caused by primer-dimer bindings and poor amplification efficiencies in the RT-PCR process (Bustin, S. A., et al, 2004). To overcome this hurdle, the inventors have modeled the RT-PCR process by using random primers.

Figure 1:
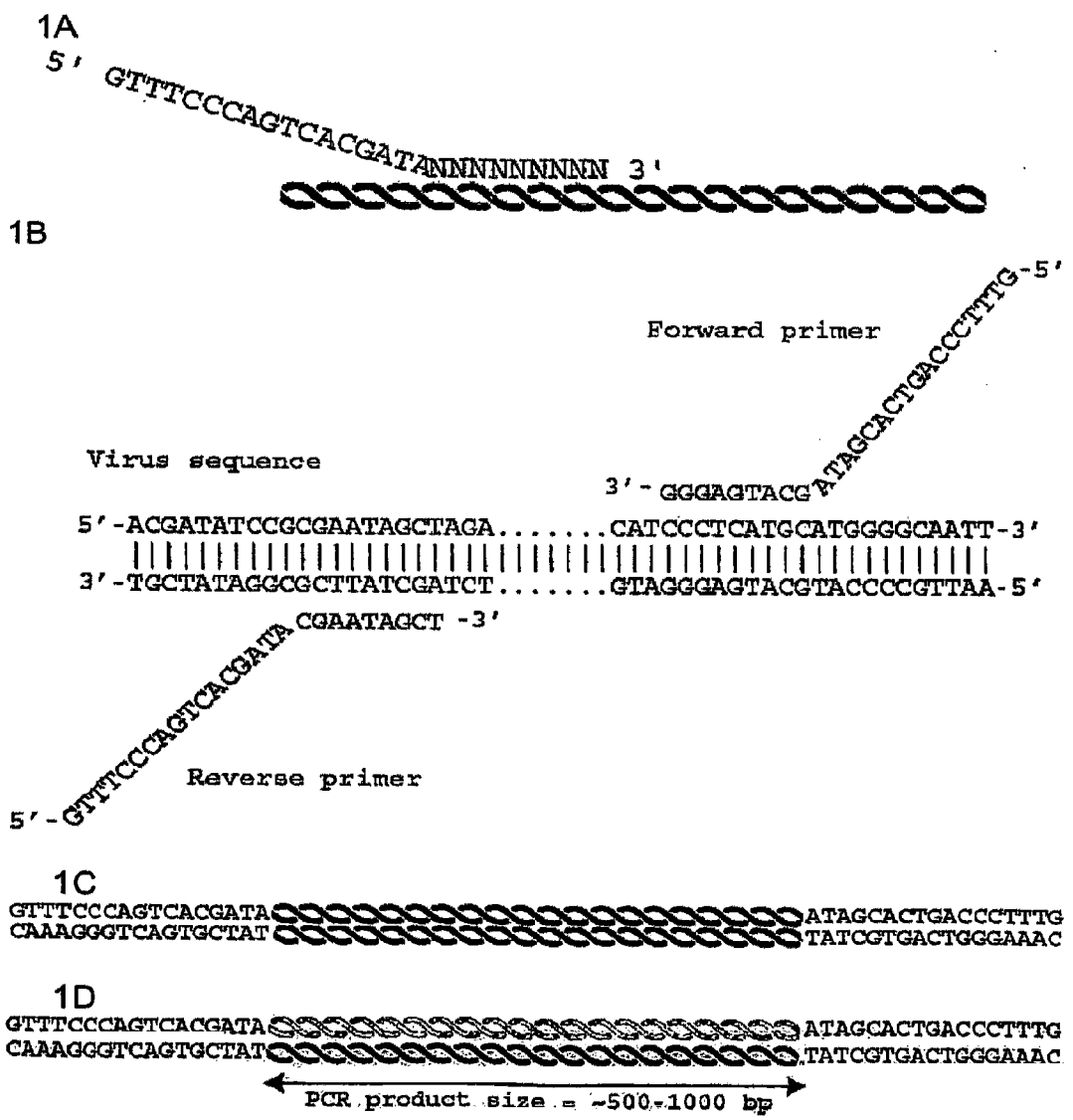
FIG. 1 shows a RT-PCR binding process of a pair of random primers on a virus sequence (SEQ ID NOS: 1 to 9). The labels for FIG. 1 are as follows.

According to a particular aspect of the invention, the amplification step comprises forward and reverse primers, and each of the forward and reverse primers comprises, in a 5'-3' orientation, a fixed primer header and a variable primer tail, and wherein at least the variable tail hybridizes to a portion of the target nucleic acid $v_a$. The size of the fixed primer header and that of the variable primer tail may be of any size, in mer, suitable for the purposes of the method according to the present invention. The fixed header may be 10-30 mer, in particular, 15-25 mer, for example 17 mer. The variable tail may be 1-20 mer, in particular, 5-15 mer, for example 9 mer. An example of these forward and reverse primers is shown in FIG. 1. More in particular, the amplification step may comprise forward and/or reverse random primers having the nucleotide sequence 5'-GTTTCCCAGTCACGA-TANNNNNNNNN-3', (SEQ ID NO:1), wherein N is any one of A, T, C, and G or a derivative thereof.

According to a particular embodiment, also exemplified in FIG. 1, the present inventors have modeled the random RT-PCR process as follows. Let $v_a$ be the actual virus in the sample. The random primer used in the RT-PCR process was preferably a 26-mer primer having a fixed 17-mer header and a variable 9-mer tail of the form (5'-GTTTCCCAGTCAC-GATANNNNNNNNN-3') (SEQ ID NO:1 and, in particular, SEQ ID NOS:2-7). However, it is clear to a skilled person the that primer according to the invention is not limited to the sequence(s) of SEQ ID NOS:1-7 and FIG. 1. In fact, nucleotide size of the primer, and in particular of the header and variable tail may be varied and chosen within the ranges discussed above. To obtain a RT-PCR product in a region between positions i and j of $v_a$, the inventors required (1) a forward primer binding to position i, (2) $|i-j| \leq 10000$, and (3) a reverse primer binding to position j. In particular, $|i-j|$, which is the region of the target nucleic acid desired to be amplified, may be $\leq 5000$ bp, more in particular $\leq 1000$, for example $\leq 500$ bp. The quality of the RT-PCR product depends on how well the forward primer and/or the reverse primer bind to $v_a$. Some random primers can bind to $v_a$ better than others. The identification of such primers and where they bind to $v_a$ gives an indication of how likely a particular region of $v_a$ will be amplified. Using this approach, there is provided an amplification efficiency model which computes an Amplification Efficiency Score (AES) for every position of $v_a$.

For a particular position i of a target nucleic acid $v_a$, $P^f(i)$ and $P^r(i)$ are the probabilities that a random primer $r_i$ can bind to position i of $v_a$ as forward primer and reverse primer respectively. For simplicity, it is assumed that a random primer can only bind to $v_a$ if the last 9 nucleotides of the random primer is a substring of the reverse complement of $v_a$ (forward primer) or a substring of $v_a$ (reverse primer). This is shown in FIG. 1. Based on well-established primer design criteria (Wu, D. Y., et al., 1991), the $P^f(i)$ was estimated to be low if $r_i$ forms a significant primer-dimer or has extreme melting temperature. On the other hand, if $r_i$ does not form any significant primer-dimer and has optimal melting temperature, then $P^f(i)$ will be high. Note that if the header of the random primer is similar to $v_a$, it may also aid in the binding and thus result in a higher $P^f(i)$. Similarly, the $P^r(i)$ was computed.

The binding of the random primer $r_i$ at position i of $v_a$ as a forward primer affects the quality of the RT-PCR product for at least 10000 nucleotides upstream of position i. Similarly, the binding of the random primer $r_i$ at position i of $v_a$ as a reverse primer affects the quality of the RT-PCR product for at least 10000 nucleotides downstream of position i. Thus, an amplification efficiency score, $AES_i$, for every position i of $v_a$ can be computed by considering the combined effect of all forward and reverse primer-pairs that amplifies it:

$$AES_i = \sum_{j=i-Z}^{i} \left\{ P^f(j) \times \sum_{k=\max(i+1,j+500)}^{j+Z} P^r(k) \right\}$$

wherein $$\sum_{k=\max(i+1,j+500)}^{j+Z} P^r(k) = P^r(i+1) + P^r(i+2) + \ldots P^r(j+Z)$$

$P^f(i)$ and $P^r(i)$ is the probability that a random primer $r_i$ can bind to position i of $v_a$ as forward primer and reverse primer, respectively, and $Z \leq 10000$ bp is the region of $v_a$ desired to be amplified.

Accordingly, Z may be $\leq 10000$ bp, $\leq 5000$ bp, $\leq 1000$ bp or $\leq 500$ bp.

To verify if the variation in signal intensities displayed by different regions of a virus has direct correlation with their corresponding amplification efficiency scores, several microarray experiments (in the particular case, a total of five microarray experiments) were performed on a common pathogen affecting human, the human respiratory syncytial virus B (RSV B).

Modeling of RT-PCR for Amplification Efficiency

According to the method of the invention, which is an improvement of the method of (Sung et al. 2003, CSB) the primer used for the reverse transcription comprises a fixed oligonucleotide tag (header) and a random oligonucleotide tail. In theory, the random oligonucleotide tail should bind indiscriminately to all nucleic acids in the patient sample, initiating first strand synthesis. After the second strand synthesis, all reversed-transcribed sequences will have the fixed oligonucleotide tag (header) at both ends. These sequences are amplified by PCR, using the fixed oligonucleotide tag (header) as the primer to generate PCR products of at least 10000 bp in length. In particular, the majority of the amplified PCR products are between 500-1000 bp in length. According to the particular embodiment, the 26-mer primer used for reverse transcription (RT) comprises a fixed 17-mer tag with a 9-mer random tail: 5'-GTTTCCCAGTCACGA-TANNNNNNNNN-3' (SEQ ID NO:1).

In our model, $v_a$ represents the pathogen in the clinical sample. To generate at least one PCR product, for example of 500-1000 bp, in any region of the genome, defined by positions i and j of $v_a$ requires a forward primer binding to position i and a reverse primer binding to position j in the anti-sense direction such that $500 \leq |i-j| \leq 10000$, and in particular, such that $500 \leq |i-j| \leq 1000$. The binding affinity of a primer is determined by at least two factors: (1) primer dimer formation, and (2) hybridization affinity of the primer to the virus $v_a$. Genomic regions which can be successfully amplified by virtue of having ideal primer binding locations within 10000 nucleotides, in particular within 1000 or 500 nucleotide, can be predicted for by calculating an Amplification Efficiency Score (AES) for every position of $v_a$: FIG. 1.

Amplification Efficiency Score (AES)

For each position i of $v_a$, let $P^f(i)$ and $P^r(i)$ be the probability that a random primer $r_i$ can bind to position i of $v_a$ as forward primer and reverse primer respectively. For simplicity, we assumed that a random primer can only bind to $v_a$ if the nucleotide of the random tail of the primer (for example, the last 9 nucleotides of the random primer as shown in FIG. 1) is a substring of the reverse complement of $v_a$ (forward primer) or a substring of $v_a$ (reverse primer; FIG. 1). Based on well-established primer design criteria (Wu and Ugozzoli, 1991), we estimated $P^f(i)$ to be low if $r_i$ formed a significant primer-dimer or had extreme melting temperature. On the other hand, if $r_i$ did not form any significant primer-dimer and had optimal melting temperature, then $P^f(i)$ will be high. If the fixed oligonucleotide tag (header) of the random primer (for example, the fixed 17-mer tag shown in FIG. 1) is similar to $v_a$, it may also aid In the binding and thus result in a higher $P^f(i)$. Similarly, we computed $P^r(i)$.

The binding of the random primer $r_i$ at position i of $v_a$ as a forward primer affects the quality of the RT-PCR product for the nucleotides upstream of position l (for example, for the 500 to 1000 nucleotides upstream of position i). Similarly, the binding of the random primer $r_i$ at position i of $v_a$ as a reverse primer affects the quality and coverage of the RT-PCR product for the nucleotides downstream of position l (for example, for the 500 to 1000 nucleotides downstream of position i). Consider a position x of $v_a$. All effective primer pairs that reside at positions i and j respectively contribute to the quality of the RT-PCR product at x. Note that i=x=j and i-j=10000. For example, $500 \leq i-j \leq 1000$ since our RT-PCR product when 500 to 1000 basepairs long. Thus, an Amplification Efficiency Score, $AES_x$, for every position x of $v_a$ can be computed by considering the combined effect of all primer pairs that amplifies it:

$$AES_i = \sum_{j=x-1000}^{x} \left\{ P^f(j) \times \sum_{k=\max(x+1,j+500)}^{j+1000} P^r(k) \right\}$$

AES Threshold Predictive of Successful RT-PCR

The threshold for amplification efficiency scores for probe selection for a virus $v_a$ is determined by the cumulative distribution function of the AES values $v_a$. Let X be the random variable representing the AES values of all probes of $v_a$. Let k be the number of probes in $v_a$. Then, we denote the probability that the AES value is less than or equal to x be $$P(X \leq x) = \frac{c}{k}$$

where c is the number of probes which have AES values less than or equal to x. For a probe $p_i$ at position i of $v_a$, let $x_i$ be its corresponding AES value. Since the signal intensity of a probe is highly correlated to its AES value, we estimated $P(p_i|v_a)$, the probability that $p_i$ has high signal intensity in the presence of $v_a$, to be $P(X \leq x_i)$. Thus, $$P(p_i | v_a) \approx P(X \leq x_i) = \frac{c_i}{k}$$

where $c_i$ is the number of probes whose AES values are less than or equal to $x_i$.

For probe selection, probe $p_i$ is selected if $P(p_i|v_a) > \lambda$. In our experiments, we set $\lambda=0.8$. At this threshold (top 20% AES), we observed that more than 50% of expected probes would hybridize reproducibly to different clinical samples. While using probes with higher AES (eg. top 10% AES) would improve reproducibility, this would reduce the number of unique probes remaining for some genomes to $\leq 100$ at the species level, consequently eroding the ability of the array to specifically identify pathogen. Thus top 20% AES was used.

Empirical Determination of Cross-Hybridization Thresholds on a Pathogen Detection Microarray:

Probe Design

The step (ii) of designing oligonucleotide probe(s) capable of hybridizing to the selected region(s) may be selected to any one of the probe designing techniques known in the art. The following description relates to probe design, however, it will be clear to a skilled person to apply the same principle also for designing primer(s), in particular, for designing primer(s) for RT-PCR.

For example, given a set of target nucleic acids (for example, viral genomes) $V=\{v_1, v_2, \ldots, v_n\}$, for every $v_i \in V$, a set of length-m probes (that is a substring of $v_i$) which satisfies the following conditions may be designed taking into consideration, for example, at least one of the following:

(a) established probe design criteria of homogeneity, sensitivity and specificity (Sung, W. K et al, 2003, CSB);

(b) no significant sequence similarity to human genome; and (c) efficiently amplified using AE score, for example by RT-PCR, as herein described.

Noisy signals caused by cross-hybridization artifacts present a major obstacle to the interpretation of microarray data, particularly for the identification of rare pathogen sequences present in a complex mixture of nucleic acids. For example, in clinical specimens, contaminating nucleic acid sequences such as those derived from the host tissue, will cross-hybridize with pathogen-specific microarray probes above some threshold of sequence complementarity. This can result in false-positive signals leading to erroneous, conclusions. Similarly the pathogen sequence, in addition to binding its specific probes, may cross-hybridize with other non-target probes (i.e., designed to detect other pathogens). This latter phenomenon, though seemingly problematic, could provide useful information for pathogen identification to the extent that such cross-hybridization may be accurately predicted. With various metrics to assess annealing potential and sequence specificity, microarray probes have traditionally been designed to ensure maximal specific hybridization (to a known target) with minimal cross-hybridization (to non-specific sequences). However, in practice we have found that many probes, though designed using optimal in silico parameters, do not perform according to expectations for reasons that are unclear.

To systematically investigate the dynamics of array-based pathogen detection, we created an oligonucleotide array using Nimblegen array synthesis technology (Nuwaysir et al. 2002). The array was designed to detect up to 35 RNA viruses using 40-mer probes tiled at an average 8-base resolution across the full length of each genome (53,555 probes; FIG. 6, Table 1).

TABLE 1

List of Genomes represented on the pathogen detection microarray.
(column 1) Number of probes for each genome synthesized on the microarray.
(column 2) Number of probes for each genome remaining following application
of probe design filters. (column 3) Number of probes for each genome which
are unique to the genome and do not cross-hybridize with human.

| Genome | Original No. of Probes (1) | Filtered No. of Probes (2) | Unique Probes (3) | NCBI GI number | Ref type | Accession no. | Description |
|---|---|---|---|---|---|---|---|
| 1 | 1948 | 537 | 271 | 9629198 | RefSeq | NC_001781.1 | Human respiratory syncytial virus, complete genome |
| 2 | 1995 | 550 | 295 | 19718363 | RefSeq | NC_003461.1 | Human parainfluenza virus 1 strain Washington/1964, complete genome |
| 3 | 2002 | 762 | 474 | 19525721 | RefSeq | NC_003443.1 | Human parainfluenza virus 2, complete genome |
| 4 | 1979 | 701 | 345 | 10937870 | RefSeq | NC_001796.2 | Human parainfluenza virus 3, complete genome |
| 5 | 3805 | 588 | 444 | 30468042 | Genbank | AY283794.1 | SARS coronavirus Sin2500, complete genome |
| 6 | 3937 | 604 | 356 | 38018022 | RefSeq | NC_005147.1 | Human coronavirus OC43, complete genome |
| 7 | 3495 | 182 | 112 | 12175745 | RefSeq | NC_002645.1 | Human coronavirus 229E, complete genome |
| 8 | 1705 | 292 | 177 | 46852132 | RefSeq | NC_004148.2 | Human metapneumovirus, complete genome |
| 9 | 296 | 118 | 101 | 8486138 | RefSeq | NC_002023.1 | Influenza A virus RNA segment 1, complete sequence |
| 10 | 282 | 69 | 42 | 8486136 | RefSeq | NC_002022.1 | Influenza A virus RNA segment 3, complete sequence |
| 10 | 296 | 81 | 54 | 8486134 | RefSeq | NC_002021.1 | Influenza A virus RNA segment 2, complete sequence |
| 10 | 110 | 69 | 57 | 8486131 | RefSeq | NC_002020.1 | Influenza A virus RNA segment 8, complete sequence |

TABLE 1-continued

List of Genomes represented on the pathogen detection microarray.
(column 1) Number of probes for each genome synthesized on the microarray.
(column 2) Number of probes for each genome remaining following application
of probe design filters. (column 3) Number of probes for each genome which
are unique to the genome and do not cross-hybridize with human.

| Genome | Original No. of Probes (1) | Filtered No. of Probes (2) | Unique Probes (3) | NCBI GI number | Ref type | Accession no. | Description |
|---|---|---|---|---|---|---|---|
| 10 | 196 | 71 | 62 | 8486129 | RefSeq | NC_002019.1 | Influenza A virus RNA segment 5, complete sequence |
| 10 | 177 | 75 | 59 | 8486127 | RefSeq | NC_002018.1 | Influenza A virus RNA segment 6, complete sequence |
| 10 | 225 | 70 | 51 | 8486125 | RefSeq | NC_002017.1 | Influenza A virus RNA segment 4, complete sequence |
| 10 | 300 | 105 | 48 | 8486164 | RefSeq | NC_002204.1 | Influenza B virus RNA-1, complete sequence |
| 10 | 293 | 113 | 74 | 8486148 | RefSeq | NC_002205.1 | Influenza B virus RNA-2, complete sequence |
| 10 | 279 | 94 | 59 | 8486150 | RefSeq | NC_002206.1 | Influenza B virus RNA-3, complete sequence |
| 10 | 237 | 70 | 53 | 8486152 | RefSeq | NC_002207.1 | Influenza B virus RNA-4, complete sequence |
| 10 | 232 | 90 | 82 | 8486154 | RefSeq | NC_002208.1 | Influenza B virus RNA-5, complete sequence |
| 10 | 195 | 64 | 32 | 8486156 | RefSeq | NC_002209.1 | Influenza B virus RNA-6, complete sequence |
| 10 | 150 | 47 | 37 | 8486159 | RefSeq | NC_002210.1 | Influenza B virus RNA-7, complete sequence |
| 10 | 136 | 59 | 50 | 8486161 | RefSeq | NC_002211.1 | Influenza B virus RNA-8, complete sequence |
| 11 | 1401 | 85 | 54 | 11528013 | RefSeq | NC_001563.2 | West Nile virus, complete genome |
| 12 | 1389 | 145 | 123 | 9627244 | RefSeq | NC_002031.1 | Yellow fever virus, complete genome |
| 13 | 2335 | 235 | 171 | 13559808 | RefSeq | NC_002728.1 | Nipah virus, complete genome |
| 14 | 1943 | 244 | 211 | 11545722 | RefSeq | NC_002617.1 | Newcastle disease virus, complete genome |
| 15 | 1174 | 208 | 128 | 9629357 | RefSeq | NC_001802.1 | Human immunodeficiency virus 1, complete genome |
| 16 | 409 | 134 | 106 | 21326584 | RefSeq | NC_003977.1 | Hepatitis B virus, complete genome |
| 17 | 1011 | 169 | 135 | 9627257 | RefSeq | NC_001576.1 | Human papillomavirus type 10, complete genome |
| 18 | 1036 | 325 | 299 | 10445391 | RefSeq | NC_002554.1 | Foot-and-mouth disease virus C, complete genome |
| 19 | 1246 | 211 | 209 | 9790308 | RefSeq | NC_001545.1 | Rubella virus, complete genome |
| 20 | 955 | 309 | 172 | 9626732 | RefSeq | NC_001489.1 | Hepatitis A virus, complete genome |
| 21 | 834 | 103 | 29 | 38371716 | RefSeq | NC_005222.1 | Hantaan virus, complete genome |
| 22 | 837 | 188 | 98 | 38371727 | RefSeq | NC_005217.1 | Sin Nombre virus, complete genome |
| 23 | 430 | 100 | 86 | 23334588 | RefSeq | NC_004294.1 | Lymphocytic choriomeningitis virus segment S, complete sequence |
| 23 | 853 | 455 | 286 | 23334585 | RefSeq | NC_004291.1 | Lymphocytic choriomeningitis virus segment L, complete sequence |
| 24 | 1404 | 204 | 122 | 9626460 | RefSeq | NC_001437.1 | Japanese encephalitis virus, genome |
| 25 | 1370 | 284 | 91 | 51850386 | DNA Database of Japan | AB189128.1 | Dengue virus type 3 genomic RNA, complete genome, strain: 98902890 DF DV-3 |
| 26 | 1361 | 130 | 57 | 12659201 | Genbank | AF326573.1 | Dengue virus type 4 strain 814669, complete genome |
| 27 | 1370 | 142 | 21 | 19744844 | Genbank | AF489932.1 | Dengue Virus Type 2 strain BR64022, complete genome |
| 28 | 1370 | 152 | 52 | 323660 | Genbank | M87512.1 | DENT1SEQ Dengue virus type 1 complete genome |
| 29 | 944 | 175 | 87 | 9626436 | RefSeq | NC_001430.1 | Human enterovirus D, complete genome |
| 30 | 945 | 183 | 122 | 9626433 | RefSeq | NC_001428.1 | Human enterovirus C, complete genome |
| 31 | 946 | 196 | 148 | 9627719 | RefSeq | NC_001612.1 | Human enterovirus A, complete genome |
| 32 | 945 | 364 | 154 | 21363125 | RefSeq | NC_003986.1 | Human echovirus 1, complete genome |
| 33 | 944 | 94 | 12 | 9626677 | RefSeq | NC_001472.1 | Human enterovirus B, complete genome |
| 34 | 913 | 283 | 190 | 9627730 | RefSeq | NC_001617.1 | Human rhinovirus 89, complete genome |

TABLE 1-continued

List of Genomes represented on the pathogen detection microarray.
(column 1) Number of probes for each genome synthesized on the microarray.
(column 2) Number of probes for each genome remaining following application
of probe design filters. (column 3) Number of probes for each genome which
are unique to the genome and do not cross-hybridize with human.

| Genome | Original No. of Probes (1) | Filtered No. of Probes (2) | Unique Probes (3) | NCBI GI number | Ref type | Accession no. | Description |
|---|---|---|---|---|---|---|---|
| 35 | 920 | 426 | 291 | 9626735 | RefSeq | NC_001490.1 | Human rhinovirus B, complete genome |

Together with 7 replicates for each viral probe, and control sequences for array synthesis and hybridization (as described below), the array contained a total of 390,482 probes.

Homogeneity, Sensitivity and Specificity

Homogeneity requires the selection of probes which have similar melting temperatures. It was found that probes with low CG-content did not produce reliable hybridization signal intensities, and that probes with high CG-content had a propensity to produce high signal intensities through non-specific binding. Thus, it could be established that the CG-content of probes selected should be from 40% to 60%.

Accordingly, the present invention provides a method of designing oligonucleotide probe(s) for nucleic acid detection, comprising selecting the probes having a CG-content from 40% to 60%.

The term "hybridization" refers to the process in which the oligo probes bind non-covalently to the target nucleic acid, or portion thereof, to form a stable double-stranded. Triple-stranded hybridization is also theoretically possible. Hybridization probes are oligonucleotides capable of binding in a base-specific manner to a complementary strand of target nucleic acid. Hybridizing specifically refers to the binding, duplexing, or hybridizing of a molecule substantially to or only to a particular nucleotide sequence or sequences under stringent conditions when that sequence is present in a complex mixture (e.g., total cellular) of DNA or RNA. Hybridizations, e.g., allele-specific probe hybridizations, are generally performed under stringent conditions. For example, conditions where the salt concentration is no more than about 1 Molar (M) and a temperature of at least 25° C., e.g., 750 mM NaCl, 50 mM NaPhosphate, 5 mM EDTA, pH 7.4 (5 times SSPE) and a temperature of from about 25° C. to about 30° C. Hybridization is usually performed under stringent conditions, for example, at a salt concentration of no more than 1 M and a temperature of at least 25° C. For stringent conditions, see also for example, Sambrook and Russel, Molecular Cloning: A Laboratory Manual, Cold Springs Harbor Laboratory, New York (2001) which is hereby incorporated by reference in its entirety for all purposes above.

Sensitivity requires that probes that cannot form significant secondary structures be selected in order to detect low-abundance mRNAs. Thus, probes with the highest free energy computed based on Nearest-Neighbor model are selected (SantaLucia, J., Jr., et al., 1996).

Accordingly, the present invention provides a method of designing at least one oligonucleotide probe for nucleic acid(s) detection, wherein the probe(s) are selected by having the highest free energy computed based on Nearest-Neighbor model.

Specificity requires the selection of probes that are most unique to a viral genome. This is to minimize cross-hybridization of the probes with other non-target nucleic acids (for example, viral genomes). Given probe $s_a$ and probe $s_b$ substrings of target nucleic acids $v_a$ and $v_b$, $s_a$ is selected based on the hamming distance between $s_a$ and any length-m substring $s_b$ from the target nucleic acid $v_b$ and/or on the longest common substring of $s_a$ and probe $S_b$. In particular, let $s_a$ and $s_b$ be length-m substrings from viral genome $v_a$ and $v_b$, respectively, where ($v_a \neq v_b$).

The length of the probe(s) to be designed may be of any length useful for the purposes of the present invention. The probes may be less than 100 mer, for example 20 to 80 mer, 25 to 60 mer, for example 40 mer. The hamming distance and/or longest common substring may also vary.

According to Kane's criteria (Kane, M. D., et al., 2000), $s_a$ is specific to $v_a$ if:
(a) the hamming distance between $s_a$ and any length-m substring $s_b$ from viral genome $v_b$, is more than 0.25 m;
(b) the longest common substring of $s_a$ and $s_b$ is less than 15.

The cutoff value(s) for the hamming distance may be chosen according to the stringency desired. It will be evident to any skilled person how to select the hamming distance cutoff according to the particular stringency desired. According to a particular example of the herein described probe design, the inventors used hamming distance cutoffs of >10 with respect to other target nucleic acids for specific probes, and <10, preferably <5 for conserved probes. With a specific probe, it indicates a probe which only hybridizes to a specific target nucleic acid, while with a conserved probe it indicates a probe which may hybridize to any member of the family of the target nucleic acid.

Accordingly, the present invention also provides a method of designing oligonucleotide probe(s) for nucleic acid detection, wherein given probe $s_a$ and probe $s_b$ substrings of target nucleic acids $v_a$ and $v_b$ comprised in the biological sample, $s_a$ is selected if the hamming distance between $s_a$ and any length-m substring $s_b$ from the target nucleic acid $v_b$ is more than 0.25 m, and the longest common substring of $s_a$ and probe $s_b$ is less than 15.

Figure 7A:
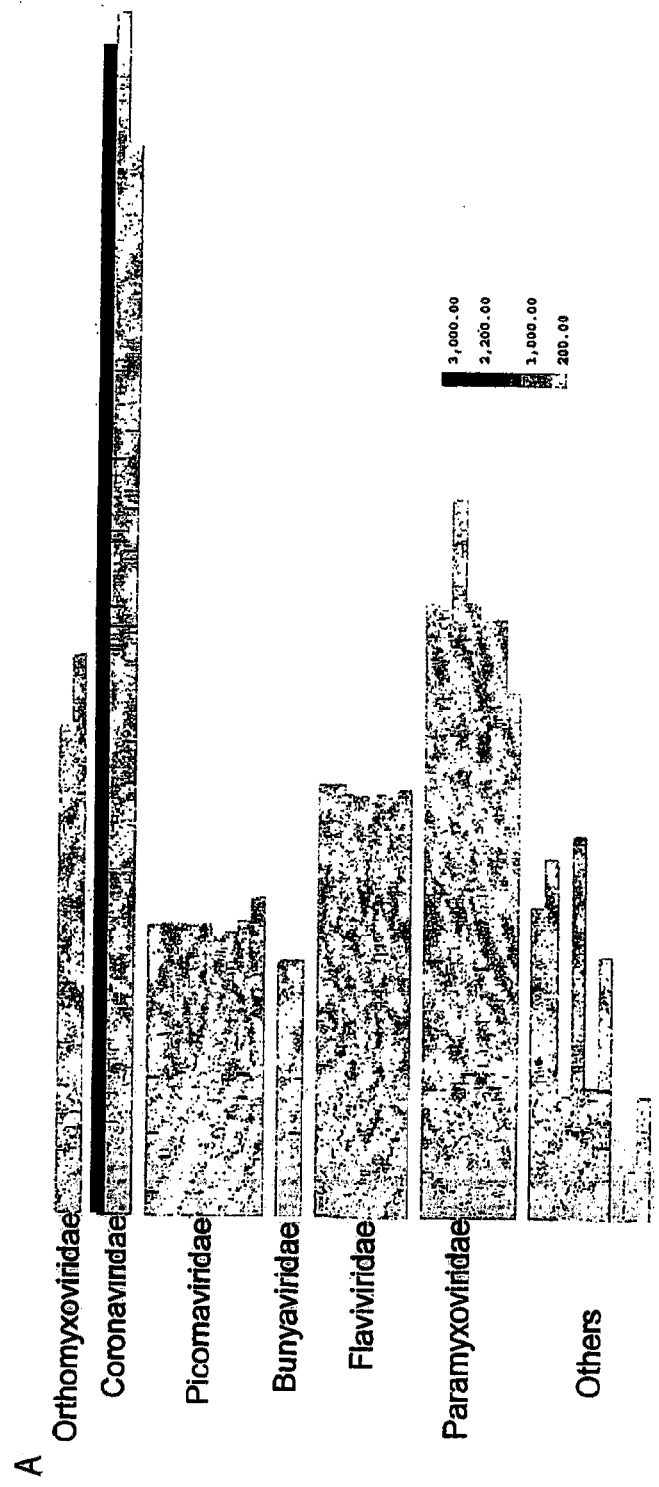
Figure 7B:
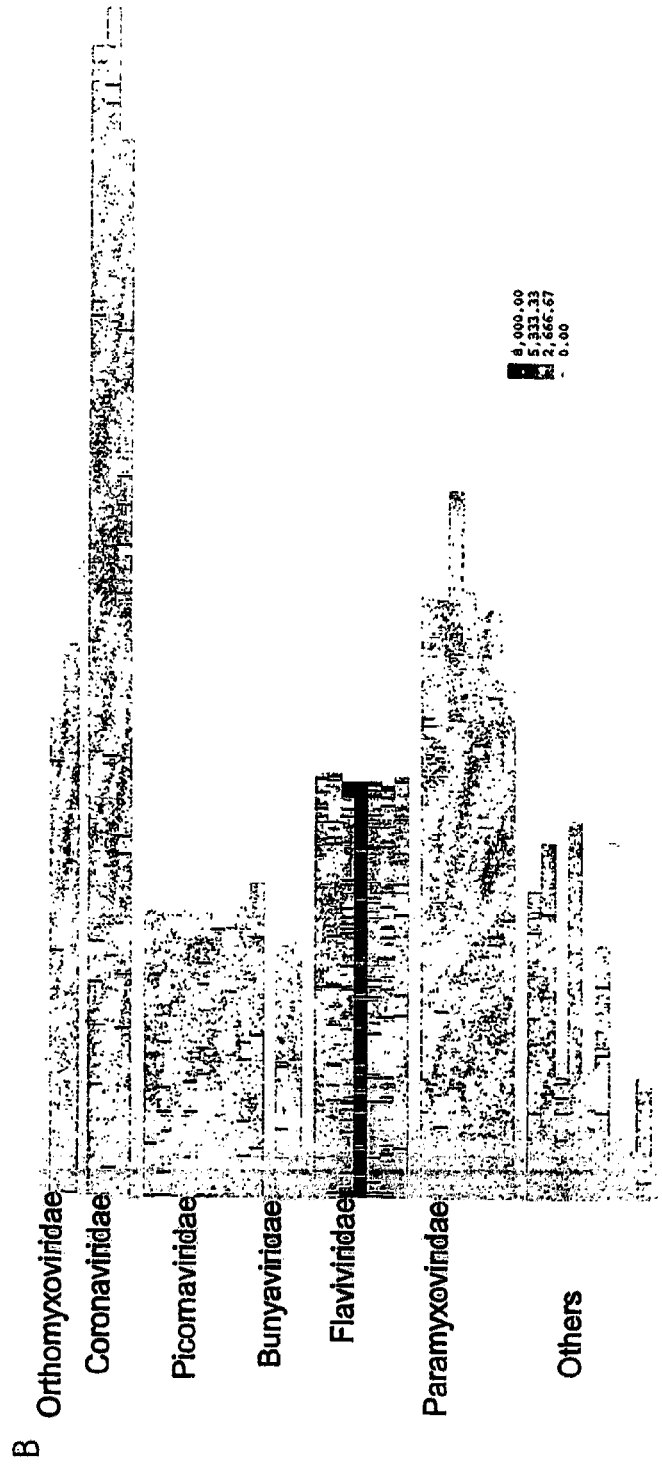
Figure 7C:
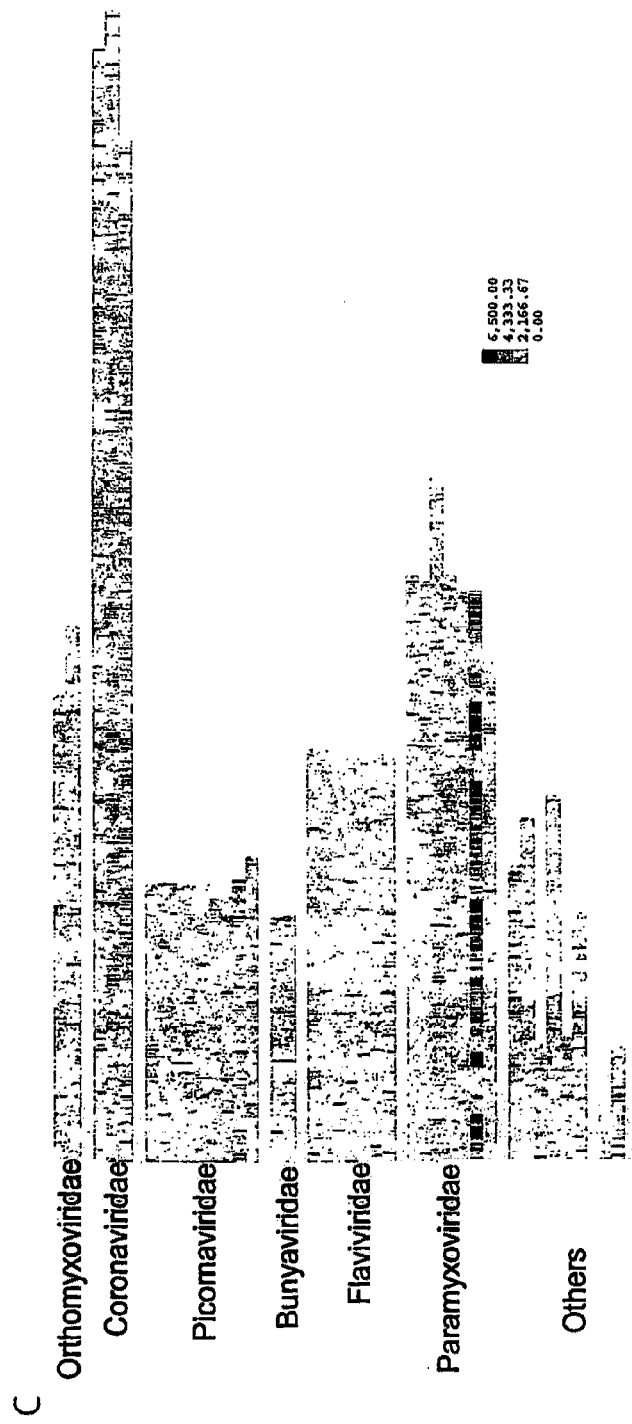

To study array hybridization dynamics without the complexity of cross-hybridization from human RNA, SARS coronavirus and Dengue serotype 1 viral RNA were purified from the media of infected cell lines, reverse-transcribed, and PCR-amplified using virus-specific primers (Wong, et. al., 2004). Each genome cDNA was amplified in its entirety (as confirmed by sequencing), labeled with Cy3 and hybridized separately on microarrays. The SARS sample hybridized well to the SARS tiling probes, with all 3,805 SARS-specific probes displaying fluorescent (Cy3) signal well above the detection threshold (determined by probe signal intensities>2 standard deviations above the mean array signal intensity; FIG. 7A) Cross-hybridization with other pathogen probe sets was minimal, observed only for other members of Coronaviridae and a few species of Picornaviridae and Paramyxoviridae, consistent with the observation that SARS shares little sequence homology with other known viruses (Ksiazek et al. 2003). The hybridization pattern of Dengue 1, on the other hand, was more complex (FIG. 7B). First, we observed that hybridization to the Dengue 1 probe set was partially incomplete (i.e., regions absent of signal) due to sequence polymorphisms. The Dengue 1 sample hybridized on the array was cultured from a Hawaiian isolate in 1944 (ATCC Catalog #VR-1254), whereas the array probe set is based on the sequence of strain S275/90, isolated in Singapore in 1990 (Fu et al. 1992). The Dengue 1 probes that failed to hybridize with the cDNA target each contained at least 3 mismatches (within a 15-base stretch) with the target sequence. Second, we observed that cross-hybridization occurred to some degree with almost all viral probe sets present on the array, particularly with probes of other Flaviviridae members, consistent with the fact that the 4 Dengue serotypes share 60-70% homology. To understand the relationship between hybridization signal output and annealing specificity, we first compared all probe sequences to each viral genome using 2 measures of similarity: probe hamming, distance (HD) and maximum contiguous match (MCM). HD measures the overall similarity distance of two sequences, with low scores for similar sequences (Hamming, 1950). MCM measures the number of consecutive bases which are exact matches, with high scores for similar sequences (Kane et al. 2000).

We calculated the HD and MCM scores for every probe relative to the Hawaiian Dengue 1 isolate and observed that these scores are inversely and directly correlated respectively to probe signal intensity. All probes on the array with high similarity to the Hawaiian Dengue I genome, i.e. HD=2 (n=942) or MCM=27 (n=627), hybridized with median signal intensity 3 logs above background. Although 98% of probes were detectable at the low HD range from 0-4, or high MCM range from 18-40, median probe signal intensity decreased at every increment of sequence distance. Median signal intensity dropped off sharply to background levels at HD=7 and MCM=15, with 43% and 46% detectable probes respectively. The majority of probes (>96%, n>51,000) had HD scores between 8-21 and/or MCM scores between 0-15, of which 1.23% and 1.57% were detectable respectively.

The ideal cross-hybridization similarity threshold would be one where all probes identifying a specific pathogen would always have detectable signal intensity above background noise, even in the presence of polymorphisms in the pathogen sequence. At the optimal similarity thresholds HD=4 and MCM=18, >98% of probes could be detected with median signal intensity 2 logs above background, whereas adjusting the threshold down 1 step to HD=5 and MCM=17 would result in only ~85% probe detection and median signal intensity ~1.2 logs above background (FIG. 8)

Using, these optimal HD and MCM thresholds to predict for cross hybridization, we binned all probes into groups most likely to detect a given pathogen. We refer to these groups as specific signature probe sets (SPSs), and we defined SPSs for each of the 35 pathogen genomes represented on the array (Table 2).

TABLE 2

Each pathogen signature probe set (SPS) comprise its probes with AES in the top 20$^{th}$ percentile [column (1)]. Probes that do not have GC between 40-60% [column (2)] or high similarity to human genome [column (3)] were removed. Probes derived from other pathogens which will cross-hybridize to the pathogen based on HD and MCM [column (4)] were added to the SPS [column (5)].

| | Pathogen | Family | Total tiling probes | AES (1) | GC content filter (2) | Human Genome filter (3) | No. of filtered probes left | No. of predicted cross-hybridizing probes (HD ≦ 4 and MCM ≧ 18) (4) | No. of probes in SPS (5) |
|---|---|---|---|---|---|---|---|---|---|
| 1 | LCMV | Arenaviridae | 1283 | 574 | 1 | 18 | 555 | 0 | 555 |
| 2 | Hantaan | Bunyaviridae | 834 | 131 | 6 | 22 | 103 | 2 | 105 |
| 3 | Sin Nombre | Bunyaviridae | 837 | 225 | 8 | 29 | 188 | 3 | 191 |
| 4 | 229E | Coronaviridae | 3495 | 196 | 2 | 12 | 182 | 2 | 184 |
| 5 | OC43 | Coronaviridae | 3937 | 663 | 16 | 43 | 604 | 3 | 607 |
| 6 | SARS | Coronaviridae | 3805 | 672 | 6 | 78 | 588 | 3 | 591 |
| 7 | Dengue serotype 1 | Flaviviridae | 1370 | 201 | 2 | 47 | 152 | 50 | 202 |
| 8 | Dengue serotype 2 | Flaviviridae | 1370 | 178 | 0 | 36 | 142 | 71 | 213 |
| 9 | Dengue serotype 3 | Flaviviridae | 1370 | 336 | 1 | 51 | 284 | 69 | 353 |
| 10 | Dengue serotype 4 | Flaviviridae | 1361 | 172 | 1 | 41 | 130 | 44 | 174 |
| 11 | Japanese encephalitis | Flaviviridae | 1404 | 274 | 6 | 64 | 204 | 40 | 244 |
| 12 | West Nile | Flaviviridae | 1401 | 111 | 4 | 22 | 85 | 22 | 107 |
| 13 | Yellow Fever | Flaviviridae | 1389 | 151 | 0 | 6 | 145 | 10 | 155 |
| 14 | Hepatitis B | Hepadnaviridae | 409 | 146 | 2 | 10 | 134 | 0 | 134 |
| 15 | Influenza A | Orthomyxoviridae | 1582 | 601 | 2 | 46 | 553 | 0 | 553 |
| 16 | Influenza B | Orthomyxoviridae | 1822 | 718 | 7 | 69 | 642 | 2 | 644 |
| 17 | Human papillomavirus type 10 | Papillomaviridae | 1011 | 177 | 1 | 7 | 169 | 0 | 169 |
| 18 | hMPV | Paramyxoviridae | 1705 | 375 | 23 | 60 | 292 | 8 | 300 |
| 19 | Newcastle disease | Paramyxoviridae | 1943 | 252 | 0 | 8 | 244 | 0 | 244 |
| 20 | Nipah | Paramyxoviridae | 2335 | 274 | 22 | 17 | 235 | 0 | 235 |
| 21 | Parainfluenza 1 | Paramyxoviridae | 1995 | 625 | 13 | 62 | 550 | 3 | 553 |
| 22 | Parainfluenza 2 | Paramyxoviridae | 2002 | 838 | 31 | 45 | 762 | 0 | 762 |
| 23 | Parainfluenza 3 | Paramyxoviridae | 1979 | 834 | 29 | 104 | 701 | 9 | 710 |

TABLE 2-continued

Each pathogen signature probe set (SPS) comprise its probes with
AES in the top 20$^{th}$ percentile [column (1)]. Probes that do not have GC
between 40-60% [column (2)] or high similarity to human genome [column (3)]
were removed. Probes derived from other pathogens which will cross-hybridize
to the pathogen based on HD and MCM [column (4)] were added to the SPS
[column (5)].

| | Pathogen | Family | Total tiling probes | AES (1) | GC content filter (2) | Human Genome filter (3) | No. of filtered probes left | No. of predicted cross-hybridizing probes (HD ≦ 4 and MCM ≧ 18) (4) | No. of probes in SPS (5) |
|---|---|---|---|---|---|---|---|---|---|
| 24 | RSV B | Paramyxoviridae | 1948 | 655 | 52 | 66 | 537 | 4 | 541 |
| 25 | Echovirus 1 | Picornaviridae | 945 | 439 | 3 | 72 | 364 | 59 | 423 |
| 26 | Enterovirus A | Picornaviridae | 946 | 205 | 0 | 9 | 196 | 21 | 217 |
| 27 | Enterovirus B | Picornaviridae | 944 | 109 | 0 | 15 | 94 | 47 | 141 |
| 28 | Enterovirus C | Picornaviridae | 945 | 202 | 0 | 19 | 183 | 31 | 214 |
| 29 | Enterovirus D | Picornaviridae | 944 | 191 | 0 | 16 | 175 | 15 | 190 |
| 30 | Foot and mouth disease | Picornaviridae | 1036 | 356 | 26 | 5 | 325 | 0 | 325 |
| 31 | Hepatitis A | Picornaviridae | 955 | 355 | 9 | 37 | 309 | 0 | 309 |
| 32 | Rhinovirus A (type 89) | Picornaviridae | 913 | 333 | 2 | 48 | 283 | 13 | 296 |
| 33 | Rhinovirus B | Picornaviridae | 920 | 464 | 3 | 35 | 426 | 11 | 437 |
| 34 | HIV 1 | Retroviridae | 1174 | 229 | 4 | 17 | 208 | 0 | 208 |
| 35 | Rubella | Togaviridae | 1246 | 748 | 534 | 3 | 211 | 0 | 211 |
| | Total | | 53555 | | | | 10955 | | 11497 |

Each pathogen's SPS comprised tiling probes derived from its genome sequence (HD=0, MCM=40), as well as cross-hybridizing probes derived from other pathogens (HD=4, MCM=18).

We next considered other non-specific hybridization phenomena that could affect performance of our SPS probes. For example, we observed a general relationship between probe signal and % GC content. Consistent with previous observations, we found that probes<40% GC resulted in diminished signal intensities, while probes>60% GC content showed higher signal intensities (Wong et al. 2004; Maskos and Southern, 1993). Thus, we utilized % GC content as an additional selection filter, whereby probes with <40% GC and >60% GC were excluded from our SPSs, despite optimal HD and MCM values.

Sequence Similarity to Human: Genome

In case the target-nucleic acid to be detected is extracted from humans (for example, human samples containing viral genomes), probes with high homology to the human genome should also be avoided. Accordingly, for any probe $s_a$ of length-m specific for the target nucleic acid $v_a$, the probe $s_a$ is selected if it does not have any hits with any region of a nucleic acid different from the target nucleic acid, and if the probe $s_a$ length-m has hits with the nucleic acid different from the target nucleic acid, the probe $s_a$ length-m with the smallest maximum alignment length and/or with the least number of hits is selected. In particular, for any length-m probe $s_a$, hits of $s_a$ with the human genome are found with the BLAST algorithm (Altschul, S. F., et al., 1997). A BLAST word size of (W=15) and an expectation value of 100 was used to find all hits. $s_a$ is selected if it does not have any hits with the human genome, that is, it is specific to $v_a$. However, if all length-m substrings of $v_a$ have hits with the human genome, those with the smallest maximum alignment length and with the least number of hits was selected.

Furthermore, as cross-hybridization with human sequences could also confound results, we compared all probes to the human genome assembly (build 17) (International Human Genome Sequencing Consortium. Initial sequencing and analysis of the human genome. Nature 409 (6822), 860-921 (2001).) by BLAST using a word size of 15 (Altschul et al. 1997). Probes with expectation value of 100 were further filtered from the SPSs (see Table 2 above).

Accordingly, the present Invention provides a method of designing oligonucleotide probe(s) for nucleic acid detection, wherein for any probe $s_a$ of length-m specific for the target nucleic acid $v_a$, the probe $s_a$ is selected if it does not have any hits with any region of a nucleic acid different from the target nucleic acid, and if the probe $s_a$ length-m has hits with the nucleic acid different from the target nucleic acid, the probe $s_a$ length-m with the smallest maximum alignment length and/or with the least number of hits is selected.

Further, the design of the oligonucleotide probe(s) may be also carried out by AES according to the invention. In particular, the invention provides a method of selecting and/or designing probes wherein a probe $p_i$ at position i of a target nucleic acid is selected if $p_i$ is predicted to hybridize to the position i of the amplified target nucleic acid.

In particular, the oligonucleotide probe(s) capable of hybridizing to the selected region(s) may be selected and/or designed according to at least one of the following criteria:

(a) the selected probe(s) has a CG-content from 40% to 60%;

(b) the probe(s) is selected by having the highest free energy computed based on Nearest-Neighbor model;

(c) given probe $s_a$ and probe $s_b$ substrings of target nucleic acids $v_a$ and $v_b$, $s_a$ is selected based on the hamming distance between $s_a$ and any length-m substring $s_b$ from the target nucleic acid $v_b$ and/or on the longest common substring of $s_a$ and probe $s_b$;

(d) for any probe $s_a$ of length-m specific for the target nucleic acid $v_a$, the probe $s_a$ is selected if it does not have any hits with any region of a nucleic acid different from the target nucleic acid, and if the probe $s_a$ length-m has hits with the nucleic acid different from the target nucleic acid, the probe $s_a$ length-m with the smallest maximum alignment length and/or with the least number of hits is selected; and/or (e) a probe $p_i$ at position i of a target nucleic acid is selected if $p_i$ is predicted to hybridize to the position i of the amplified target nucleic acid.

According to a particular aspect of the invention, two or more of the criteria indicated above may be used for designing the oligonucleotide probe(s). For example, the probe(s) may be designed by applying all criteria (a) to (e). Other criteria, not explicitly mentioned herein but which are evident to a skilled person in the art may also be used.

In particular, under the criterion (e), a probe $p_i$ at position i of a target nucleic acid $v_a$ is selected if $P(p_i|v_a) \geq \lambda$, wherein $\lambda$ is 0.5 and $P(p_i|v_a)$ is the probability that $p_i$ has to hybridize to the position i of the target nucleic acid $v_a$. More in particular, $\lambda$ is 0.8.

According to another aspect, the invention provides a method as above described wherein $$P(p_i | v_a) \approx P(X \leq x_i) = \frac{c_i}{k},$$

wherein X is the random variable representing the amplification efficiency score (AES) values of all probes of $v_a$, k is the number of probes in $v_a$, and $c_i$ is the number of probes whose AES values are $\leq x_i$.

According to another aspect, the AES can also be used to design random primer tags to facilitate random amplification of sample by random PCR (for use in applications such as detection of pathogens, detection of gene expression, constructing clonal DNA libraries, and other applications a skilled person would employ random PCR).

Synthesis of Oligonucleotide Probes on a Support

According to another aspect of the invention, the method of selecting and/or designing at least one oligonucleotide probe(s) as described above further comprises a step of preparing the selected and/or designed probe(s). Designing a probe comprises understanding its sequence and/or designing it by any suitable means, for example by using a software. The step of preparing the probe comprises the physical preparation of it. The probe may be prepared according to any standard method known in the art. For example, the probes may be chemically synthesized or prepared by cloning. For example as described in Sambrook and Russel, 2001.

There is also provided a support, for example a microarray or biochip, prepared according to any embodiment according to the present invention.

The probe(s) designed and prepared according to any method of the present invention may used in solution or may be placed on an insoluble support. For example, may be applied, spotted or printed on an insoluble support according to any technique known in the art. The support may be a solid support or a gel. The support with the probes applied on it, may be a microarray or a biochip.

More in particular, the present invention provides an oligo microarray hybridization-based approach for the rapid detection and identification of pathogens, for example viral and/or bacterial pathogens, from PCR-amplified cDNA prepared from primary tissue samples. In particular, from random PCR-amplified cDNA(s).

In the following description, the preparation of probes is made with particular reference to a microarray. However, the support, as well as the probes, may be prepared according to any description across the whole content of the present application. In particular, an "array" is an intentionally created collection of molecules which may be prepared either synthetically or biosynthetically. The molecules in the array may be identical or different from each other. The array may assume a variety of formats, e.g., libraries of soluble molecules; libraries of compounds tethered to resin beads, silica chips, or other solid supports. Array Plate or a Plate is a body having a plurality of arrays in which each array is separated from the other arrays by a physical barrier resistant to the passage of liquids and forming an area or space referred to as a well.

Sample Preparation and Hybridization onto the Microarray

The biological sample may be any sample taken from a mammal, for example from a human being. The biological sample may be blood, a body fluid, saliva, urine, stool, and the like. The biological sample may be treated to free the nucleic acid comprised in the biological sample before carrying out the amplification step. The target nucleic acid may be any nucleic acid which is intended to be detected. The target nucleic acid to be detected may be at least a nucleic acid exogenous to the nucleic acid of the biological sample. Accordingly, if the biological sample is from a human, the exogenous target nucleic acid to be detected (if present in the biological sample) is a nucleic acid which is not from human origin. According to an aspect of the invention, the target nucleic acid to be detected is at least a pathogen genome or fragment thereof. The pathogen nucleic acid may be at least a nucleic acid from a virus, a parasite, or bacterium, or a fragment thereof.

According to an aspect of the present invention, there is provided a method of target nucleic acid detection analysis. The target nucleic acid(s) from; a biological sample desired to be detected may be any target nucleic acid, RNA and/or DNA. For example, mRNA and/or cDNA. More in particular, the target nucleic acid to be detected may be a pathogen or non-pathogen. For example, It may be the genome or a fragment thereof of at least one virus, at least one bacterium and/or at least one parasite. The probes selected and/or prepared may be placed, applied and/or fixed on a support according to any standard technology known to a skilled person in the art. The support may be an insoluble support, for example a solid support. In particular, a microarray and/or a biochip.

According to a particular example, RNA and DNA was extracted from patient samples e.g. tissues, sera, nasal pharyngeal washes, stool using established protocols and commercial kits. For example, Qiagen Kit for nucleic acid extraction may be used. Alternatively, Phenol/Chloroform may also be used for the extraction of DNA and/or RNA. Any technique known in the art, for example as described in Sambrook and Russel, 2001 may be used. RNA was reverse-transcribed to cDNA using tagged random primers, based on a protocol described by Bohlander et. al., 1992 and Wang et. al., 2003. The cDNA was then amplified by random PCR. Fragmentation, labeling and hybridization of sample to the microarray were carried out as described by Wong et. al., 2004.

Microarray Synthesis

According to a particular experiment described in the Examples section, the present inventors selected several viral genomes representing the most common causes of viral disease in Singapore. Using the complete genome sequences downloaded from Genbank, 40-mer probes which tiled across the entire genomes and overlapping at five-base resolution were generated. Seven replicates of each virus probe were synthesized directly onto the microarray using Nimblegen technology (Nuwaysir, E. F., et al., 2002). The probes were randomly distributed on the microarray to minimize the effects of hybridization artifacts. To control for non-specific hybridization of sample to probes, 10,000 oligonucleotide probes were designed and synthesized onto the microarray. These 10,000 oligonucleotides did not have any sequence similarity to the human genome, or to the pathogen genomes. They were random probes with 40-60% CG-content. These probes measured the background signal intensity. As a positive control, 400 oligonucleotide probes to human genes which have known or inferred functions in immune response were synthesized on the array. A plant virus, PMMV, was included as a negative control, for a total of approximately 380,000 probes. In the following description, the invention will be described in more particularity with reference to a pathogen detection chip analysis (also referred to as PDC). However, the analysis (method) is not limited to this particular embodiment, but encompasses the several aspects of the invention as described across the whole content of the present application.

Method of Detecting Target Nucleic Acid(s)

According to another aspect, the present invention provides a method of detecting at least one target nucleic acid comprising the step of:

(i) providing a biological sample;

(ii) amplifying nucleic acid(s) comprised in the biological sample;

(iii) providing at least one oligonucleotide probe capable of hybridizing to at least one target nucleic acid, if present in the biological sample, wherein the probe(s) is prepared by using a method according to any aspect of the invention herein described;

(iv) contacting the probe(s) with the amplified nucleic acids and detecting the probe(s) hybridized to at least one target nucleic acid.

The amplification step (ii) may be carried out in the presence of random, partially random (that is, comprising a fixed portion and a random portion) or specific primers. In particular, the amplification step (II) may be carried out in presence of at least one random primer. More in particular, in the presence of at least one random forward primer and/or at least one random reverse primer. For example, the amplification step (ii) may be carried out in the presence of more than two random primers. Any amplification method known in the art may be used. For example, the amplification method is a RT-PCR.

In particular, the present inventors developed a method of detecting the probe(s) hybridized to the to the target nucleic acid based on the amplification efficiency score (AES). This may herein also be referred to as the algorithm according to the present invention. In particular, a forward random primer binding to position i and a reverse random primer binding to position j of a target nucleic acid $v_a$ are selected among primers having an amplification efficiency score (AES$_i$) for every position i of a target nucleic acid $v_a$ of:

$$AES_i = \sum_{j=i-Z}^{i} \left\{ P^f(j) \times \sum_{k=\max(i+1, j+500)}^{j+Z} P^r(k) \right\},$$

wherein $$\sum_{k=\max(i+1, j+500)}^{j+Z} P^r(k) = P^r(i+1) + P^r(i+2) + \ldots P^r(j+Z)$$

$P^f(i)$ and $P^r(i)$ are the probabilities that a random primer $r_i$ can bind to position i of $v_a$ as forward primer and reverse primer, respectively, and $Z \leq 10000$ bp is the region of $v_a$ desired to be amplified. More in particular, Z may be $\leq 5000$ bp, $\leq 1000$ bp, or $\leq 500$ bp.

The amplification step may comprise forward and reverse primers, and each of the forward and reverse primers may comprise, in a 5'-3' orientation, a fixed primer header and a variable primer tail, and wherein at least the variable tail hybridizes to a portion of the target nucleic acid $v_a$. In particular, the amplification step may comprise forward and/or reverse random primers having the nucleotide sequence of any of SEQ ID NOS:1-7, or a variant, or derivative thereof.

The biological sample may be any sample taken from a mammal, for example from a human being. The biological sample may be tissue, sera, nasal pharyngeal washes, saliva, any other body fluid, blood, urine, stool, and the like. The biological sample may be treated to free the nucleic acid comprised in the biological sample before carrying out the amplification step. The target nucleic acid may be any nucleic acid which is intended to be detected. The target nucleic acid to be detected may be at least a nucleic acid exogenous to the nucleic acid of the biological sample. Accordingly, if the biological sample is from a human, the exogenous target nucleic acid to be detected (if present in the biological sample) is a nucleic acid which is not from human origin. According to an aspect of the invention, the target nucleic acid to be detected is at least a pathogen genome or fragment thereof. The pathogen nucleic acid may be at least a nucleic acid from a virus, a parasite, or bacterium, or a fragment thereof.

Accordingly, the invention provides a method of detection of at least a target nucleic acid, if present, in a biological sample. The method may be a diagnostic method for the detection of the presence of a pathogen into the biological sample. For example, if the biological sample is obtained from a human being, the target nucleic acid, if present in the biological sample, is not from human.

The probe(s) designed and/or prepared according to any method of the present invention may used in solution or may be placed on an insoluble support. For example, may be applied, spotted or printed on an insoluble support according to any technique known in the art. The support with the probes applied on it may be a solid support or a gel. In particular, it may be a microarray or a biochip.

The probes are then contacted with the nucleic acid of the biological sample, and if present the target nucleic acid(s) and the probe(s) hybridize, and the presence of the target nucleic acid is detected. In particular, in the detection step (iv), the mean of the signal intensities of the probes which hybridize to $v_a$ is statistically higher than the mean of the probes $\notin v_a$, thereby indicating the presence of $v_a$ In the biological sample.

More in particular, in the detection step (iv), the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$ in the biological sample.

For example, in the detection step (iv), the presence of a target nucleic acid in a biological sample is given by a value of t-test≦0.1 and/or Anderson-Darling test value≦0.05 and/or a value of Weighted Kullback-Leibler divergence of ≧1.0, preferably ≧5.0. In particular, the t-test value is ≦0.05.

According to another aspect, the present invention provides a method of determining the presence of a target nucleic acid $v_a$ comprising detecting the hybridization of a probe to a target nucleic acid $v_a$ and wherein the mean of the signal intensities of the probes which hybridize to $v_a$ is statistically higher than the mean of the probes $\notin v_a$, thereby indicating the presence of $v_a$. In particular, the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$. More in particular, the presence of a target nucleic acid in a biological sample is given by a value of t-test≦0.1 and/or Anderson-Darling test value≦0.05 and/or a value of Weighted Kullback-Leibler divergence of ≧1.0; preferably, ≧5.0. For example, the t-test value may be ≦0.05.

According to another aspect, the present invention provides a method of detecting at least one target nucleic acid, comprising the steps of:
(i) providing at least one biological sample;
(ii) amplifying nucleic acid(s) comprised in the biological sample;
(iii) providing at least one oligonucleotide probe capable of hybridizing to at least one target nucleic acid, if present in the biological sample;
(iv) contacting the probe(s) with the amplified nucleic acids and detecting the probe(s) hybridized to target nucleic acid(s), wherein the mean of the signal intensities of the probes which hybridize to $v_a$ is statistically higher than the mean of the probes $\notin v_a$, thereby indicating the presence of $v_a$ in the biological sample.

In step (iv), the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$ in the biological sample. In particular, in step (iv) the presence of a target nucleic acid in a biological sample is given by a value of t-test≦0.1 and/or Anderson-Darling test value≦0.05 and/or a value of Weighted Kullback-Leibler divergence of ≧1.0, preferably ≧5.0. The t-test value may be ≦0.05. The nucleic acid to be detected is nucleic acid exogenous to the nucleic acid of the biological sample. The target nucleic acid to be detected may be at least a pathogen genome or fragment thereof. The pathogen nucleic acid may be at least a nucleic acid from a virus, a parasite, or bacterium, or a fragment thereof. In particular, when the sample is obtained from a human being, the target nucleic acid, if present in the biological sample, is not from the human genome. The probes may be placed on an insoluble support. The support may be a microarray or a biochip.

Test Using the Template Sequence of RSV B

To verify if the variation in signal intensities displayed by different regions of a virus has direct correlation with their corresponding amplification efficiency scores, a total of five microarray experiments were performed on a common pathogen affecting human, the human respiratory syncytial virus B (RSV B).

Next, the probe design criteria, as described above, were applied on the template sequence of RSV B obtained from NCBI (NC_001781). This resulted in 1948 probes spotted onto each microarray. The amplification efficiency map for RSV B was also computed prior to the actual experiments and shown in FIG. 2. This figure shows the peaks having the AES higher than the average AES and indicating the regions of the RSV B with higher probability of amplification.

Using 5 samples containing the human respiratory syncytial virus B (RSV B), independent microarray experiments were conducted. The resultant signal intensities for one such experiment is shown in FIG. 3.

For each experiment, the signal intensities of the 1948 probes were ranked in decreasing order and were correlated with their corresponding AES value. The p-value was found to be $<2.2e^{-16}$ on the average. This indicates that the correlation between the signal intensity of probe at position i of RSV B with $AES_i$ is not at all random. Further investigations revealed that about 300 probes, which consistently produced high signal intensities in all five experiments, have amplification efficiency scores in the $90^{th}$ percentile level.

Having shown that the described amplification efficiency model works well on the RSV B genome, it was desired to show that the model according to the invention may be extended to other viral genomes as well. Another microarray experiment was performed on the human metapneumonia virus (HMPV). This time, there were 1705 probes on the microarray. Again, the amplification efficiency map for HMPV was computed. In this experiment, the correlation test between signal intensities and amplification efficiency scores gave a p-value of $1.335e^{-9}$.

Accordingly, the amplification efficiency model according to the invention is able to predict the relative strength of signals produced by different regions of a viral genome in the described experiment set-up. Probes from regions with low amplification efficiency scores have a high tendency to produce no or low signal intensities. This would result in a false negative on the microarray. Such probes will complicate the analysis of the microarray data and this is made even more complicated since a probe with a low signal intensity may be due to its target genome not being present or simply that it was not amplified. As such, probes in regions with reasonably high amplification efficiency scores should be selected to minimize inaccuracies caused by the RT-PCR process using random primers.

The threshold for amplification efficiency scores for probe selection for a virus $v_a$ is determined by the cumulative distribution function of the AES values $v_a$. Let X be the random variable representing the AES values of all probes of $v_a$. Let k be the number of probes in $v_a$. Then, we denote the probability that the AES value is less than or equal to x be $$P(X \leq x) = \frac{c}{k},$$

where c is the number of probes which have AES values less than or equal to x. For a probe $p_i$ at position l of $v_a$ let $x_i$ be its corresponding AES value. Since the signal intensity of a probe is highly correlated to its AES value, we estimate $P(p_i|v_a)$, the probability that $p_i$ has high signal intensity in the presence of $v_a$, to be $P(X \leq x_i)$. Thus, $$P(p_i | v_a) \approx P(X \leq x_i) = \frac{c_i}{k}$$

where $c_i$ is the number of probes whose AES values are less than or equal to $x_i$. For probe selection, probe $p_i$ is selected if $P(p_i|v_a) > \lambda$. In the present experiments, $\lambda$ was set as $\lambda = 0.8$.

Accordingly, the present invention also provides a method of probe design and/or of target nucleic acid detection wherein a probe $p_i$ at position i of a target nucleic acid $v_a$ is selected if $P(p_i|v_a) > \lambda$, wherein is 0.75 and $P(p_i|v_a)$ is the probability that $p_i$ has a high signal intensity in the presence of $v_a$. More in particular, $$P(p_i | v_a) \approx P(X \leq x_i) = \frac{c_i}{k},$$

wherein X is the random variable representing the amplification efficiency score (AES) values of all probes of $v_a$, k is the number of probes in $v_a$, and $c_i$ is the number of probes whose AES values are less than or equal to $x_i$.

Target Nucleic Acid Detection Analysis

In the following description, the invention will be described in more particularity with reference to a pathogen detection chip analysis (also referred to as PDC). However, the analysis (method) is not limited to this particular embodiment, but encompasses the several aspects of the invention as described across the whole content of the present application. Therefore, in particular, given a PDC with a set of length-m probes $P = \{p_1, p_2, \ldots, p_i\}$, which is designed for a set of viral genomes $V = \{v_1, v_2, \ldots, v_n\}$, the pathogen detection chip analysis problem is to detect the virus present in the sample based on the chip data. The chip data here refers to the collective information provided by the probe signals on the PDC. Thus, the chip data $D = \{d_1, d_2, \ldots d_x\}$ is the set of corresponding signals of the probe set P on the PDC.

Given a sample, it is not known what pathogens are present in the sample, how many different pathogens there are, if present at all. However, if a virus $v_a$ is indeed in the sample, then the signal intensities of the probes of $v_a$ should differ significantly from the signal intensities of probes from other viruses. Specifically, a higher proportion of probes of $v_a$ should have high signal intensities compared to other viruses. Hence, it would be expected that the mean of the signal intensities of the probes in $v_a$ should be statistically higher than that of probes $\notin v_a$.

Accordingly, the invention provides a method wherein the mean of the signal intensities of the probes which hybridize to $v_a$ is statistically higher than the mean of the probes $\notin v_a$, which may indicate the presence of $v_a$ in the biological sample.

However, having a statistically higher mean may still be insufficient to conclude that $v_a$ is in the sample. Preferably, an additional step may be required. We need to compute the relative difference of the proportion of probes $\notin v_a$ having high signal intensities to the proportion of probes on the PDC having high signal intensities. This is based on the observation that the distribution of the signal intensities of probes $\in v_a$ is more positively skewed than that of probes $\notin v_a$ (see the arrow in FIG. 4 A. For comparison see FIG. 4B).

Based the above observations, the chip data D for the presence of viruses was analyzed as follows. For every virus $v_a \in V$, we used a one-tail t-test (Goulden, C. H., 1956) to determine if the mean of the signal intensities of the probes $\in v_a$ was statistically higher than that of the signal intensities of the probes $\notin v_a$. Thus, the t-statistic was computed:

$$t_i = \frac{\mu_a - \mu_{a'}}{\sqrt{\frac{s_a^2}{n_a} + \frac{s_{a'}^2}{n_{a'}}}}$$

where $\mu_a$, $\sigma_a^2$ and $n_a$ is the mean, variance, and size of the signal intensities of the probes $\in v_a$ respectively and $\mu_{a'}$, $s_{a'}^2$, and $n_{a'}$ is the mean, variance, and size of the signal intensities of the probes $\notin v_a$ respectively.

To test the significance of the difference, the level of significance was set to 0.05. This means that the hypothesis that the mean of the signal intensities of the probes $\in v_a$ is higher than that of the signal intensities of the probes $\notin v_a$ would only be accepted if the p-value of $t_a < 0.05$. In this case, $v_a$ is likely to be present in the sample.

The t-test alone, which allows the inventors to know if the distribution of the signal intensities of a virus is different from that of other viruses, may not be sufficient to determine if a particular virus is in the sample. It is also essential to know how similar or different the two distributions are. A ruler that can be used to measure the similarity between a true distribution and a model distribution is the Kullback-Leiber divergence (Kullback and Leiber, 1951) (also known as the relative entropy). In this application, the probability distribution of the signal intensities of the probes in $v_a$ is the true distribution while the probability distribution of the signal intensities of all the probes in P is the model distribution. Let $P_a$ be the set of probes in $v_a$. The Kullback-Leibler (KL) divergence of the probability distribution of the signal intensities of $P_a$ and P is:

$$KL(P_a \| P) = \sum_{\mu \leq x \leq \max(D)} f_a(x) \log\left(\frac{f_a(x)}{f(x)}\right)$$

where $\mu$ is the mean signal intensity of the probes in P; $f_a(x)$ is the fraction of probes in $P_a$ with signal intensity x; and $f(x)$ is the fraction of probes in P with signal intensity x. It follows that if $KL(P_a\|P) = 0$ then the probability distribution of $P_a$ is exactly the same as that of P. Otherwise they are different.

Since a virus that is present in the sample would have signal intensities higher than that of the population, this implies that $v_a$ has a chance of being present in the sample if $KL(P_a\|P) > 0$. Thus, the larger the value of $KL(P_a\|P)$, the more different are the two probability distributions and the more likely that $v_a$ is indeed present in the sample.

It is important to note that the Kullback-Leibler divergence is the collective difference over all x of two probability distributions. Thus, while the Kullback-Leibler divergence is good at finding shifts in a probability distribution, it is not always so good at finding spreads, which affect the tails of the probability distribution more. As described in FIG. 4(A,B), the tails of the probability distribution provides the most information about whether a virus is present in the sample. Hence, the Kullback-Leibler divergence statistic must be improved to reflect more accurately such an observation.

To increase its sensitivity out on the tails, we introduced a stabilized or weighted statistic to the Kullback-Leibler divergence, the Anderson-Darling statistic (Stephens, M. A.

(1974). EDF Statistics for Goodness of Fit and Some Comparisons, Journal of the American Statistical Association, Vol. 69, pp. 730-737). Thus the Weighted Kullback-Leibler divergence (WKL) is:

$$WKL(P_a \| P) = \sum_{\mu \leq x \leq \max(D)} \frac{f_a(x) \log \frac{f_a(x)}{f(x)}}{\sqrt{Q(x)[1-Q(x)]}}$$

where Q(x) is the cumulative distribution function of the signal intensities of the probes in P.

Empirical tests show that in samples where there are no viruses, viruses that pass the t-test with significance level 0.05 have WKL<5.0. In samples where there is indeed a virus present, the actual viruses not only pass the t-test with significance level 0.05 but are also the only viruses to have WKL≧5.0. Thus we set the Weighted Kullback-Leiber divergence threshold for a virus to be present in the sample to be 5.0. This analysis framework is shown in FIG. 5.

Apparatus and/or Product Performing the Method According to the Invention

It is well-known to a skilled person in the art how to configure software which can perform the algorithms and/or methods provided in the present invention. Accordingly, the present invention also provides a software and/or a computer program product configured to perform the algorithms and/or methods according to any embodiment of the present invention There is also provided at least one electronic storage medium. The electronic storage medium may be a computer hard-drive, a CD-ROM, a flash memory device (e.g. USB thumbdrive), a floppy disk, or any other electronic storage medium in the art. The software may be run on personal computers, mainframes, and any computing processing unit, and the particular configurations are known to a person skilled in the art.

It will be appreciated that the present invention has been described by way of example only and that various modifications in design may be made without departure from the spirit and scope of the invention.

Having now generally described the invention, the same will be more readily understood through reference to the following examples, which are provided by way of illustration, and are not intended to be limiting of the present invention.

EXAMPLES

Standard molecular biology techniques known in the art and not specifically described were generally followed as described Sambrook and Russel, Molecular Cloning: A Laboratory Manual, Cold Springs Harbor Laboratory, New York (2001).

Microarray Synthesis

We selected 35 viral genomes representing the most common causes of viral disease in Singapore (see Table 1 above).

Complete genome sequences were downloaded from NCBI Taxonomy Database (http://www.ncbi.nlm.nih.gov/Taxonomy/taxonomyhome.html/) to generate 40-mer probe sequences tiled across the entire genomes and overlapping at an average 8-base resolution. 7 replicates of each virus probe was synthesized directly onto the microarray using Nimblegen proprietary technology (Nuwaysir et al. 2002). The probes were randomly distributed on the microarray to minimize the effects of hybridization artifacts. To control for non-specific hybridization of sample to probes and measure background signal, 10,000 oligonucleotide probes were designed and synthesized onto the microarray. They are random probes with 40-60% GC-content with no sequence similarity to the human genome, or to the pathogen genomes. As a positive control, 400 oligonucleotide probes to human genes which have known or inferred functions in immune response were synthesized on the array. A plant virus, PMMV, was included as negative control, for a total of 390,482 probes.

Sample Preparation, Microarray Hybridization and Staining

Dengue cell line (ATCC #VR-1254) was cultured as per ATCC recommendations and Sin850 SARS cell line was cultured as described (Vega et al. 2004). Clinical, specimens (nasopharyngeal washes) were obtained from an Indonesian pediatric population and stored at −80° C. in RNAzol (Leedo Medical Laboratories Inc., Friendswood Tex.). All were suspected patients aged between 7 to 38 months demonstrating specific clinical signs of respiratory illnesses. RNA was extracted with RNAzol according to manufacturer's instructions (Smalling et al. 2002; Tang et al. 1999). Extracted RNA was resuspended in RNA storage solution (Ambion, USA) and stored at −80° C. until needed. RNA was reverse transcribed to cDNA using tagged random primers, based on a protocol described by Bohlander et al and Wang et al (Wang et al. 2002; Bohlander et al. 1992). The cDNA was then amplified by random PCR, fragmented, end-labeled with biotin labeling, hybridized onto the microarray and stained as previously described (Wong et al. 2002). In our initial experiments, we found that probe GC content could create artifacts in signal intensity measurements, with increasing signal directly proportional to probe GC content. Adding 0.82 M TMAC to Nimblegen's proprietary TMAC hybridization buffer eliminated this artifact.

Real-Time Diagnostic RT-PCR for RSV and hMPV

A 20 µl reaction mixture containing 2 µl of the purified patient RNA, 5 U of MuLV reverse transcriptase, 8 U of recombinant RNase inhibitor, 10 µl of 2×universal PCR Master Mix with no UNG (all from Applied Biosystems) 0.9 µM primer and 0.2 µM probe. The real-time RT-PCRs were carried out in an ABI Prism 7900HT Sequence Detection System (Applied Biosystems). RT was performed at 48° C. for 30 min followed by 10 min at 95° C. for activation of DNA polymerase. Amplification of RT products achieved by 40 cycles of 15 s at 95° C. and 1 min at 60° C. Negative controls and serial dilutions of a plasmid clone (positive control) were included in every PCR assay. During amplification, fluorescence emissions were monitored at every thermal cycle. The threshold (CT) represents the cycle at which significant fluorescence is first detected. CT value was converted to copy number using a control plasmid of known concentration. For RSV, $2.61 \times 10^9$ copies ha a CT value of 11.897 while for hMPV, $7.51 \times 10^9$ copies had a CT value of 10.51.

1-Step Diagnostic RT-PCR for Coronavirus and Rhinovirus

Frozen live cultures of human coronavirus OC43, 229E and rhinovirus 16 were purchased from ATCC (Cat #VR-1558, VR-740, VR-283) for use as positive controls. RNA was extracted from these cultures using RNA Mini Kit (Qiagen, Germany) in accordance with manufacturer's instructions. The samples were amplified as previously described using the following diagnostic primer pairs: pan-coronavirus (Cor-FW, Cor-RV), OC43 (OC43-FW, OC43-RV), 229E (229E-FW, 229E-RV), rhinovirus (Amplimer 1, Amplimer 2) (Moës et al. 2005; Deffernez et al. 2004).

Analysis of Pathogen Microarray Data

Our Pathogen Microarray contains a set of 40-mer probes $P=\{p_1, p_2, \ldots, p_s\}$, binned into distinct probe hybridization signatures for 35 viral genomes $V=\{v_1, v_2, \ldots, v_{35}\}$. Upon hybridization of pathogen nucleic acids, a set of probe signal intensity data D={$d_1, d_2, \ldots, d_s$} corresponding to probe set P is generated.

1-Tail T-Test

If virus $v_a$ is present, then probes comprising its hybridization signature (probes $\in v_a$) should have statistically higher signal intensities than probes $\notin v_a$ determined by the t-statistic (1-tail T-test):

$$t_i = \frac{\mu_a - \mu_{a'}}{\sqrt{\frac{s_a^2}{n_a} + \frac{s_{a'}^2}{n_{a'}}}}$$

where $\mu_a$, $\sigma_a^2$ and $n_a$ are the mean, variance, and size of the signal intensities of the probes $\in v_a$ respectively and $\mu_{a'}$, $s_{a'}^2$ and $n_{a'}$ are the mean, variance, and size of the signal intensities of the probes $\notin v_a$ respectively.

The level of significance was set to 0.05. This means that we would only accept the hypothesis that the mean of the signal intensities of the probes $\in v_a$ is higher than that of the signal intensities of the probes $\notin v_a$ if the p-value of $t_a$<0.05. In this case, $v_a$ is likely to be present in the sample. However, the T-test method of detection results in many false positive calls.

PDA v. 1

PDA v.1 comprises a series of statistical tests, beginning with a Weighted Kullback-Leibler test and Z-score transformation (WKL score) followed by Anderson-Darling test for normality.

Consider the virus $v_a$. Let $P_a$ be the set of probes of a virus $v_a$ and $\overline{P_a}$=P–$P_a$. Let [$r_{low}$, $r_{high}$] be the signal intensity range. We partitioned it into c bins $$\left[r_{low} + j\left(\frac{r_{high} - r_{low}}{c}\right), r_{low} + (j+1)\left(\frac{r_{high} - r_{low}}{c}\right)\right]$$

for j=0, 1, . . . , c–1. The unmodified Kullback-Leibler divergence may be computed by $$KL(P_a | \overline{P_a}) = \sum_{j=0}^{c-1} f_a(j)\log\left(\frac{f_a(j)}{f_{\bar{a}}(j)}\right)$$

where $n_a^j$ and $n_{\bar{a}}^j$ are the number of probes in $P_a$ and probes in $\overline{P_a}$ contained in the bin $b_j$ respectively.

$$f_a(j) = \frac{n_a^j}{\sum_{h=0}^{c-1} n_a^h}$$

is the fraction of probes in $P_a$ found in bin $b_j$; and $$f_{\bar{a}}(j) = \frac{n_{\bar{a}}^j}{\sum_{h=0}^{c-1} n_{\bar{a}}^h}$$

is the fraction of probes in $\overline{P_a}$ found in bin $b_j$.

To compare the signal difference of the tail of the probability distribution, we set $r_{low}=\overline{\mu_a}$, the mean signal intensity of the probes in $\overline{P_a}$ and $r_{high}$=maximum signal intensity. We set the default number of bins, c=20.

To further stabilize and/or increase the sensitivity of the Kullback-Leibler divergence on the tail of the probability distribution, two modifications were made. First, we introduced the Anderson-Darling type weight function to the Kullback-Leibler divergence. This gave more weight to the tails than the middle of the distribution. Next, we applied the statistic over the two corresponding cumulative distribution functions instead of their probability density functions. We call our improved Kullback-Leibler divergence the Weighted Kullback-Leibler divergence (WKL score):

$$WKL(P_a | \overline{P_a}) = \sum_{j=0}^{k-1} \frac{Q_a(j)\log\left(\frac{Q_a(j)}{Q_{\bar{a}}(j)}\right)}{\sqrt{Q_{\bar{a}}(j)[1 - Q_{\bar{a}}(j)]}}$$

where $Q_a(j)$ is the cumulative distribution function of the signal intensities of the probes in $P_a$ found in bin $b_j$; $Q_{\bar{a}}(j)$ is the cumulative distribution function of the signal intensities of the probes in $\overline{P_a}$ found in bin $b_j$.

Thus for each hybridized sample, we computed the WKL score of every virus $v_a \in V$. Next, we claimed that the distribution of WKL scores of all viruses $v_a \in V$ was approximately normal if there was no virus present in a sample. We empirically verified if our claim was correct by a bootstrapping process: Let n be the number of viruses in V. For each virus $v_k \in V$ where k=1, . . . , n, we choose $|v_k|$ probe signal intensities from a real dataset D randomly with replacement to form a "perturbed" signal intensity distribution of $v_k$. Such distribution can mimic the situation where virus $v_k$ is not present in the sample D. Thereafter, n WKL scores are generated for the set of n viruses. Next, we checked if the n WKL scores follow a normal distribution by the Anderson-Darling test for normality at 95% confidence interval. The bootstrap was repeated 100,000 times. The distribution was found to be normal in more than 99% of other time. (NB: since there are 35 viral genomes represented on our microarray, n=35)

Based on the above discussion, we can test if a sample contains virus(es) by making the following null and alternative hypothesis:

$H_0$: The distribution of WKL scores is normal, i.e. viruses are not present in the sample.

$H_1$: The distribution of WKL scores is not normal, i.e. at least 1 virus is present in the sample.

Definition The Anderson-Darling test is defined as:
$H_0$: The data follow a specified distribution.
$H_a$: The data do not follow the specified distribution
Test Statistic: The Anderson-Darling test statistic is defined as $$A^2 = -N - S$$

where $$S = \sum_{i=1}^{N} \frac{(2i-1)}{N}[\ln F(Y_i) + \ln(1 - F(Y_{N+1-i}))]$$

F is the cumulative distribution function of the specified distribution. Note that the $Y_i$ are the ordered data.

Significance Level: $\alpha$

Critical Region: The critical values for the Anderson-Darling tests are dependent on the specific distribution that is being tested. Tabulated values and formulas have been published (Stephens, 1974, 1976, 1977, 1979) for a few specific distributions (normal, lognormal, exponential, Weibull, logistic, extreme value type 1). The test is a one-sided test and the hypothesis that the distribution is of a specific form is rejected if the test statistic, A, is greater than the critical value.

We proceed to apply the Anderson-Darling test for normality on the distribution of WKL scores to reject $H_0$ with 95% confidence interval. If the distribution of WKL scores is not normal, then we exclude the virus with the outlying WKL score and apply the Anderson-Darling test again. This process is repeated (to identify the presence of co-infecting pathogens) until $H_0$ is accepted.

We denote the distribution of WKL score when $H_0$ is accepted as the background WKL distribution. The viruses excluded are thus very likely to be present in the sample since their WKL score does not follow the background WKL distribution.

In our experiments, we observed that P, the probability that a non-normal distribution occurring by random chance with a given WKL score, in samples which contain a virus is very low i.e. $P<1.0\times10^{-6}$ (obtained via Z-score transformation of WKL score). Box 1 shows the pseudo-code for our virus-detection algorithm.

---

Box 1: Virus detection algorithm

Given a pathogen microarray data D with virus set V and probe set P,
Let $V_{present}$ = F
Let $D_{WKL}$ be the set of WKL($P_v$ || $P_v$) for all v ∈ V ;
1. Determine normality of $D_{WKL}$ with Anderson Darling test for normality. If $D_{WKL}$ is a normal distribution with significance level 0.05, return $V_{present}$. Else, go to step 2.
2. Find the virus $v_a$ with the highest WKL($P_a$ || $P_{a'}$) from $D_{WKL}$.
Let $V_{present} = V_{present} \cup \{V_a\}$; $D_{WKL} = D_{WKL} - \{$ WKL($P_a$ || $P_{a'}$) $\}$;
Go to step 1.
3. Remove detected SPS and verify that WKL distribution is normal.
4. If distribution is not normal, go back to step 2 to find co-infecting pathogen.

---

Predicting Genome-Wide Amplification Bias

Random primer amplification, rather than primer-specific amplification is preferred for identifying unknown pathogens in clinical specimens. However, in initial experiments using random priming amplification to identify known pathogens, we frequently observed incomplete hybridizations spanning genomic regions not explained by sequence polymorphisms (FIG. 7C) Genome secondary structure, probe secondary structure and probe GC content also failed to explain these low signal intensity probes. Thus, we hypothesized that incomplete hybridization might owe to PCR bias stemming from differential abilities of the random primers to bind to the viral genome at the reverse transcription (RT) step. The random primer used in our experiments was a 26-mer comprised of a random nonamer (3') tagged with a fixed 17-mer sequence (5'-GTTTCCCAGTCACGATA) (SEQ ID NO:1) (see also FIG. 1), where the purpose of the fixed 5' tag was to facilitate PCR of the RT product, generating PCR fragments of less than 10000 bp, in particular 500-1000 bp PCR fragments (Pang et. al. 2005; Wang et al. 2002; Wang et al. 2003). To study this phenomenon, we designed an algorithm (AES) to model the RT-PCR process using experimental data. Successful RT-PCR is dependent on the ability of primers to bind to template. Intra-primer secondary structure formation, such as dimer and hairpin formation between to template. Intra-primer secondary structure formation, such as dimer and hairpin formation between the tag and nonamer, and probe melting temperature are known to influence binding efficiency (Nguyen and Southern, 2000; Ratushna et al. 2005).

Assuming that a nonamer in the random primer mix complements the sequence of the viral genome perfectly, the algorithm determines the probability that a 500-1000 bp product can be generated from each possible starting position in the genome. Thus, for every nucleotide in a sliding window of 1000 bases, the probability that it will be successfully amplified is reflected in its Amplification Efficiency Score (AES; See Amplification Efficiency Score above). To validate the algorithm, we ranked the hybridization signal intensities for all 1,948 SPS probes for the RSV genome and compared them to their AES values. Across the RSV genome, we observed that AES correlates remarkably well to hybridization signal intensities (Fisher's Exact Probability Test P=2.2×$10^{-16}$) demonstrating the strong correlation between AES and probe detection (FIG. 12). Another comparison using 1,705 SPS probes for metapneumovirus showed a similar result, P=1.3×$10^{-9}$. The importance of AES In predicting SPS probe detection in clinical samples is demonstrated in FIG. 10. Notably, we observed that higher values of AES correlated with greater proportions of detectable probes, particularly in the top 20% of AES values. Therefore, while HD, MCM, % GC and sequence uniqueness are valuable parameters of probe performance, they do not take into account PCR bias, and thus are insufficient predictors of probe performance when considered in the absence AES. Using top 20th percentile, AES as the first filter in the selection of pathogen SPS significantly improved pathogen prediction as evidenced by higher WKL scores and elimination of false-positive calls (Table 3).

TABLE 3

Detecting pathogens using only mean probe signal intensities (T-test) results in high number of false-positive calls. Optimized hybridization signatures and removal of probes which cross-hybridize to human genome (filtered) reduces false-positive calls but is not sufficient for detection accuracy. PDA v.1 is able to make an accurate diagnosis using the entire unfiltered probe set. A virus is "detected" if WKL score >5. Using optimized hybridization signatures (filtered) increases the WKL score, corresponding to increased confidence of the diagnosis. Virus CT value: the real-time PCR cycle when virus was detected (see above).

| | | Detection using PDA v.1 | | | |
|---|---|---|---|---|---|
| Chip # | Pathogen | Max WKL score (no filters) | Max WKL score (filtered) | No. of viruses Detected | Virus CT Value | Virus copy no. |
| 32272 | Pure SARS | 5.007 | 5.803 | 1 | — | — |
| 34959 | Pure Dengue | 14.351 | 20.373 | 1 | — | — |
| 35259 | RSV patient 324 | 18.288 | 20.611 | 1 | 21.4366 | 9.8 × $10^7$ |
| 35179 | hMPV patient 122 | 1.747 | 8.439 | 1 | 25.5388 | 50384 |
| 35253 | RSV patient 841 | 12.056 | 12.069 | 1 | 20.8619 | 14 × $10^7$ |
| 36042 | RSV patient 412 | 16.466 | 17.531 | 1 | 23.5804 | 2.5 × $10^7$ |

TABLE 3-continued

Detecting pathogens using only mean probe signal intensities (T-test) results in high number of false-positive calls. Optimized hybridization signatures and removal of probes which cross-hybridize to human genome (filtered) reduces false-positive calls but is not sufficient for detection accuracy. PDA v.1 is able to make an accurate diagnosis using the entire unfiltered probe set. A virus is "detected" if WKL score >5. Using optimized hybridization signatures (filtered) increases the WKL score, corresponding to increased confidence of the diagnosis. Virus CT value: the real-time PCR cycle when virus was detected (see above).

| | | Detection using PDA v.1 | | | | |
|---|---|---|---|---|---|---|
| Chip # | Pathogen | Max WKL score (no filters) | Max WKL score (filtered) | No. of viruses Detected | Virus CT Value | Virus copy no. |
| 36053 | RSV patient 483 | 12.089 | 12.168 | 1 | 24.8340 | $1.2 \times 10^7$ |
| 35915 | non-pneumonia patient (negative control) | 3.916 | 4.284 | 0 | 0 | 0 |

Data for all patient samples hybridized on the array are shown in Table 4 below.

TABLE 4

Complete list of clinical patients hybridized onto pathogen microarrays.

| Array | Patient ID | WKL | P-value | PDA v.1 diagnosis | Clinical diagnosis* | Initial PCR diagnosis | PCR CT value | Virus copy no. | RT-PCR Primer |
|---|---|---|---|---|---|---|---|---|---|
| 35179 | 122 | 8.439216 | $1.34 \times 10^{-71}$ | hMPV | LRTI | hMPV | 24.8 | $5.0 \times 10^4$ | A1 |
| 35887 | 122 | 18.312077 | $2.98 \times 10^{-22}$ | hMPV | LRTI | hMPV | 24.8 | $5.0 \times 10^4$ | A2 |
| 71180 | 133 | 17.359597 | $2.42 \times 10^{-37}$ | hMPV | LRTI | hMPV | 25.1159 | $4.0 \times 10^4$ | A2 |
| 66691 | 165 | 8.56786 | $1.84 \times 10^{-4}$ | hMPV | pneumonia | hMPV | 27.9 | $3.9 \times 10^3$ | A2 |
| 70935 | 254 | 21.348515 | $8.70 \times 10^{-30}$ | hMPV | LRTI | hMPV | 21.9518 | $5.4 \times 10^5$ | A2 |
| 63781 | 283 | 16.680752 | $3.97 \times 10^{-12}$ | hMPV | pneumonia | unknown | | | A2 |
| 73067 | 769 | 24.006323 | $1.34 \times 10^{-51}$ | hMPV | LRTI | hMPV | 25.6715 | $2.5 \times 10^4$ | A2 |
| 66690 | 853 | | | none detected | pneumonia | hMPV | 36 | 0.5 | A2 |
| 68359 | 892 | 12.534284 | $5.66 \times 10^{-5}$ | Rhinovirus genus | pneumonia | hMPV | 33.8 | 27 | A2 |
| 35915 | 111 | | | none detected | Negative ctrl | None | | | A1 |
| 70927 | 818 | | | none detected | Negative ctrl | None | | | A2 |
| 66701 | 312 | | | none detected | pneumonia | RSV A | 33.7 | 44 | A2 |
| 71006 | 321 | | | none detected | pneumonia | RSV A | 31.1 | 340 | A2 |
| 66702 | 368 | | | none detected | pneumonia | unknown | | | A2 |
| 71025 | 414 | 25.406289 | $3.80 \times 10^{-24}$ | RSV B | pneumonia | RSV A | 22.3 | $3.9 \times 10^5$ | A2 |
| 71027 | 478 | | | none detected | pneumonia | RSV A | 34.8 | 18 | A2 |
| 73068 | 832 | 59.275233 | $1.91 \times 10^{-102}$ | RSV genus | LRTI | RSV A | 23.7681 | $1.2 \times 10^5$ | A2 |
| 71028 | 913 | 25.897084 | $3.23 \times 10^{-30}$ | RSV B | pneumonia | RSV A | 19.1 | $4.7 \times 10^6$ | A2 |
| 66703 | 924 | 12.673149 | $9.71 \times 10^{-6}$ | RSV genus | pneumonia | RSV A | 31.5 | 250 | A2 |
| 35259 | 324 | 20.61147 | $3.55 \times 10^{-94}$ | RSV B | LRTI | RSV B | 21.4366 | $3.0 \times 10^6$ | A1 |
| 35662 | 355 | 17.999418 | $2.97 \times 10^{-40}$ | RSV B | LRTI | RSV B | 20.2642 | $6.7 \times 10^6$ | A1 |
| 66695 | 374 | | | none detected | pneumonia | RSV B | 34.1 | 500 | A2 |
| 70933 | 378 | 13.81578 | $7.77 \times 10^{-17}$ | RSV B | LRTI | RSV B | 23.9204 | $5.4 \times 10^5$ | A2 |
| 36042 | 412 | 17.531234 | $4.58 \times 10^{-55}$ | RSV B | LRTI | RSV B | 23.5804 | $6.9 \times 10^5$ | A1 |
| 35890 | 412 | 17.214556 | $1.05 \times 10^{-43}$ | RSV B | LRTI | RSV B | 23.5804 | $6.9 \times 10^5$ | A2 + A3 |
| 36053 | 483 | 12.168025 | $1.47 \times 10^{-12}$ | RSV B | LRTI | RSV B | 24.834 | $2.9 \times 10^5$ | A1 |
| 70997 | 554 | 76.547183 | $1.83 \times 10^{-119}$ | Rhinovirus genus; | pneumonia | RSV B | 35.1 | 240 | A2 |
| | | 54.013223 | $2.45 \times 10^{-61}$ | Enteroviridae family | | | | | |
| 35253 | 841 | 12.069138 | $4.86 \times 10^{-26}$ | RSV B | pneumonia | RSV B | 20.8619 | $4.4 \times 10^6$ | A1 |
| 73070 | 841 | 22.10857 | $6.80 \times 10^{-50}$ | RSV B, | pneumonia | RSV B/ | 20.8619 | $4.4 \times 10^6$ | A2 |
| | | 5.708560 | $5.66 \times 10^{-6}$ | hMPV coinfection | | hMPV | 35.4 | 8 | |

TABLE 4-continued

| | | | | | | | | | | |
|---|---|---|---|---|---|---|---|---|---|---|
| 68360 | 841 | 21.369516 | $2.09 \times 10^{-25}$ | RSV B, hMPV coinfection | pneumonia | RSV B/ hMPV | 20.8619 35.4 | $4.4 \times 10^6$ 8 | A2 |
| | | 9.647188 | $1.23 \times 10^{-8}$ | | | | | | |
| 66696 | 185 | | | none detected | pneumonia | unknown | | | A2 |
| 66697 | 261 | | | none detected | pneumonia | unknown | | | A2 |
| 66698 | 331 | | | none detected | pneumonia | unknown | | | A2 |
| 71189 | 393 | | | none detected | pneumonia | unknown | | | A2 |
| 66699 | 461 | | | none detected | pneumonia | unknown | | | A2 |
| 66700 | 573 | 41.397051 | $3.97 \times 10^{-23}$ | Rhinovirus genus; | pneumonia | unknown | | | A2 |
| | | 27.444893 | $1.34 \times 10^{-11}$ | Enteroviridae family | | | | | |
| 71182 | 639 | | | none detected | pneumonia | unknown | | | A2 |
| 71007 | 699 | | | none detected | pneumonia | unknown | | | A2 |
| 71188 | 589 | | | none detected | pneumonia | unknown | | | A2 |

*LRTI: lower respiratory tract infection

The importance of AES suggested that amplification efficiency and subsequent probe detection could be improved by using optimized RT-PCR primer tags. Thus, we calculated AES scores using randomly generated 17-mer tag sequences, and selected the top 3 most divergent primers which resulted in the greatest overall increase in AES scores (FIG. 13). Using the AES optimized primers, we amplified metapneumovirus and RSV from clinical samples with improved PCR efficiency and detection sensitivity (FIG. 14, Table 5)

TABLE 5

Comparison of E-Predict and PDA v.1 algorithms on patient samples #412 and #122. Array 35179 was amplified using the original PCR primer described in Results. Arrays 36731 and 35887 were amplified using primer A2, and Array 35890 was amplified using both primers A2 and A3. PDA v.1 returned only the correct pathogen in all cases. The authors of E-Predict use P < 0.01 as significance cutoff on their platform (Urisman et al. 2005). A lower cutoff appears to be necessary if this algorithm is used to analyze our array data. The new primers designed by PCR modeling result in better prediction scores using either algorithms (arrays 35179 vs 35887). Having a second primer during the PCR process offered incremental improvement in WKL scores and P-values (arrays 36731 vs 35890).

| | | PCR amplification | E-Predict algorithm | | | GISPathogen algorithm | |
|---|---|---|---|---|---|---|---|
| Array | Patient | primers | Genome | Similarity_Score | P-value | Genome | WKL |
| 36042 | 412 (RSV) | Original primer A1 | RSV | 0.35128 | 0 | RSV | 21.526316 |
| | | | OC43 coronavirus | 0.350264 | 6.84E−20 | | |
| | | | 229E coronavirus | 0.323503 | 1.77E−10 | | |
| | | | Hepatitis B | 0.134825 | 3.03E−04 | | |
| | | | SARS coronavirus | 0.338911 | 0.00299 | | |
| | | | Hepatitis A | 0.229589 | 0.00847 | | |
| 36731 | 412 (RSV) | A2 | RSV | 0.335389 | 0 | RSV | 21.836754 |
| | | | OC43 coronavirus | 0.348043 | 2.29E−13 | | |
| | | | 229E coronavirus | 0.322055 | 2.00E−09 | | |
| | | | Hepatitis B | 0.135222 | 1.02E−06 | | |
| | | | Rubella | 0.164332 | 0.00919 | | |
| 35890 | 412 (RSV) | A2 + A3 | RSV | 0.334602 | 0 | RSV | 22.093258 |
| | | | OC43 coronavirus | 0.348969 | 3.63E−23 | | |
| | | | 229E coronavirus | 0.322805 | 3.20E−14 | | |
| | | | Hepatitis B | 0.13436 | 6.74E−04 | | |
| | | | SARS coronavirus | 0.338609 | 0.03060 | | |
| 35179 | 122 (hMPV) | Original primer A1 | hMPV | 0.260110695 | 5.01E−28 | hMPV | 9.763149 |
| | | | Rubella | 0.164784981 | 1.20E−17 | | |
| | | | Foot-and-mouth C | 0.206747816 | 4.66E−11 | | |
| | | | Jap encephalitis | 0.201347222 | 1.65E−04 | | |
| | | | Hepatitis B | 0.133407622 | 1.98E−04 | | |
| | | | Yellow Fever | 0.200500564 | 0.00567 | | |
| | | | Echovirus 1 | 0.222002025 | 0.01740 | | |
| | | | Newcastle | 0.234481686 | 0.01820 | | |

TABLE 5-continued

Comparison of E-Predict and PDA v.1 algorithms on patient samples
412 and #122. Array 35179 was amplified using the original PCR primer
described in Results. Arrays 36731 and 35887 were amplified using primer A2,
and Array 35890 was amplified using both primers A2 and A3. PDA v.1 returned
only the correct pathogen in all cases. The authors of E-Predict use P < 0.01 as
significance cutoff on their platform (Urisman et al. 2005). A lower cutoff
appears to be necessary if this algorithm is used to analyze our array data. The
new primers designed by PCR modeling result in better prediction scores using
either algorithms (arrays 35179 vs 35887). Having a second primer during the
PCR process offered incremental improvement in WKL scores and P-values
(arrays 36731 vs 35890).

| Array | Patient | PCR amplification primers | E-Predict algorithm | | | GISPathogen algorithm | |
|---|---|---|---|---|---|---|---|
| | | | Genome | Similarity_Score | P-value | Genome | WKL |
| 35887 | 122 (hMPV) | A2 | hMPV | 0.299655 | 0 | hMPV | 39.677149 |
| | | | Rubella | 0.169626 | 3.40E−19 | | |
| | | | Hepatitis B | 0.137703 | 5.84E−12 | | |
| | | | OC43 coronavirus | 0.347685 | 5.06E−10 | | |
| | | | 229E coronavirus | 0.321702 | 1.72E−06 | | |
| | | | SARS coronavirus | 0.340504 | 1.76E−06 | | |
| | | | Foot-and-mouth C | 0.2075 | 1.31E−04 | | |
| | | | Newcastle | 0.23453 | 0.04310 | | |

PDA v.1—an Algorithm for Detecting Pathogens

Clinical specimens are often sub-optimal for genomic amplification: they may have low viral titres, have sequence polymorphisms from the reference strain on the array, or have co-infecting pathogens. Microarrays also have an inherent noise from non-specific hybridization and other artifacts. Thus, interpreting microarray data is not a simple matter of matching probe signal intensity profiles to the SPS, or using simple statistical methods (e.g. T-test, ANOVA, and the like). To address this issue, we established a robust statistical software, PDA v.1, which analyzes the distribution of probe signal intensities relative to the in silico predicted SPS to identify pathogens present in a hybridized sample (See above).

Figure 9A:
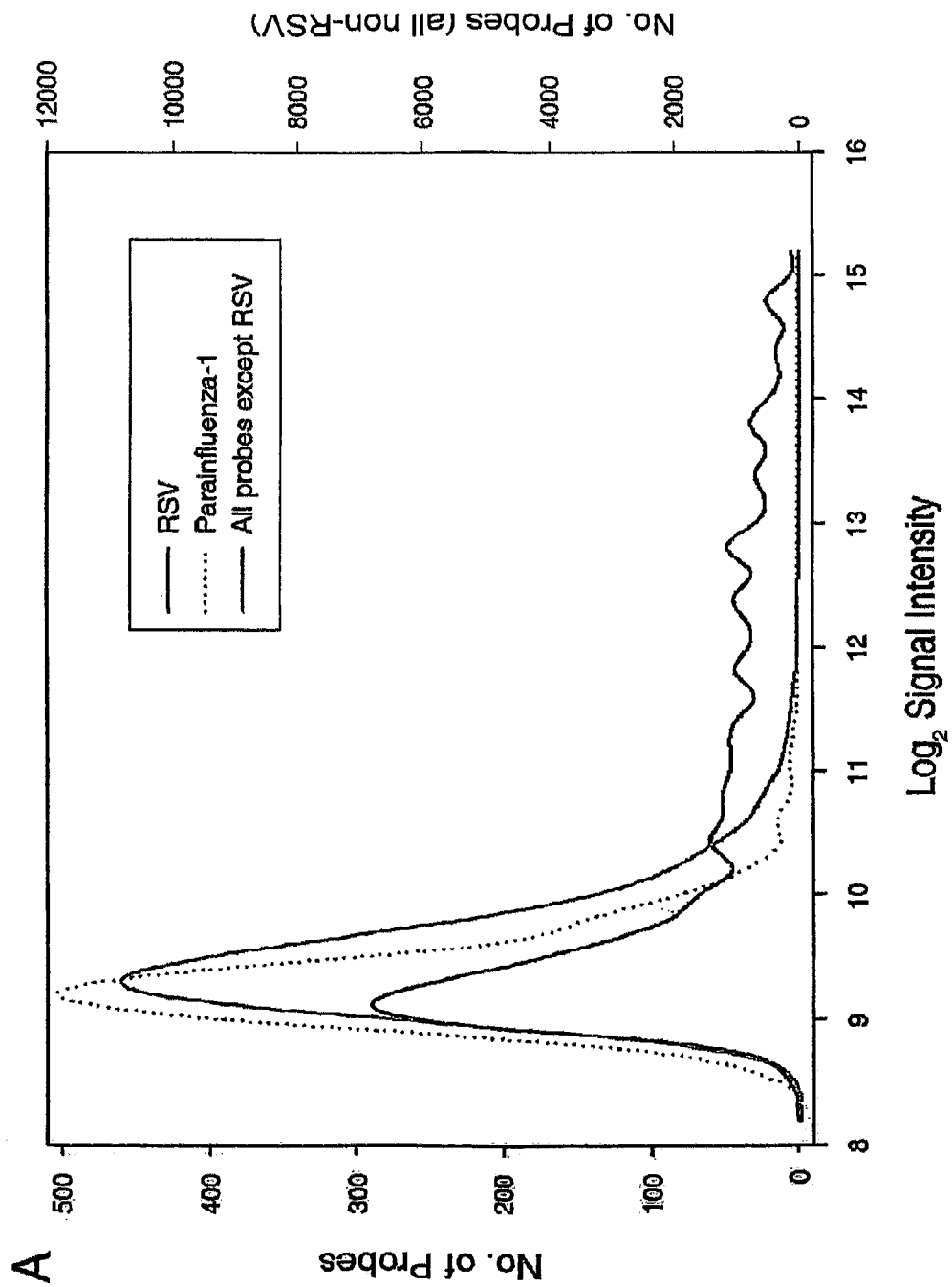

Based on our observations that while the signal intensities for all probes on the array would fall in a normal distribution, a large proportion of probes comprising a pathogen SPS which is present in the sample would have very strong signal intensities resulting in a distribution skewed to the right; we deduced that we could detect the presence of pathogens by analyzing the distribution of probe signal intensities (FIG. 9A). Examining the tails of the signal intensity distributions for each SPS would also enable us to identify the presence of co-infecting pathogens in the sample.

Thus, PDA v.1 comprises 2 parts (1) Weighted Kullback-Leibler Divergence (WKL; our enhanced Kullback-Leibler test) to evaluate the probe signal intensity of probes in each pathogen SPS, and (2) an Anderson-Darling test to determine if the distribution of WKL scores for each SPS is normal.

Figure 9B:
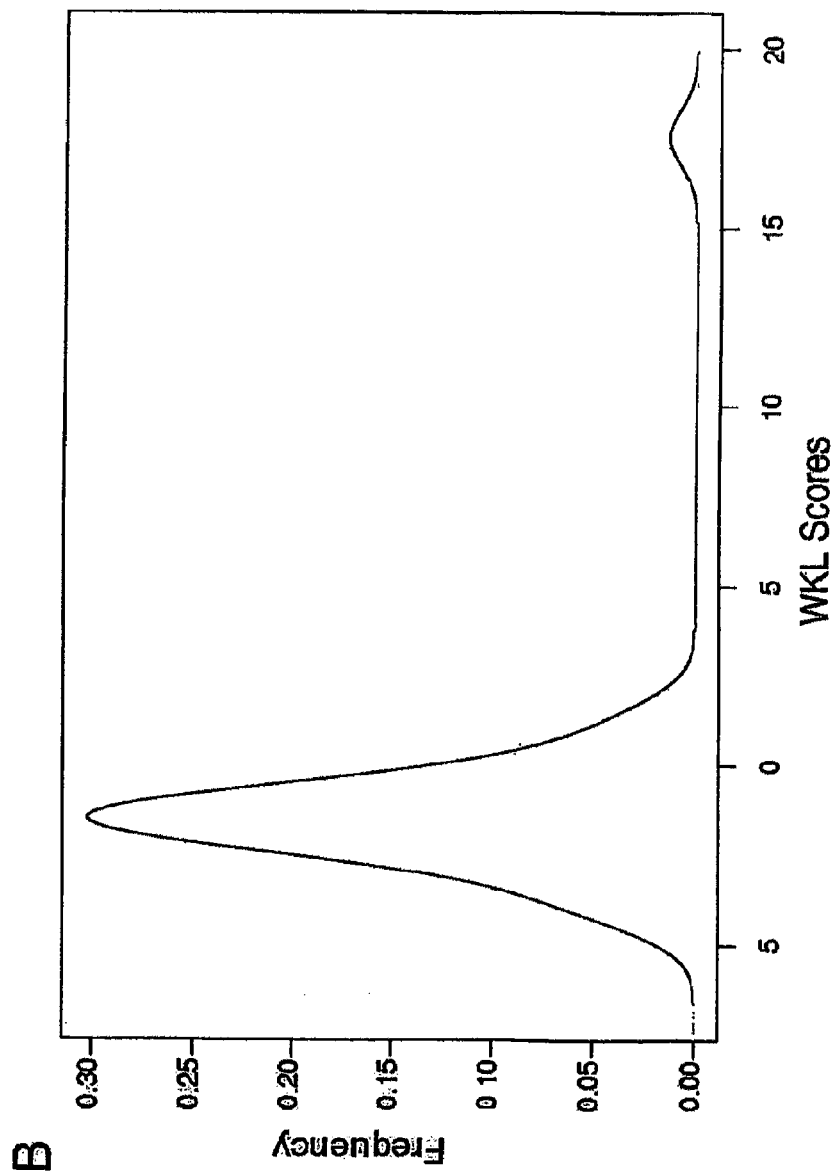

The original Kullback-Leibler cannot reliably determine differences in the tails of a probability distribution, and is highly dependent on the number of probes/genome and the size of each signal intensity bin (Kullback and Leibler, 1951). We overcame these deficits by incorporating the Anderson-Darling statistic to give more weight to the tails of each distribution, and by using a cumulative distribution function Instead of the original probability distribution (Anderson and Darling, 1952). We call our enhanced KL divergence the Weighted Kullback-Leibler divergence (WKL):

$$WKL(P_a | \overline{P_a}) = \sum_{j=0}^{k-1} \frac{Q_a(j)\log\left(\frac{Q_a(j)}{Q_{\overline{a}}(j)}\right)}{\sqrt{Q_a(j)[1-Q_a(j)]}}$$

where $Q_a(j)$ is the cumulative distribution function of the signal intensities of the probes in $P_a$ found in bin $b_j$; $Q_{\overline{a}}(j)$ is the cumulative distribution function of the signal intensities of the probes in $\overline{P_a}$ found in bin $b_j$. SPS representing absent pathogens should have normal signal intensity distributions and thus relatively low WKL scores, whereas those representing present pathogens should have high, statistically significant outlying WKL scores (FIG. 9B). In the second part of PDA v.1, the distribution of WKL scores is subjected to an Anderson-Darling test for normality. If P<0.05, the WKL distribution is considered not normal, implying that the pathogens with outlying, WKL score is present. Upon identification of a pathogen, a separate Anderson-Darling test is performed in the absence of its WKL score to test for the presence of co-infecting pathogens. In this manner, the procedure is iteratively applied until only normal distributions remain (i.e., P>0.05; see Table 3 and Table 4 above). PDA v.1 is extremely fast, capable of making a diagnosis from a hybridized microarray in about 10 secs.

Pathogen Diagnosis on 33 Clinical Patient Samples

We evaluated our platform by hybridizing 33 clinical specimens onto our pathogen microarray platform, according to the workflow illustrated in FIG. 11. Of these, 27 specimens had been previously diagnosed as RSV A, RSV B or metapneumovirus. Our platform accurately detected pathogens from 21/27 samples. The 6 samples where no virus was detected (false-negative) were at the detection limit by real-time PCR (<10 viral copies/reaction), and such low viral loads were unlikely to be the etiologic agent responsible for the patient's severe disease. 2 of these were correctly diagnosed by microarray to be infected with rhinovirus. In a screen of another 6 patients with severe respiratory disease caused by unknown pathogen, the microarray identified the etiologic agent (rhinovirus) in 1 of the samples (Table 4 above). These results were validated by real-time PCR. As expected, we did not detect any pathogens when we hybridized samples extracted from pneumonia patients with non-viral etiology.

Data Analysis

Microarrays were scanned at 5 μm resolution using the Axon 4000b scanner and Genepix 4 software (Axon Instruments). Signal intensities were extracted using Nimblescan 2.1 software (NimbleGen Systems). Using an automated script, we calculated the median signal intensity (to eliminate hybridization artifacts) and standard deviation from the 7 replicates of each probe. The probe signal intensities were sorted by genome and arranged in sequence order, then reformatted into CDT format for graphical viewing of signal intensities in Java Treeview (http://treeview.sourceforge.net). In parallel, the probe median signal intensities were analysed using PDA v.1 to determine which pathogen is present, and associated confidence level of prediction. The present inventors carried out experiments to demonstrate the effects of probe design on experimental results and then to show the robustness of the analysis algorithm according to the present invention.

Effects of Probe Design on Experimental Results

A PDC containing 53555 40-mer probes from 35 viruses affecting human was used for 4 independent microarray experiments. These 53555 probes were chosen based on a 5-bps tiling of each virus and were not subjected to any of our probe design criteria. Thus, we would expect errors arising due to CG-content, cross-hybridization and inefficient amplification to be significantly more than that of a PDC with well-designed probes. We tested our analysis algorithm in such an adverse setting for 4 experiments.

In this example, a human sample with an unknown pathogen was amplified by the RT-PCR process using random probes and then hybridized onto the PDC. We subjected the probes for each of the 35 viruses on our PDC to the one-tailed t-test with significance level 0.05 and computed the Weighted Kullback-Leibler (WKL) divergence of their signal intensities to the signal intensities of all the probes on the chip to determine which virus was in the sample for each experiment. Confirmation of the accuracy of the analysis by our program was done by wet-lab PCR to identify the actual virus in the sample. We present the results of our analysis for the 4 experiments of Table 6 and their corresponding PCR verifications in Table 6.

TABLE 6

Analysis results done on a PDC with no probe design criteria applied.
The virus determined by our analysis algorithm to be the actual virus in the sample tested for each experiment is highlighted in light gray colour.

| | Experiment 1 | | Experiment 2 | | Experiment 3 | | Experiment 4 | |
|---|---|---|---|---|---|---|---|---|
| Sample Name [D] | 35259_324 | | 35179_122 | | 35253_841 | | 35915_111 | |
| | 53555 | | 53555 | | 53555 | | 53555 | |
| Viruses (Accession No.) | t-test p-value | WKL | t-test p-value | WKL | t-test p-value | WKL | t-test p-value | WKL |
| NC_001781.1 | 0 | 16.391 | 1 | NA | 0 | 10.85635 | 1 | NA |
| NC_003461.1 | 1 | NA | 1 | NA | 1 | NA | 1 | NA |
| NC_003443.1 | 0.999324 | NA | 0.873017 | NA | 0.99802 | NA | 0.999961 | NA |
| NC_001796.2 | 1 | NA | 1 | NA | 1 | NA | 1 | NA |
| AY283794.1 | 0 | 0.5435 | 0.108141 | NA | 0 | 0.775959 | 0 | 0.435427 |
| NC_005147.1 | 0 | 1.2896 | 1 | NA | 0 | 1.399591 | 0 | 1.762912 |
| NC_002645.1 | 0 | 1.2943 | 0.999847 | NA | 0 | 1.655888 | 0 | 2.079334 |
| NC_004148.2 | 1 | NA | 0.002733 | 5.762907 | 1 | NA | 1 | NA |
| NC_002023.1 NC_002022.1 NC_002021.1 NC_002020.1 NC_002019.1 NC_002018.1 NC_002017.1 | 1 | NA | 0.579561 | NA | 1 | NA | 1 | NA |
| NC_002204.1 NC_002205.1 NC_002206.1 NC_002207.1 NC_002208.1 NC_002209.1 NC_002210.1 NC_002211.1 | 1 | NA | 1 | NA | 1 | NA | 1 | NA |
| NC_001563.2 | 1 | NA | 0.000001 | 0.537826 | 1 | NA | 0.995013 | NA |
| NC_002031.1 | 1 | NA | 0.000005 | 0.758758 | 0.998873 | NA | 0.363947 | NA |
| NC_002728.1 | 1 | NA | 0.999062 | NA | 1 | NA | 1 | NA |
| NC_002617.1 | 0.999994 | NA | 0 | 0.571844 | 1 | NA | 0.769098 | NA |
| NC_001802.1 | 1 | NA | 0.999966 | NA | 1 | NA | 1 | NA |
| NC_003977.1 | 0 | 2.7424 | 0 | 2.189827 | 0 | 3.978747 | 0 | 1.490665 |
| NC_001576.1 | 0.371224 | NA | 0.004643 | 0.94841 | 0.009599 | 1.257041 | 0 | 3.961532 |
| NC_002554.1 | 0.000062 | 0.7146 | 0 | 1.527292 | 0.299334 | NA | 0.000002 | 0.166239 |
| NC_001545.1 | 0 | 1.4545 | 0 | 2.438558 | 0 | 0.869782 | 0 | 0.989592 |
| NC_001489.1 | 0 | 1.7088 | 0.319125 | NA | 0 | 2.593065 | 0 | 1.510399 |

TABLE 6-continued

| | | | | | | | | |
|---|---|---|---|---|---|---|---|---|
| NC_005222.1 | 0.999757 | NA | 0.646314 | NA | 0.773912 | NA | 0.807875 | NA |
| NC_005217.1 | 0.60477 | NA | 0.999903 | NA | 0.354358 | NA | 0.000871 | 0.626818 |
| NC_004294.1 | 0 | 1.8411 | 0.000523 | 0.902399 | 0 | 2.43215 | 0.000007 | 0.537531 |
| NC_004291.1 | 0.662386 | NA | 0.954137 | NA | 0.255422 | NA | 0.099148 | NA |
| NC_001437.1 | 1 | NA | 0 | 0.593093 | 1 | NA | 1 | NA |
| AB189128.1 | 1 | NA | 0.906213 | NA | 1 | NA | 1 | NA |
| AF326573.1 | 1 | NA | 0.038503 | 0.539783 | 1 | NA | 1 | NA |
| AF489932.1 | 1 | NA | 0.899797 | NA | 1 | NA | 1 | NA |
| M87512.1 | 1 | NA | 0.759668 | NA | 1 | NA | 1 | NA |
| NC_001430.1 | 1 | NA | 0.912496 | NA | 1 | NA | 0.999912 | NA |
| NC_001428.1 | 0.999988 | NA | 0.284792 | NA | 0.999346 | NA | 0.957164 | NA |
| NC_001612.1 | 0.970379 | NA | 0.000001 | 0.557865 | 0.998878 | NA | 0.061226 | NA |
| NC_003986.1 | 1 | NA | 0.000012 | 0.604474 | 1 | NA | 0.997945 | NA |
| NC_001472.1 | 0.999999 | NA | 0.0046 | 0.455194 | 0.999579 | NA | 0.143404 | NA |
| NC_001617.1 | 0.721465 | NA | 0.98373 | NA | 0.175733 | NA | 0.414209 | NA |
| NC_001490.1 | 0.999808 | NA | 0.995029 | NA | 0.997369 | NA | 0.859025 | NA |
| Deduction Virus | NC_001781.1 (RSV) | | NC_004148.2 (HMPV) | | NC_001781.1 (RSV) | | None | |
| Confirmation Virus (PCR) | NC_001781.1 (RSV) | | NC_004148.2 (HMPV) | | NC_001781.1 (RSV) | | None | |

The present results show that the analysis algorithm accurately deduces the actual virus in the sample tested in the first 3 experiments (results shown in Table 6 above). Furthermore, we were able to deduce that the sample has no viruses in the last experiment. Note that if we had just used the t-test with level of significance 0.05, then the number of viruses detected to be present for each sample is shown in Table 7 below.

TABLE 7

| | False positive detection of viruses using t-test alone | | | |
|---|---|---|---|---|
| | Sample Name | | | |
| | 35259_324 | 35179_122 | 35253_841 | 35915_111 |
| Viruses Detected Using T-test | 9 | 14 | 9 | 10 |
| False Positives | 8 | 13 | 8 | 10 |
| Max KL divergence (>5.0) | 16.391 | 5.76 | 10.85 | — |
| Viruses Detected Using T-test followed by KL divergence | 1 | 1 | 1 | 0 |

By using the Weighted Kullback-Leibler divergence of the viruses that pass the t-test, we were able to remove all false positive viruses and identify the actual virus. Thus, our analysis algorithm can robustly determine the virus under a high level noise.

Next, we investigated the effects of using a PDC with probe design criteria applied on our analysis results. Firstly, the amplification efficiency map for each of the 35 viruses was computed. Then, the exact 53555 probes on the original PDC were subjected to probe design criteria. Probes which had extreme levels of CG-content, high similarity to human and non-target viruses, and low amplification efficiency scores were removed from the chip. A total of 10955 probes were retained for the second set of experiments. Using the samples used in the first set of experiments, we repeated the 4 experiments in Table 8 below with the new chip. The experimental results are presented in Table 8.

TABLE 8

Analysis results done on a PDC with probe design criteria applied. The virus determined by our analysis algorithm to be the actual virus in the sample tested for each experiment is highlighted in light gray colour.

| | Experiment 1 | | Experiment 2 | | Experiment 3 | | Experiment 4 | |
|---|---|---|---|---|---|---|---|---|
| Sample Name [D] | 35259_324 | | 35179_122 | | 35253_841 | | 35915_111 | |
| | 10955 | | 10955 | | 10955 | | 10955 | |
| Viruses (Accession No.) | t-test p-value | WKL | t-test p-value | WKL | t-test p-value | WKL | t-test p-value | WKL |
| NC_001781.1 | 0 | 18.54859 | 1 | NA | 0 | 11.17914 | 1 | NA |
| NC_003461.1 | 1 | NA | 1 | NA | 1 | NA | 1 | NA |
| NC_003443.1 | 0.548718 | NA | 0.53727 | NA | 0.002783 | 0.837121 | 0.020436 | 0.603552 |
| NC_001796.2 | 1 | NA | 0.999907 | NA | 1 | NA | 1 | NA |
| AY283794.1 | 0 | 1.347801 | 0.024116 | 0.858364 | 0 | 1.523272 | 0 | 1.128637 |
| NC_005147.1 | 0 | 1.604381 | 0.999697 | NA | 0 | 2.150019 | 0 | 2.893555 |
| NC_002645.1 | 0 | 2.802742 | 0.999895 | NA | 0 | 4.612482 | 0 | 3.635771 |
| NC_004148.2 | 1 | NA | 0.000003 | 9.324785 | 1 | NA | 1 | NA |

TABLE 8-continued

| | | | | | | | | |
|---|---|---|---|---|---|---|---|---|
| NC_002023.1 | 1 | NA | 0.124517 | NA | 1 | NA | 0.999163 | NA |
| NC_002022.1 | | | | | | | | |
| NC_002021.1 | | | | | | | | |
| NC_002020.1 | | | | | | | | |
| NC_002019.1 | | | | | | | | |
| NC_002018.1 | | | | | | | | |
| NC_002017.1 | | | | | | | | |
| NC_002204.1 | 1 | NA | 0.998724 | NA | 1 | NA | 1 | NA |
| NC_002205.1 | | | | | | | | |
| NC_002206.1 | | | | | | | | |
| NC_002207.1 | | | | | | | | |
| NC_002208.1 | | | | | | | | |
| NC_002209.1 | | | | | | | | |
| NC_002210.1 | | | | | | | | |
| NC_002211.1 | | | | | | | | |
| NC_001563.2 | 0.986443 | NA | 0.428418 | NA | 0.76002 | NA | 0.112011 | NA |
| NC_002031.1 | 0.998103 | NA | 0.003435 | 2.52162 | 0.278672 | NA | 0.409527 | NA |
| NC_002728.1 | 0.999375 | NA | 0.30951 | NA | 0.969492 | NA | 0.297244 | NA |
| NC_002617.1 | 0.63418 | NA | 0.003578 | 0.965856 | 0.247148 | NA | 0.025188 | 0.861163 |
| NC_001802.1 | 1 | NA | 0.998118 | NA | 1 | NA | 1 | NA |
| NC_003977.1 | 0 | 3.062956 | 0.000028 | 3.027442 | 0 | 4.574591 | 0 | 3.277708 |
| NC_001576.1 | 0.579342 | NA | 0.101093 | NA | 0.155219 | NA | 0.026417 | 3.280335 |
| NC_002554.1 | 0.6722 | NA | 0 | 2.289379 | 0.80654 | NA | 0.106683 | NA |
| NC_001545.1 | 0 | 2.225817 | 0 | 2.794877 | 0.000019 | 1.674329 | 0 | 1.97064 |
| NC_001489.1 | 0.099427 | NA | 0.999985 | NA | 0.000366 | 1.829543 | 0.000006 | 3.023235 |
| NC_005222.1 | 0.999735 | NA | 0.294141 | NA | 0.974031 | NA | 0.356952 | NA |
| NC_005217.1 | 0.916186 | NA | 0.994358 | NA | 0.600759 | NA | 0.032616 | 2.105628 |
| NC_004294.1 | 0.867625 | NA | 0.235197 | NA | 0.100961 | NA | 0.052759 | NA |
| NC_004291.1 | 0.992032 | NA | 0.964128 | NA | 0.714211 | NA | 0.206422 | NA |
| NC_001437.1 | 1 | NA | 0.001058 | 1.563913 | 1 | NA | 0.857228 | NA |
| AB189128.1 | 1 | NA | 0.732737 | NA | 0.999997 | NA | 0.98859 | NA |
| AF326573.1 | 1 | NA | 0.435629 | NA | 0.999986 | NA | 0.905393 | NA |
| AF489932.1 | 1 | NA | 0.322655 | NA | 0.999996 | NA | 0.996837 | NA |
| M87512.1 | 0.999617 | NA | 0.057346 | NA | 0.999758 | NA | 0.937937 | NA |
| NC_001430.1 | 1 | NA | 0.865038 | NA | 1 | NA | 0.882339 | NA |
| NC_001428.1 | 1 | NA | 0.522986 | NA | 0.999351 | NA | 0.749412 | NA |
| NC_001612.1 | 0.991708 | NA | 0.751091 | NA | 0.990929 | NA | 0.257635 | NA |
| NC_003986.1 | 0.999997 | NA | 0.02014 | 0.93616 | 0.937996 | NA | 0.708985 | NA |
| NC_001472.1 | 0.99959 | NA | 0.977242 | NA | 0.957869 | NA | 0.692936 | NA |
| NC_001617.1 | 0.435562 | NA | 0.474076 | NA | 0.028549 | 1.699567 | 0.079676 | NA |
| NC_001490.1 | 1 | NA | 0.90881 | NA | 0.996231 | NA | 0.518662 | NA |
| Deduction Virus | NC_001781.1 (RSV) | | NC_004148.2 (HMPV) | | NC_001781.1 (RSV) | | None | |
| Confirmation Virus (PCR) | NC_001781.1 (RSV) | | NC_004148.2 (HMPV) | | NC_001781.1 (RSV) | | None | |

In the following set of experiments, the analysis algorithm correctly detected the actual virus in the 3 samples and also the negative sample. After designing good probes for our chip, the Weighted Kullback-Leibler divergence of the actual viruses in Experiment 1, 2 and 3 was greater than that of the corresponding experiments without probe design. This means that the signal intensities from the actual virus were relatively higher than the background noise in the PDC. This showed that our probe design criteria had removed some bad probes from the PDC, which resulted in a more accurate analysis.

Again, we present results of the 4 experiments shown in Table 9 below, if we had just used the t-test with a level of significance 0.05. This time, the number of viruses detected to be present for each sample is shown in Table 9:

TABLE 9

False positive detection of viruses using t-test alone in a PDC with probe design.

| | Sample Name | | | |
|---|---|---|---|---|
| | 35259_324 | 35179_122 | 35253_841 | 35915_111 |
| Viruses Detected Using T-test | 6 | 9 | 9 | 10 |

TABLE 9-continued

False positive detection of viruses using t-test alone in a PDC with probe design.

| | Sample Name | | | |
|---|---|---|---|---|
| | 35259_324 | 35179_122 | 35253_841 | 35915_111 |
| False Positives | 5 | 8 | 8 | 10 |
| Max KL divergence (>5.0) | 18.54859 | 9.324785 | 11.17914 | — |
| Viruses Detected Using T-test followed by KL divergence | 1 | 1 | 1 | 0 |

From Table 9, it can be seen that probe design has reduced the number of false positive viruses detected by the t-test for samples 35259_324 and 35179_122. A more important observation is that the Weighted Kullback-Leiber divergence for the actual virus has increased for all 4 samples. This means that the signals of the actual virus are more differentiated than the background signals when probe design criteria are applied on the PDC.

In conclusion, we showed that using the one-tailed t-test with significance level 0.05, followed by computing the Weighted Kullback-Leibler divergence for the signal intensities of each virus, we were able to accurately analyze the data on the PDC and determine with high probability the actual pathogen in the sample. Although the analysis algorithm works well even under a high level of noise, we showed that the accuracy of the analysis is improved by using the above-described probe design criteria to select a good set of probes for the PDC.

Alternative Methods for Probe Design and Pathogen Detection

Very few algorithms are available for predicting cross hybridization on microarrays and only 1 algorithm, E-predict, has been reported and validated for detecting pathogens on microarrays (Urisman et al. 2005; Li et al. 2005). E-predict matches hybridization signatures with predicted signatures derived from the theoretical free energy of hybridization for each microarray probe. However, using E-predict to analyze our microarrays resulted in a number of false positive calls (see Table 5 above). For example, E-Predict detected coronavirus in RSV patient 412 (FIG. 15). Diagnostic PCR using pancoronavirus primers as well as specific diagnostic primers for OC43 and 229E coronavirus confirmed the absence of coronavirus from patient 412 (see Table 4 above). We hypothesized that false positive calls using E-Predict resulted from coronavirus probes which cross-hybridized with human or RSV genomes. Indeed, 85% of the 50 coronavirus probes with highest signal intensity were predicted to cross-hybridize with human genome and 65% had HD<17 relative to RSV, which is just above our HD threshold of 12 for familial cross-hybridization. Furthermore, E-Predict was optimized to work on a microarray which contained probes that are highly conserved among viral genomes regions instead of tiling arrays where cross-hybridization to human genome would be a key consideration. Thus it is likely that these 2 factors—different microarray design strategy and cross-hybridization to human genome, contributed to the poor performance of E-predict on our platform. From our experience with E-predict, it would not be fair for us to compare PDA v1 with the other algorithms as they were designed for different probe lengths and optimized for other applications and platforms.

Conclusion

By empirically determining cross-hybridization thresholds, we created in silico pathogen signature probe sets comprising only probes which would hybridize well to specific viruses present in clinical samples. The AES algorithm allowed us to design universal primer tags to efficiently amplify entire viral genomes. Together with PDA v.1 detection algorithm, we can confidently identify any of the pathogens represented on the microarray from clinical samples. This approach eliminates the requirement for empirical validation of each pathogen hybridization signature and allows for future microarrays containing probes for >10000 pathogens to become powerful diagnostic platforms for pathogen identification.

We have optimized the design and analysis for pathogen detection microarrays, facilitating their use in a hospital setting. We discovered that primer tags routinely used in random PCR are biased, resulting in non-uniform amplification of pathogen genomes. This bias can be avoided by designing primers using our AES algorithm. Our in silico signature probe sets allow us to predict accurately which probes would hybridize to any pathogen represented on the array. Together with the PDA v.1 detection algorithm, this approach eliminates the requirement for empirical validation of each pathogen hybridization signature and allows for future microarrays containing probes for >10000 pathogens to become powerful diagnostic platforms for pathogen identification.

Here, we report the results of a systematic investigation of the complex relationships between viral amplification efficiency, hybridization signal output, target-probe annealing specificity, and reproducibility of pathogen detection using a custom designed microarray platform. Our findings form the basis of a novel methodology for the in silico prediction of optimal pathogen signature probe sets (SPS), shed light on the factors governing viral amplification efficiency (prior to microarray hybridization) and demonstrate the important connection between a viral amplification efficiency score (AES) and optimal probe selection. Finally, we describe a new statistics-based pathogen detection algorithm (PDA), that can rapidly and reproducibly identify pathogens in clinical specimens across a range of viral titers.

We have demonstrated the feasibility of using viral genome sequences obtained from publicly available databases, to detect viruses in clinical samples with a high degree of certainty if at least 4000 virus copies are present (see Table 3 above). Its sensitivity approaches that of antigen detection methods, making it a clinically relevant detection tool (Liu et al. 2005; Marra et al. 2003). The ability to predict in silico pathogen hybridization. signatures accurately presents a significant advance over current microarray methods, which require empirical validation by first hybridizing the array with pure pathogen samples. Besides specific identification of pathogens represented on the array, PDA v.1 allows identification of the pathogen class, family or genus for those genomes which are not specifically represented on the array (by relaxing thresholds for HD and MCM). This information is often sufficient for treatment decisions in the clinic. With an AES-optimized tag, we were able to identify virus from clinical samples which could not be detected earlier when amplified using a non-AES-optimized tag. Thus selection of tags by AES increased PCR efficiency and sensitivity of detection. The algorithm according to the invention may be applied to other tagged-based PCR applications, such as generation of DNA libraries and enrichment of RNA for resequencing.

REFERENCES

Altschul S F, Madden T L, Schaffer A A, Zhang J, Zhang Z, et al. (1997) Gapped BLAST and PSI-BLAST: a new generation of protein database search programs. Nucleic Acids Res 25: 3389-3402.

Anderson T W, Darling D A (1952) Asymptotic theory of certain goodness of fit criteria based on stochastic processes. Annals of Mathematical Statistic 23: 192-212.

Bodrossy L, Sessitsch A (2004) Oligonucleotide microarrays in microbial diagnostics. Curr Opin Microbiol 7: 245-254.

Bohlander S K, Espinosa I, Rafael, Le Beau M M, Rowley J D, Diaz M O (1992) A method for the rapid sequence-independent amplification of microdissected chromosomal material. Genomics 13: 1322-1324.

Bustin, S. A. & Nolan, T. (2004) Pitfalls of quantitative real-time reverse-transcription polymerase chain reaction. J Biomol Tech 15, 155-166

Deffernez C, Wunderli W, Thomas Y, Yerly S, Perrin L, et al. (2004) Amplicon Sequencing and Improved Detection of Human Rhinovirus in Respiratory Samples 10.1128/JCM.42.7.3212-3218.2004. J Clin Microbiol 42: 3212-3218.

Fu J, Tan B H, Yap E H, Chan Y C, Tan Y H (1992) Full-length cDNA sequence of dengue type 1 virus (Singapore strain S275/90). Virology 188: 953-958.

Goulden, C. H. Methods of Statistical Analysis, Edn. 2nd. (John Wiley & Sons, Inc., New York; 1956).

Hamming R W (1950) Error Detecting and Error Correcting Codes. Bell System Technical Journal 29:147-160.

International Human Genome Sequencing Consortium. Initial sequencing and analysis of the human genome. Nature 409(6822), 860-921 (2001).

Kane M D, Jatkoe T A, Stumpf C R, Lu J, Thomas J D, et al. (2000) Assessment of the sensitivity and specificity of oligonucleotide (50mer) microarrays. Nucleic Acids Res 28: 4552-4557.

Kane, M. D. et al. Assessment of the sensitivity and specificity of oligonucleotide (50mer). microarrays. Nucleic Acids Res 28, 4552-4557 (2000).

Ksiazek T G, Erdman D. Goldsmith C S, Zaki S R, Peret T. et al. (2003) A novel coronavirus associated with severe acute respiratory syndrome. N Engl J Med 348: 1953-1966.

Kullback S, Leibler R A (1951) On information and sufficiency. Annals of Mathematical Statistic 22: 79-86.

Li X, He Z, Zhou J (2005) Selection of optimal oligonucleotide probes for microarrays using multiple criteria, global alignment and parameter estimation. Nucl Acids Res 33: 6114-6123.

Liu J, Lim S L, Ruan Y. Ling A E, Ng L F, et al. (2005) SARS transmission pattern in Singapore reassessed by viral sequence variation analysis. PLoS Med 2(2), 162-168.

Marra M A, Jones S J, Astell C R, Holt R A, Brooks-Wilson A, et al. (2003) The Genome sequence of the SARS-associated coronavirus. Science 300:1399-1404.

Maskos U, Southern E M (1993) A study of oligonucleotide reassociation using large arrays of oligonucleotides synthesised on a glass support. Nucleic Acids Res 21: 4663-4669.

Moës E, Vijgen L, Keyaerts E, Zlateva K, Li S, et al. (2005) A novel pancoronavirus RT-PCR assay: frequent detection of human coronavirus NL63 in children hospitalized with respiratory tract infections in Belgium. BMC Infect Dis 5: 6.

Nguyen H K, Southern E M (2000) Minimising the secondary structure of DNA targets by incorporation of a modified deoxynucleoside: implications for nucleic acid analysis by hybridisation. Nucleic Acids Res 28: 3904-3909.

Nuwaysir E F, Huang W, Albert T J, Singh J, Nuwaysir K, et al. (2002) Gene expression analysis using oligonucleotide arrays produced by maskless photolithography. Genome Res 12: 1749-1755.

Pang X L, Preiksaitis J K, Lee B (2005) Multiplex real time RT-PCR for the detection and quantitation of norovirus genogroups I and II In patients with acute gastroenteritis. J Clin Virol 33: 168-171.

Ratushna V G, Weller J W, Gibas C J (2005) Secondary structure in the target as a confounding factor in synthetic oligomer microarray design. BMC Genomics 6: 31.

Ruan Y J, Wei C L, Ee A L, Vega V B, Thoreau H, et al. (2003) Comparative full-length genome sequence analysis of 14 SARS coronavirus isolates and common mutations associated with putative origins of infection. Lancet 361: 1779-1785.

Sambrook and Russel, (2001) Molecular Cloning: A Laboratory Manual, Cold Springs Harbor Laboratory, New York SantaLucia, J., Jr., Allawi, H. T. & Seneviratne, P. A. (1199*6*/B) Improved nearest-neighbor parameters for predicting DNA duplex stability. Biochemistry 35, 3555-3562

Smalling T W, Sefers S E, Li H, Tang Y W (2002) Molecular approaches to detecting herpes simplex virus and enteroviruses in the central nervous system. J Clin Microbiol 40:2317-2322.

Stephens, M. A. (1974). EDF Statistics for Goodness of Fit and Some Comparisons, Journal of the American Statistical Association, Vol. 69, pp. 730-737.

Striebel H M, Birch-Hirschfeld E, Egerer R, Foldes-Papp Z (2003) Virus diagnostics on microarrays. Curr Pharm Biotechnol 4: 401-415.

Sung, W. K. & Lee, W. H. Fast and Accurate Probe Selection Algorithm for Large Genomes. CSB (2003).

Sung, W. K. & Lee, W. H. (2003) in IEEE Computational Systems Bioinformatics Conference Stanford University, Stanford, Calif.

Urisman A, Fischer K F, Chiu C Y, Kistler A L, Beck S, et al. (2005) E-Predict: a computational strategy for species identification based on observed DNA microarray hybridization patterns. Genome Biol 6: R78.

Vega V B, Ruan Y, Liu J, Lee W H, Wei C L, et al. (2004) Mutational dynamics of the SARS coronavirus in cell culture and human populations isolated in 2003. BMC Infect Dis 4: 32.

Vora G J, Meador C E, Stenger D A, Andreadis J D (2004) Nucleic acid amplification strategies for DNA microarray-based pathogen detection. Appl Environ Microbiol 70: 3047-3054.

Wang D, Coscoy L, Zylberberg M, Avila P C, Boushey H A, et al. (2002) Microarray-based detection and genotyping of viral pathogens. Proc Natl Acad Sci USA 99:15687-15692.

Wang D, Urisman A, Liu Y T, Springer M, Ksiazek T G, et al. (2003) Viral discovery and sequence recovery using DNA microarrays. PLoS Biol 1: E2.

Wong C W, Albert T J, Vega V B, Norton J E, Cutler D J, et al. (2004) Tracking the Evolution of the SARS Coronavirus Using High-Throughput, High-Density Resequencing Arrays. Genome Res 14:398-405.

Wu, D. Y., Ugozzoli, L., Pal, B. K, Qian, J. & Wallace, R. B. (1991) The effect of temperature and oligonucleotide primer length on the specificity and efficiency of amplification by the polymerase chain reaction. DNA Cell Biol 10, 233-238

The invention claimed is:

1. A method of designing at least one oligonucleotide for nucleic acid detection comprising the following steps in any order:

(I) computing an amplification efficiency score ($AES_i$) for every position i of a target nucleic acid $v_a$:

$$AES_i = \sum_{j=i-Z}^{i} \left\{ P^f(j) \times \sum_{k=\max(i+1, j+500)}^{j+Z} P^r(k) \right\}$$

wherein $$\sum_{k=\max(i+1,j+500)}^{j+Z} P^r(k) = P^r(i+1) + P^r(i+2) + \ldots P^r(j+Z);$$

$P^f(i)$ and $P^r(i)$ are the probabilities that a random primer $r_i$ binds to position i of $v_a$ as forward random primer and reverse random primer respectively, and $Z \leq 10000$ bp is the region of $v_a$ desired to be amplified;

(II) identifying and/or selecting at least one region of at least one target nucleic acid to be amplified, the region(s) having an efficiency of amplification (AE) higher than the average AE; and (III) designing at least one oligonucleotide capable of hybridizing to the identified and/or selected region(s), wherein the method is implemented by a computing processing unit.

2. The method according to claim 1, wherein the at least one oligonucleotide capable of hybridizing to the selected region(s) is selected and designed according to at least one of the following criteria:

(a) the selected oligonucleotide(s) has a CG-content from 40% to 60%;

(b) the oligonucleotide(s) is selected by having the highest free energy computed based on Nearest-Neighbor model;

(c) given oligonucleotide $s_a$ and oligonucleotide $s_b$ substrings of target nucleic acids $v_a$ and $v_b$, $s_a$ is selected based on the hamming distance between $s_a$ and any length-m substring $s_b$ from the target nucleic acid $v_b$ and/or on the longest common substring of $s_a$ and oligonucleotide $s_b$;

(d) for any oligonucleotide $s_a$ of length-m specific for the target nucleic acid $v_a$, the oligonucleotide $s_a$ is selected if it does not have any hits with any region of a nucleic acid different from the target nucleic acid, and if the oligonucleotide $s_a$ length-m has hits with the nucleic acid different from the target nucleic acid, the oligonucleotide $s_a$ length-m with the smallest maximum alignment length and/or with the least number of hits is selected; and (e) an oligonucleotide $p_i$ at position i of a target nucleic acid is selected if $p_i$ is predicted to hybridize to the position i of the amplified target nucleic acid.

3. The method according to claim 2, wherein under the criterion (e), an oligonucleotide $p_i$ at position i of a target nucleic acid $v_a$ is selected if $P(p_i|v_a) > \lambda$, wherein $\lambda$ is 0.5 and $P(p_i|v_a)$ is the probability that $p_i$ hybridizes to the position i of the target nucleic acid $v_a$; wherein $$P(p_i | v_a) \approx P(X \leq x_i) = \frac{c_i}{k};$$

X is a random variable representing the amplification efficiency score (AES) values of all oligonucleotide(s) of $v_a$, k is the number of oligonucleotide(s) in $v_a$, and $c_i$ is the number of oligonucleotide(s) whose AES values are $\leq x_i$.

4. The method according to claim 2, wherein $v_a$ of the oligonucleotide is selected and/or designed according to criterion (e) and at least one of the criteria (a) to (d).

5. A method of detecting at least one target nucleic acid comprising the steps of:

(i) providing at least one biological sample;
(ii) amplifying nucleic acid(s) comprised in the biological sample;
(iii) providing at least one oligonucleotide capable of hybridizing to at least one target nucleic acid, if present in the biological sample, wherein the oligonucleotide(s) is designed according to the method of claim 1; and
(iv) contacting the oligonucleotide(s) with the amplified nucleic acids and/or detecting the oligonucleotide(s) hybridized to the target nucleic acid(s).

6. The method according to claim 5, wherein the target nucleic acid to be detected is nucleic acid exogenous to the nucleic acid of the biological sample.

7. The method according to claim 5, wherein in the detection step (iv), the mean of the signal intensities of the probes which hybridize to $v_a$ is statistically higher than the mean of the probes $\notin v_a$, thereby indicating the presence of $v_a$ in the biological sample.

8. The method according to claim 5, wherein in the detection step (iv), the mean of the signal intensities of the probes which hybridize to $v_a$ is statistically higher than the mean of the probes $\notin v_a$, and the method further comprises the step of computing the relative difference of the proportion of probes $\notin v_a$ having high signal intensities to the proportion of the probes used in the detection method having high signal intensities, the density distribution of the signal intensities of probes $v_a$ being more positively skewed than that of probes $\notin v_a$, thereby indicating the presence of $v_a$ in the biological sample.

9. The method according to claim 5, wherein the detection step (iv) comprises evaluating the signal intensity of probe(s) in each signature probe set (SPS) for the target nucleic acid(s) $v_a$ by calculating the distribution of Weighted Kullback-Leibler (WKL) divergence scores:

$$WKL(P_a | \overline{P_a}) = \sum_{j=0}^{k-1} \frac{Q_a(j) \log\left(\frac{Q_a(j)}{Q_{\overline{a}}(j)}\right)}{\sqrt{Q_a(j)[1 - Q_a(j)]}}$$

where $Q_a(j)$ is the cumulative distribution function of the signal intensities of the probes in $P_a$ found in bin $b_j$; $Q_{\overline{a}}(j)$ is the cumulative distribution function of the signal intensities of the probes in $\overline{P_a}$ found in bin $b_j$; $P_a$ is the set of probes of a virus $v_a$ and $\overline{P_a} = P - P_a$.

10. The method according to claim 9, wherein in the detection step (iv), the presence of at least one target nucleic acid in a biological sample is given by a value of Weighted Kullback-Leibler divergence score $\geq$ of 1.0.

11. The method according to claim 9, wherein each signature probe set (SPS) which represents the absence of target nucleic acid(s) $v_a$ has a Weighted Kullback-Leibler (WKL) divergence score of WKL<5, and wherein each signature probe set (SPS) which represents the presence of at least one target nucleic acid $v_a$ has a Weighted Kullback-Leibler (WKL) divergence score of WKL>5.

12. The method according to claim 9, further comprising performing Anderson-Darling test on the distribution of WKL score(s), wherein a result of P>0.05 thereby indicates the absence of target nucleic acid(s) $v_a$ and wherein a result of P<0.05 thereby indicates the presence of target nucleic acid(s) $v_a$.

13. The method according to claim 12, wherein P<0.05 indicates the distribution of WKL scores is not normal and P>0.05 indicates the distribution of WKL scores is normal.

14. The method according to claim 13, wherein if the distribution of WKL scores is not normal, the target nucleic acid molecule with the highest WKL score is identified as present in the biological sample.

15. The method according to claim 14, further comprising removing the highest WKL score from the WKL scores, and repeating the Anderson-Darling test on the remaining WKL scores to determine if the distribution of the remaining WKL scores is normal.

16. The method according to claim 15, wherein if the distribution of the remaining WKL scores is not normal, the target nucleic acid molecule with the next highest WKL score is also identified as present.

17. The method according to claim 16, wherein the target nucleic acid molecule with the next highest WKL score is indicative of a co-infecting pathogen.

18. The method according to claim 16, comprising repeating the steps of removing the next highest WKL score and repeating the Anderson-Darling test until the distribution of the WKL scores becomes normal, thereby detecting the presence of any other target nucleic acid molecules and/or co-infecting pathogens.

19. The method according to claim 1, wherein each of the forward and reverse random primers comprises, 5'-3' orientation, a fixed primer header and a variable primer tail, and wherein at least the variable tail hybridizes to a portion of the target acid $V_a$.

20. An apparatus configured to perform a method of detecting at least one target nucleic acid comprising the steps of:
 (i) providing at least one biological sample;
 (ii) amplifying nucleic acid(s) comprised in the biological sample;
 (iii) providing at least one oligonucleotide capable of hybridizing to at least one target nucleic acid, if present in the biological sample, wherein the oligonucleotide(s) is designed according to the method of claim 1; and
 (iv) contacting the oligonucleotide(s) with the amplified nucleic acids and detecting the oligonucleotide(s) hybridized to the target nucleic acid(s); wherein the detection step comprises evaluating the signal intensity of the probe(s) in each signature probe set (SPS) for the target nucleic acid(s) by calculating the distribution of Weighted Kullback-Leiber (WKL) divergence scores:

$$WKL(P_a | \overline{P_a}) = \sum_{j=0}^{k-1} \frac{Q_a(j) \log\left(\frac{Q_a(j)}{Q_{\overline{a}}(j)}\right)}{\sqrt{Q_{\overline{a}}(j)[1 - Q_{\overline{a}}(j)]}}$$

where $Q_a(j)$ is the cumulative distribution function of the signal intensities of the probes in $P_a$ found in bin $b_j$; $Q_{\overline{a}}(j)$ is the cumulative distribution function of the signal intensities of the probes in $\overline{P_a}$ found in bin $b_j$; $P_a$ is the set of probes of a virus $v_a$ and $\overline{P_a}=P-P_a$.

21. The apparatus according to claim 20, wherein the target nucleic acid to be detected is at least one nucleic acid exogenous to the nucleic acid of the biological sample.

22. The apparatus according to claim 20, wherein the presence of a target nucleic acid in a biological sample is given by a value of Weighted Kullback-Leibler divergence of $\geq 1.0$.

23. The apparatus according to claim 20, wherein each signature probe set (SPS) which represents the absence of target nucleic acid(s) has a Weighted Kullback-Leibler (WKL) divergence score of WKL<5, and wherein each signature probe set (SPS) which represents the presence of at least one target nucleic acid has and/or a Weighted Kullback-Leibler (WKL) divergence score of WKL>5.

24. The apparatus according to claim 20, further comprising performing an Anderson-Darling test on the distribution of WKL score(s), wherein a result of P>0.05 thereby indicates the absence of target nucleic acid(s) and wherein a result of P<0.05 thereby indicates the presence of target nucleic acid(s).

25. A non-transitory electronic storage medium comprising a software with instructions to cause a computing processing unit to perform the method according to claim 1.

26. The method according to claim 1, further comprising preparing the oligonucleotide.

27. A non-transitory electronic storage medium comprising a software with instructions to cause a computing processing unit to determine the WKL divergence score according to claim 9 or perform the Anderson Darling test according to claim 12.

28. A computing processing unit for designing at least one oligonucleotide for nucleic acid detection, the computing processing unit being configured to:
 (I) compute an amplification efficiency score ($AES_i$) for every position i of a target nucleic acid $v_a$:

$$AES_i = \sum_{j=i-Z}^{i} \left\{ P^f(j) \times \sum_{k=\max(i+1, j+500)}^{j+Z} P^r(k) \right\}$$

wherein $$\sum_{k=\max(i+1, j+500)}^{j+Z} P^r(k) = P^r(i+1) + P^r(i+2) + \ldots P^r(j+Z);$$

$P^f(i)$ and $P^r(i)$ are the probabilities that a random primer $r_i$ binds to position i of $v_a$ as forward random primer and reverse random primer respectively, and $Z \leq 10000$ bp is the region of $v_a$ desired to be amplified;
 (II) identify and/or select at least one region(s) of at least one target nucleic acid to be amplified, the region(s) having an efficiency of amplification (AE) higher than the average AE; and
 (III) design at least one oligonucleotide capable of hybridizing to the identified and/or selected region(s).

29. The computing processing unit according to claim 28, wherein the oligonucleotide(s) capable of hybridizing to the selected region(s) is selected and/or designed according to at least one of the following criteria:

(a) the selected oligonucleotide(s) has a CG-content from 40% to 60%;
(b) the oligonucleotide(s) is selected by having the highest free energy computed based on Nearest-Neighbor model;
(c) given oligonucleotide $s_a$ and oligonucleotide $s_b$ substrings of target nucleic acids $v_a$ and $v_b$, $s_a$ is selected based on the hamming distance between $s_a$ and any length-m substring $s_b$ from the target nucleic acid $v_b$ and/or on the longest common substring of $s_a$ and oligonucleotide $s_b$;
(d) for any oligonucleotide $s_a$ of length-m specific for the target nucleic acid $v_a$, the oligonucleotide $s_a$ is selected if it does not have any hits with any region of a nucleic acid different from the target nucleic acid, and if the oligonucleotide $s_a$ length-m has hits with the nucleic acid different from the target nucleic acid, the oligonucleotide $s_a$ length-m with the smallest maximum alignment length and/or with the least number of hits is selected; and
(e) at least one oligonucleotide $p_i$ at position i of a target nucleic acid is selected if $p_i$ is predicted to hybridize to the position i of the amplified target nucleic acid.

30. The computing processing unit according to claim 29, wherein under the criterion (e), an oligonucleotide $p_i$ at position i of a target nucleic acid $v_a$ is selected if $P(p_i|v_a) > \lambda$, wherein $\lambda$ is 0.5 and $P(p_i|v_a)$ is the probability that $p_i$ hybridizes to the position i of the target nucleic acid $v_a$; wherein $$P(p_i | v_a) \approx P(X \le x_i) = \frac{c_i}{k};$$

X is the random variable representing the amplification efficiency score (AES) values of all oligonucleotides of $v_a$, k is the number of oligonucleotides in $v_a$, and $c_i$ is the number of oligonucliotides whose AES values are $\le x_i$.

31. The computing processing unit according to claim 29, wherein the oligonucleotide is selected and/or designed according to criterion (e) and at least one of the criteria (a) to (d).

32. The computing processing unit according to claim 28, wherein each of the forward and reverse random primers comprises, in a 5'-3' orientation, a fixed primer header and a variable primer tail, and wherein at least the variable tail hybridizes to a portion of the target nucleic acid $v_a$.

* * * * *